United States Patent
Liu et al.

(10) Patent No.: US 10,266,535 B2
(45) Date of Patent: Apr. 23, 2019

(54) INHIBITOR OF FLT3 KINASE AND USE THEREOF

(71) Applicants: HEFEI INSTITUTES OF PHYSICAL SCIENCE, CHINESE ACADEMY OF SCIENCES, Hefei, Anhui (CN); HEFEI COSOURCE PHARMACEUTICAL CO., LTD., Hefei, Anhui (CN)

(72) Inventors: Jing Liu, Anhui (CN); Qingsong Liu, Anhui (CN); Xixiang Li, Anhui (CN); Aoli Wang, Anhui (CN); Hong Wu, Anhui (CN); Cheng Chen, Anhui (CN); Wenchao Wang, Anhui (CN); Chen Hu, Anhui (CN); Zheng Zhao, Anhui (CN); Jiaxin Wu, Anhui (CN); Juan Liu, Anhui (CN); Kailin Yu, Anhui (CN); Wei Wang, Anhui (CN); Li Wang, Anhui (CN); Beilei Wang, Anhui (CN)

(73) Assignees: HEFEI INSTITUTES OF PHYSICAL SCIENCE, CHINESE ACADEMY OF SCIENCES, Hefei, Anhui (CN); HEFEI COSOURCE PHARMACEUTICAL CO., LTD., Hefei, Anhui (CN)

( * ) Notice: Subject to any disclaimer, the term of this patent is extended or adjusted under 35 U.S.C. 154(b) by 0 days.

(21) Appl. No.: 15/544,676

(22) PCT Filed: Aug. 7, 2015

(86) PCT No.: PCT/CN2015/086318
§ 371 (c)(1),
(2) Date: Jul. 19, 2017

(87) PCT Pub. No.: WO2016/115869
PCT Pub. Date: Jul. 28, 2016

(65) Prior Publication Data
US 2018/0030054 A1 Feb. 1, 2018

(30) Foreign Application Priority Data

Jan. 21, 2015 (CN) .......................... 2015 1 0028177
Mar. 25, 2015 (CN) .......................... 2015 1 0130223

(51) Int. Cl.
A61K 31/5377 (2006.01)
A61K 31/519 (2006.01)
C07D 487/04 (2006.01)

(52) U.S. Cl.
CPC .......... C07D 487/04 (2013.01); A61K 31/519 (2013.01); A61K 31/5377 (2013.01)

(58) Field of Classification Search
CPC . A61K 31/5377; A61K 31/519; C07D 487/04

USPC ....................................................... 514/234.2
See application file for complete search history.

(56) References Cited

U.S. PATENT DOCUMENTS

| | | | |
|---|---|---|---|
| 7,718,662 B1 | 5/2010 | Chen et al. | |
| 2011/0086866 A1 | 4/2011 | Chen et al. | |
| 2014/0303161 A1 | 10/2014 | Goldstein et al. | |
| 2014/0323464 A1 | 10/2014 | Taunton, Jr. et al. | |

FOREIGN PATENT DOCUMENTS

| | | |
|---|---|---|
| CN | 102656173 A | 9/2012 |
| CN | 103717602 A | 4/2014 |
| WO | WO 02/080926 A1 | 10/2002 |

(Continued)

OTHER PUBLICATIONS

Li et al., Journal of Medicinal Chemistry (2015), 58(24), 9625-9638.*
Ansari-Lari a. et al., "FLT3 Mutations in Myeloid Sarcoma", *British Journal of Haematology* 126:785 791 (2004).
Anon, "A Process for Preparing (S)-1-(3-(4-Amino-3-(4-Phenoxyphenyl)-1H-Pyrazolo[3,4-d]Pyrimidin-1-yl)Piperidin-1-yl)Prop-2-en-1-One", IP.com Journal 14(9A) 3 pages, (Aug. 19, 2014).

(Continued)

*Primary Examiner* — Niloofar Rahmani
(74) *Attorney, Agent, or Firm* — Scully Scott Murphy & Presser

(57) ABSTRACT

Provided in the present invention is a novel inhibitor of FLT3 kinase, comprising a compound of formula (I) or a pharmaceutically acceptable salt, solvate, isomer, ester, acid, metabolite or prodrug thereof. Also provided in the present invention are a pharmaceutical composition comprising a compound of formula (I) and a use and method for preventing or treating cell proliferative conditions and/or FLT3-related conditions, in particular for conditions responding to the inhibition of FLT3 kinase (especially FLT3/ITD mutant kinases).

Formula (I)

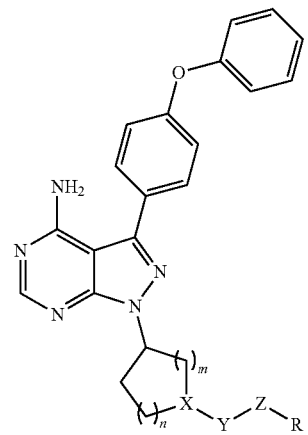

7 Claims, 8 Drawing Sheets

(56) References Cited

FOREIGN PATENT DOCUMENTS

| WO | 2008039218 A2 | | 4/2008 |
|---|---|---|---|
| WO | WO 2011/046964 A2 | | 4/2011 |
| WO | WO 2012/158843 A2 | | 11/2012 |
| WO | WO 2013/003629 A2 | | 1/2013 |
| WO | WO 2014/017659 A1 | | 1/2014 |
| WO | WO 2014/139970 A1 | | 9/2014 |
| WO | 2014187319 A1 | | 11/2014 |
| WO | 2016151438 | * | 9/2016 |

OTHER PUBLICATIONS

Anon, "Solid State Forms of (S)-3-(4-Phenoxyphenyl)-1-(Piperidin-3-yl)-1H-Pyrazolo[3,4-d]Pyrimidin-4-Amine", 14(8B) 4 pages (Aug. 13, 2014).

Kottaridis D., "FLT3 Mutations and Leukaemia", *British Journal of Haematology* 122:523-538 (2003).

Lyman S.D. et al., "Characterization of the Protein Encoded by the Flt3 (Flk2) Receptor-Like Tyrosine Kinase Gene", *Oncogen* 8:815-822 (1993).

International Search Report dated Nov. 25, 2015 received in International Application No. PCT/CN2015/086318.

International Preliminary Report on Patentability dated Nov. 25, 2015 received in International Application No. PCT/CN2015/086318.

Chinese Office Action dated Apr. 20, 2017 received in Chinese Patent Application No. CN201510547224.9, with partial English translation.

Veeraraghavan, S. et al., "Simultaneous quantification of lenalidomide, ibrutinib and its active metabolite PCI-45227 in rat plasma by LC-MS/MS: Application to a pharmacokinetic study", Journal of Pharmaceutical and Biomedical Analysis, Dec. 2014, vol. 107, pp. 151-158.

Extended European Search Report dated Aug. 14, 2018 issued in EP Application No. 15878539.4.

* cited by examiner

FLT3/ITD

BTK a b a b

INHIBITOR OF FLT3 KINASE AND USE THEREOF

FIELD OF THE INVENTION

The present invention relates to compounds used as novel inhibitors of FLT3 kinase, pharmaceutical compositions comprising the compounds, as well as uses and methods for using these compounds and compositions to to reduce or inhibit the activity of FLT3 kinase and/or mutant FLT3 kinase in a cell or a subject, and uses and methods of these compounds and compositions for preventing or treating cell proliferative conditions and/or FLT3-related conditions in a subject.

BACKGROUND OF THE INVENTION

Protein kinases are enzymatic components of the signal transduction pathways which catalyze the transfer of the terminal phosphate from ATP to the hydroxy group of tyrosine, serine and/or threonine residues of proteins. The overexpression or inappropriate expression of normal or mutant protein kinases in mammals has been a topic of extensive study and has been demonstrated to play a significant role in the development of many diseases, including diabetes, angiogenesis, psoriasis, restenosis, ocular diseases, schizophrenia, rheumatoid arthritis, atherosclerosis, cardiovascular disease and cancer. In summary, inhibitors of protein kinases have particular utility in the treatment of human and animal disease.

FLT3 (Fms-like tyrosine kinase 3), together with c-Kit, c-FMS and PDGFR, belongs to members of receptor tyrosine kinase III (RTK III) family, the protein structure of which include an extracellular region consisting of five immunoglobulin (Ig)-like domains, a transmembrane region, an intracellular juxtamembrane (JM) region, as well as two tyrosine kinase (TK) domains interrupted by a kinase insert in the intracellular region (S. D. Lyman et al., Oncogene, 1993, 8, 815-822). In 1996, the FLT3 mutations were first identified in AML cells, and the mutation type was internal tandem duplications (FLT3/ITD). In recent years, many studies have demonstrated that the FLT3-actived mutations play a very important pathological role in the development of AML and the progression of the disease. AML patients with the FLT3/ITD-actived mutations normally have unique clinical features, such as high peripheral blood leucocyte count, poor clinical prognosis, and easy relapse, and the like. As the method for detecting the FLT3-actived mutations is simple and practicable, more and more researchers are committed to developing FLT3 as a conventional detection means of AML for guiding the therapy and prognostic prediction in AML patients, and as a detection means of minimal residual leukemia, and as a new target for chemotherapy in leukemia patients.

Hematological malignancies are cancers of the body's blood forming and immune systems, the bone marrow and lymphatic tissues. Whereas in normal bone marrow, FLT3 expression is restricted to early progenitor cells, in hematological malignancies, FLT3 is expressed at high levels or FLT3 mutations cause an uncontrolled induction of the FLT3 receptor and downstream molecular pathway, possibly Ras activation. Hematological malignancies include leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), adult T-cell ALL, AML with trilineage myelodysplasia (AML/TMDS), mixed lineage leukemia (MLL), myelodysplasia syndromes (MDSs), myeloproliferative disorders (MPD), multiple myeloma (MM) and myeloid sarcoma (Kottaridis, P. D., R. E. Gale et al., FLT3 mutations and leukaemia, British Journal of Haematology, 2003, 122(4):523-38; Ansari-Lari, Ali et al., FLT3 mutations in myeloid sarcoma, British Journal of Haematology, 2004, 126(6):785-91.).

It has been confirmed that there are mainly two classes of FLT3-actived mutations: Internal tandem duplications (ITD) and point mutation in the activation loop (TKD point mutation). Both classes of FLT3-actived mutations can cause spontaneous phosphorylation of FLT3, which leads to ligand-independent constitutive activation of FLT3, which further activates its downstream abnormal signal transduction, thereby acing to promote proliferation and inhibit apoptosis, so that the leukemia patients with the mutant phenotype have poor clinical prognosis.

At present, the targeting inhibition of FLT3 and mutant FLT3 has become a hotspot. It is mainly for the development of small molecules as tyrosine kinase inhibitors, which inhibit the kinase activity by competing with FLT3 tyrosine kinase for ATP binding sites. The inhibitors of FLT3 kinase, such as AC220, have now been introduced into clinical practice.

SUMMARY OF THE INVENTION

The present invention provides a novel inhibitor of FLT3 kinase, comprising a compound of formula (I) or a pharmaceutically acceptable salt, solvate, isomer, ester, acid, metabolite or prodrug thereof:

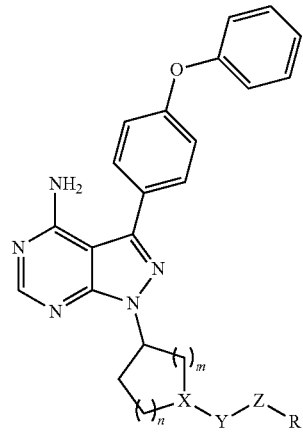

Formula (I)

Wherein:
m is an integer selected from 1 or 2;
n is an integer selected from 0 to 4;
X is N or CH, and when X is N, Y is a chemical bond, and when X is CH, Y is NH;
Z is selected from the group consisting of $CH_2$,

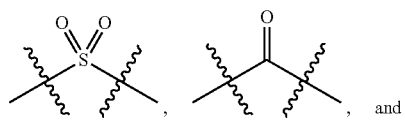

, and

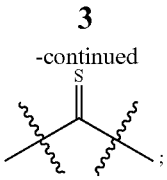

R is selected from the group consisting of amino, unsubstituted C1-C8 alkyl or C1-C8 alkyl optionally substituted with 1 to 3 independent R1 on carbon atoms, unsubstituted C3-C8 cycloalkyl or C3-C8 cycloalkyl optionally substituted with 1 to 3 independent R1 on carbon atoms, unsubstituted C1-C8 haloalkyl or C1-C8 haloalkyl optionally substituted with 1 to 3 independent R1 on carbon atoms, unsubstituted C1-C8 aminoalkyl or C1-C8 aminoalkyl optionally substituted with 1 to 3 independent R1 on carbon atoms or optionally substituted with R2 on heteroatoms, unsubstituted C1-C8 cyanoalkyl or C1-C8 cyanoalkyl optionally substituted with 1 to 3 independent R1 on carbon atoms, unsubstituted C1-C8 hydroxyalkyl or C1-C8 hydroxyalkyl optionally substituted with 1 to 3 independent R1 on carbon atoms, unsubstituted C1-C8 alkoxy or C1-C8 alkoxy optionally substituted with 1 to 3 independent R1 on carbon atoms, unsubstituted C3-C8 heterocycloalkyl or C3-C8 heterocycloalkyl optionally substituted with 1 to 3 independent R1 on carbon atoms or optionally substituted with R2 on heteroatoms, unsubstituted aryl or aryl optionally substituted with 1 to 3 independent R1 on carbon atoms, unsubstituted heteroaryl or heteroaryl optionally substituted with 1 to 3 independent R1 on carbon atoms or optionally substituted with R2 on heteroatoms, carbamoyl, unsubstituted C1-C8 alkyl formyl or C1-C8 alkyl formyl optionally substituted with 1 to 3 independent R1 on carbon atoms, unsubstituted C3-C8 cycloalkyl formyl or C3-C8 cycloalkyl formyl optionally substituted with 1 to 3 independent R1 on carbon atoms, unsubstituted C3-C8 heterocycloalkyl formyl or C3-C8 heterocycloalkyl formyl optionally substituted with 1 to 3 independent R1 on carbon atoms or optionally substituted with R2 on heteroatoms, unsubstituted aryl formyl or aryl formyl optionally substituted with 1 to 3 independent R1 on carbon atoms, unsubstituted C1-C8 alkylamino(C1-C8)alkyl or C1-C8 alkylamino(C1-C8)alkyl optionally substituted with 1 to 3 independent R1 on carbon atoms, unsubstituted C1-C8 alkyl(C3-C6 cycloalkyl) or C1-C8 alkyl(C3-C6 cycloalkyl) optionally substituted with 1 to 3 independent R1 on carbon atoms, unsubstituted C3-C6 cycloalkyl(C1-C8 alkyl) or C3-C6 cycloalkyl(C1-C8 alkyl) optionally substituted with 1 to 3 independent R1 on carbon atoms, unsubstituted C1-C8 alkyl(C3-C6 heterocycloalkyl) or C1-C8 alkyl(C3-C6 heterocycloalkyl) optionally substituted with 1 to 3 independent R1 on carbon atoms or optionally substituted with R2 on heteroatoms, unsubstituted C3-C6 heterocycloalkyl(C1-C8 alkyl) or C3-C6 heterocycloalkyl(C1-C8 alkyl) optionally substituted with 1 to 3 independent R1 on carbon atoms or optionally substituted with R2 on heteroatoms, unsubstituted C1-C8 alkyl(aryl) or C1-C8 alkyl(aryl) optionally substituted with 1 to 3 independent R1 on carbon atoms, unsubstituted C1-C8 alkyl(heteroaryl) or C1-C8 alkyl(heteroaryl) optionally substituted with 1 to 3 independent R1 on carbon atoms or optionally substituted with R2 on heteroatoms, and unsubstituted C1-C8 aminoalkyl(carbamoyl) or C1-C8 aminoalkyl(carbamoyl) optionally substituted with 1 to 3 independent R1 on carbon atoms;

R1 is selected from the group consisting of halogen, amino, nitro, cyano, hydroxy, C1-C8 alkyl, C3-C8 cycloalkyl, C1-C8 alkoxy, aryl, heteroaryl optionally substituted with R2 on heteroatoms, C1-C8 alkoxycarbonyl, C1-C8 alkyl(heteroaryl) optionally substituted with R2 on heteroatoms, and C1-C8 alkyl(C3-C6 heterocycloalkyl) optionally substituted with R2 on heteroatoms;

R2 is selected from the group consisting of amino protecting groups, C1-C8 alkyl, and C1-C8 alkoxycarbonyl. The amino protecting group is independently selected from the group consisting of tert-butoxycarbonyl (Boc), benzyloxycarbonyl (Cbz), 9-fluorenylmethoxycarbonyl (FMOC), benzyl (Bn) and p-methoxyphenyl (PMP).

In some examples, n is preferably 1 or 2.

In some examples, Z is preferably

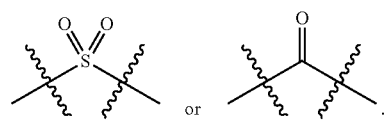

In some examples, R is preferably selected from the group consisting of substituted or unsubstituted C1-C6 alkyl (such as methyl, ethyl, n-propyl, isopropyl, n-butyl, isobutyl, tert-butyl, n-pentyl, isopentyl, and neopentyl, and the like), C1-C4 haloalkyl (such as chloromethyl, trifluoromethyl, trichloromethyl, chloroethyl, bromoethyl, trifluoroethyl, trifluoroethyl, chloropropyl, bromopropyl, chlorobutyl, and bromobutyl, and the like), C3-C6 cycloalkyl (such as cyclopropyl, cyclobutyl, cyclopentyl, and cyclohexyl, and the like), amino, carbamoyl, C1-C6 aminoalkyl (such as methyl, ethyl, propyl, butyl, and pentyl, and the like, substituted with an amino group on any carbon atoms, and optionally substituted with R2, e.g. C1-4 alkyl and the amino protecting groups on N), heteroaryl (such as pyridyl, pyrimidyl, isoxazolyl, and benzodioxolyl, and the like, optionally substituted with an amino group on carbon atoms), C3-C6 heterocycloalkyl (such as piperazinyl, and piperidyl, and the like, optionally substituted with C1-C4 alkyl and C1-C4 alkoxycarbonyl on N atoms), aryl (such as phenyl, optionally substituted with C1-C4 alkoxycarbonyl, p-methyl(piperazinyl)methyl on carbon atoms), C1-C4 cyanoalkyl (for example, cyanomethyl, cyanoethyl, cyanopropyl, and cyanobutyl, and the like), di(C1-C4 alkyl)-N—(C1-C4)alkyl (such as dimethylaminomethyl, diethylaminomethyl, dimethylaminoethyl, diethylaminoethyl, dimethylaminopropyl, and dimethylaminobutyl, and the like), C1-C6 hydroxyalkyl (such as methyl, ethyl, propyl, butyl, and pentyl, and the like, substituted with a hydroxyl group on any carbon atoms, and optionally substituted with an amino group on carbon atoms), C1-C4 alkyl(C3-C6 heterocycloalkyl) (such as morpholinylmethyl, piperazinylmethyl, and piperazinylethyl, and the like, optionally substituted with C1-C4 alkyl on N atoms), C1-C4 alkyl(C3-C6 cycloalkyl) (such as cyclopropylmethyl, cyclobutylmethyl, cyclopentylmethyl, cyclopropylethyl, cyclobutylethyl, cyclopentylethyl, cyclopropylpropyl, and cyclopropylbutyl, and the like), C1-C4 aminoalkyl (carbamoyl) (such as ethyl(carbamoyl), and propyl (carbamoyl), and the like, substituted with an amino group on any carbon atoms), C1-C4 alkyl(heteroaryl) (such as imidazolylethyl, indolylethyl, imidazolypropyl, and indolylpropyl, and the like, optionally substituted with an amino group on carbon atoms), and C1-C4 alkyl(aryl) (such as benzyl, phenylethyl, and phenylpropyl, and the like, optionally substituted with an amino group, a hydroxyl group on carbon atoms).

In some embodiments, m is 1, and X is N, Y is a chemical bond; the compound of the present invention is represented by formula (II):

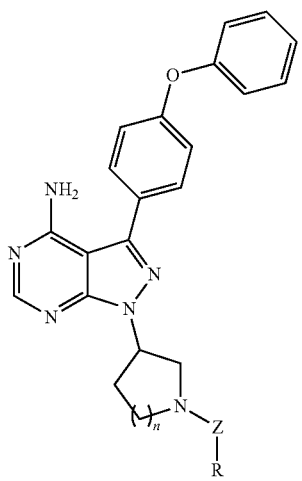

Formula (II)

Wherein, n, Z and R are as defined above.

In another embodiment, m is 2, and X is N, Y is a chemical bond; the compound of the present invention is represented by formula (III):

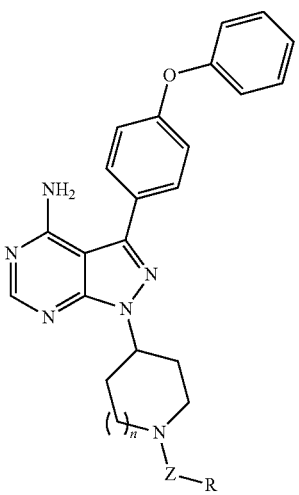

Formula (III)

Wherein, n, Z and R are as defined above. In the embodiment, n is preferably 1.

In yet another embodiment, m is 2, and X is CH, Y is NH; the compound of the present invention is represented by formula (IV):

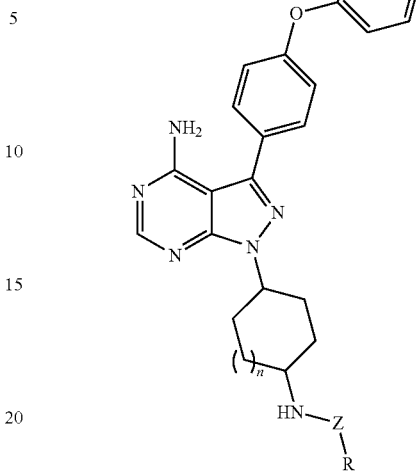

Formula (IV)

Wherein, n, Z and R are as defined above. In the embodiment, n is preferably 1.

In another aspect, the present invention provides a pharmaceutical composition comprising a therapeutically effective amount of at least one compound provided herein, or a pharmaceutically acceptable salt, solvate, isomer, ester, acid, metabolite or prodrug thereof, and a pharmaceutically acceptable carrier or excipient, and optionally other therapeutic agents.

In a further aspect, the present invention provides a method for preparing compounds of formula (I), (II), (III) or (IV), or a pharmaceutically acceptable salt, solvate, isomer, ester, acid, metabolite or prodrug thereof in the present invention.

In a further aspect, the present invention relates to a use of compounds of formula (I), (II), (III) or (IV), or a pharmaceutically acceptable salt, solvate, isomer, ester, acid, metabolite or prodrug thereof, for reducing or inhibiting the activity of FLT3 kinase and/or mutant FLT3 kinase in vivo or in vitro.

In a further aspect, the present invention relates to a use of compounds of formula (I), (II), (III) or (IV), or a pharmaceutically acceptable salt, solvate, isomer, ester, acid, metabolite or prodrug thereof, or the pharmaceutical composition comprising compounds of formula (I), (II), (III) or (IV), in the preparation of a medicament for the treatment of cell proliferative conditions and/or FLT3-related conditions.

In particular, said conditions respond to an inhibition of FLT3 kinase or mutant FLT3 kinase. FLT3 mutations include ITD mutations and TKD point mutations, especially FLT3/ITD mutations.

DETAILED DESCRIPTION OF THE INVENTION

Terminology

Figure 1:
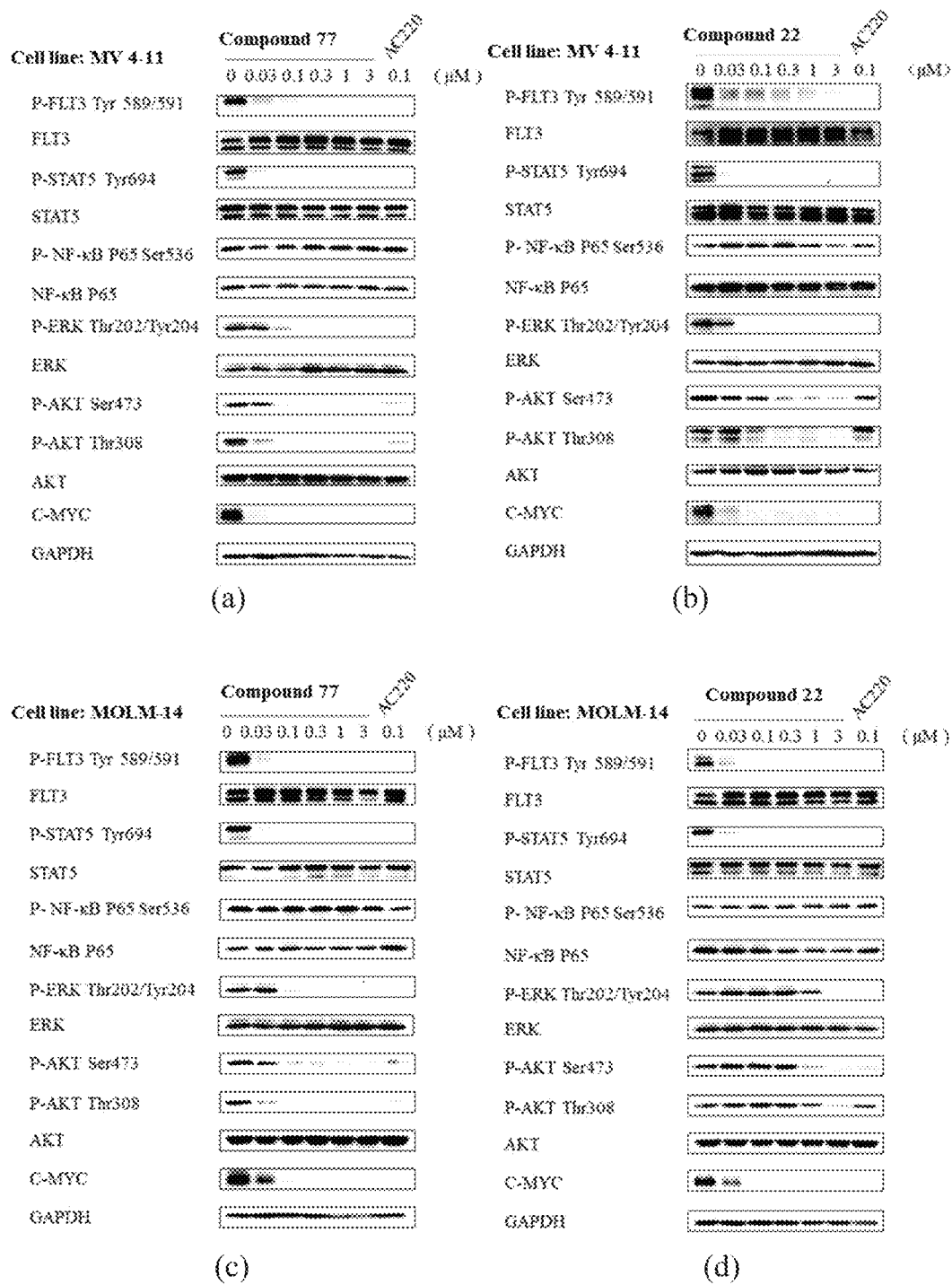
FIGS. 1a to 1f illustrate the effects of Compound 22, Compound 77 and Compound 84 on FLT3 relatively closely related proteins and associated signaling pathways in MV 4-11 and MOLM-14 cells, respectively.
Figure 1:
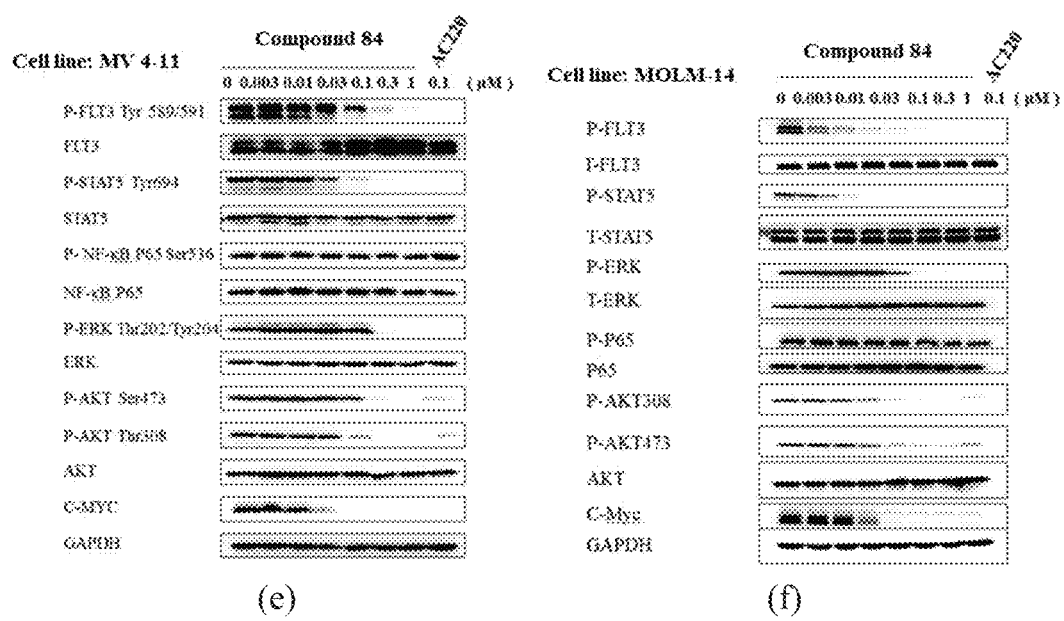

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology, within the skill of the art are employed in the invention. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed of conventional methods well known in the art and as described in various general and more specific references that are cited and discussed throughout the present specification.

The term "alkyl" refers to an aliphatic hydrocarbon group, which may have branched or straight chain. Depending on the structure, an alkyl group can be a monoradical or a diradical (i.e., an alkylene group). In the invention, the alkyl group is preferable a "lower alkyl" having 1 to 6 carbon atoms. Typical alkyl groups include, but are not limited to, methyl, ethyl, propyl, isopropyl, butyl, isobutyl, tertiary butyl, pentyl, hexyl, and the like.

"Alkoxy" refers to a —O-alkyl group, where alkyl is as defined herein. Typical alkoxy groups include, but are not limited to, methoxy, ethoxy, propoxy, butoxy, pentyloxy, hexyloxy, and the like.

"Alkoxyalkyl" refers to an alkyl radical, as defined herein, substituted with an alkoxy group, as defined herein.

As used herein, the term "cyano" refers to a group of formula —CN.

The term "amino" refers to an —NH$_2$ group.

The term "alkylamino" refers to an amino substituent which is further substituted with one or two alkyl groups, specifically the group —NRR', wherein R and R' are each independently selected from the group consisting of hydrogen or lower alkyl, with the proviso that —NRR' is not —NH$_2$. The term "aralkylamino" as used herein refers to the group —NRR', wherein R is lower aralkyl, and R' is hydrogen, lower alkyl, aryl or lower aralkyl. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The term "cyanoalkyl" refers to an alkyl substituent which is further substituted with one or more cyano groups. The term "alkylcarbonyl" refers to a carbonyl group which is further substituted with one alkyl group. The term "alkylcarbonylalkyl" refers to an alkyl group which is further substituted with one alkylcarbonyl group. The term "alkoxycarbonyl" refers to a carbonyl group which is further substituted with one alkoxy group. The alkyl or aryl portion of alkylamino, aminoalkyl, hydroxyalkyl, cyanoalkyl, alkylcarbonyl, alkylcarbonylalkyl, and alkoxycarbonyl may be optionally substituted with one or more substituents.

"Alkylaminoalkyl" refers to an alkyl radical, as defined herein, substituted with an alkylamine, as defined herein.

The term "aromatic" refers to a planar ring having a delocalized π-electron system containing 4n+2 π electrons, where n is an integer. Aromatic rings can be formed by five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

"Alkyl(aryl)" or "aralkyl" means an alkyl radical, as defined herein, substituted with an aryl group, as defined herein. Non-limiting alkyl(aryl) groups include benzyl, phenethyl, and the like.

The term "cycloalkyl" refers to a monocyclic or polycyclic radical that contains only carbon and hydrogen. Cycloalkyl groups include groups having from 3 to 8 ring atoms. Depending on the structure, a cycloalkyl group can be a monoradical or a diradical (e.g., a cycloalkylene group). In the present invention, the cycloalkyl group is preferably a cycloalkyl having 3 to 8 carbon atoms, and more preferably a "lower cycloalkyl" having 3 to 6 carbon atoms.

"Alkyl(cycloalkyl)" or "cycloalkylalkyl" means an alkyl radical, as defined herein, substituted with a cycloalkyl group, as defined herein. Non-limiting alkyl(cycloalkyl) groups include cyclopropylmethyl, cyclobutylmethyl, cyclopentylmethyl, cyclohexylmethyl, and the like.

As used herein, the term "heteroalkyl" refers to an alkyl radical, as defined herein, in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule.

The term "heteroaryl" refers to an aryl group that includes one or more ring heteroatoms selected from nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, indazolyl, indolizinyl, phthalazinyl, pyridazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, naphthyridinyl, furopyridinyl, and the like.

As used herein, the term "heterocycloalkyl" refers to a non-aromatic ring wherein one or more atoms forming the ring is a heteroatom selected from the group consisting of nitrogen, oxygen and sulfur. Heterocycloalkyl rings can be formed by three, four, five, six, seven, eight, nine, or more than nine atoms. Heterocycloalkyl rings can be optionally substituted. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group can be a monoradical or a diradical (i.e., a heterocycloalkylene group).

The term "alkyl(heteroaryl)" or "heteroarylalkyl" means an alkyl radical, as defined herein, substituted with a heteroaryl group, as defined herein.

The term "alkyl(heterocycloalkyl)" or "heterocycloalkylalkyl" means an alkyl radical, as defined herein, substituted with a heterocycloalkyl group, as defined herein.

The term "halo" or "halogen" means fluoro, chloro, bromo and iodo.

The terms "haloalkyl", "haloalkoxy" and "haloheteroalkyl" include alkyl, alkoxy and heteroalkyl structures in which at least one hydrogen is replaced with a halogen atom. In certain embodiments in which two or more hydrogen atoms are replaced with halogen atoms, the halogen atoms are the same or different as one another.

The term "acyl" means a monovalent radical remaining in an organic or inorganic oxygen-containing acid that removes hydroxyl groups, with the general formula of R-M(O)—, wherein M is generally C.

The term "carbonyl" is an organic functional group (C=O) formed by carbon atom and oxygen atom through a double bond linkage.

The term "substituted" means that the referenced group may be substituted with one or more additional group(s) individually and independently selected from the group consisting of alkyl, cycloalkyl, aryl, heteroaryl, hydroxy, alkoxy, cyano, halo, amide, nitro, haloalkyl, amino, alkoxycarbonyl, alkyl(heteroaryl), alkyl(heterocycloalkyl), and the like.

The terms "inhibits", "inhibiting", or "inhibitor" of a kinase, as used herein, refer to inhibition of phosphotransferase activity.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics*, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionic acid esters and acyl esters. Prodrugs which are converted to active forms through other mechanisms in vivo are also included. In aspects, the compounds of the invention are prodrugs of any of the formulae herein.

The term "isomers" refers to compounds which have identical chemical constitution, but differ with regard to the arrangement of the atoms or groups in space, which is intended to include diastereoisomers, enantiomers, regioisomers, structural isomers, rotational isomers, tautomers, and the like. For compounds which contain one or more stereogenic centers, e.g., chiral compounds, the methods of the present invention may be carried out with an enantiomerically enriched compound, a racemate, or a mixture of diastereomers.

As used herein, the term "target protein" refers to a protein molecule or a portion of a protein capable of being bound by a selective binding compound. In certain embodiments, a target protein is FLT3.

As used herein, $IC_{50}$ refers to an amount, concentration or dosage of a particular test compound that achieves a 50% inhibition of a maximal response, in an assay that measures such response.

As used herein, $EC_{50}$ refers to a dosage, concentration or amount of a test compound that elicits a dose-dependent response at 50% of maximal expression of a particular response that is induced, provoked or potentiated by the particular test compound.

The Novel Kinase Inhibitors of the Present Invention

The present invention provides a novel inhibitor of FLT3 kinase, comprising a compound of formula (I) or a pharmaceutically acceptable salt, solvate, isomer, ester, acid, metabolite or prodrug thereof:

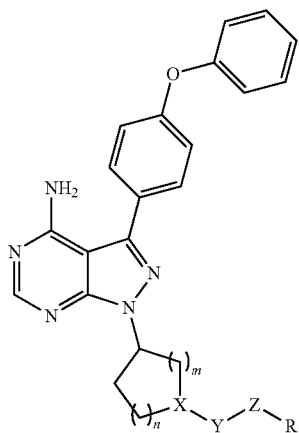

Formula (I)

Wherein:

m is an integer selected from 1 or 2;

n is an integer selected from 0 to 4;

X is N or CH, and when X is N, Y is a chemical bond, and when X is CH, Y is NH;

Z is selected from the group consisting of $CH_2$,

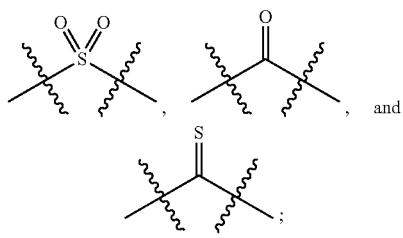

, and ;

R is selected from the group consisting of amino, unsubstituted C1-C8 alkyl or C1-C8 alkyl optionally substituted with 1 to 3 independent R1 on carbon atoms, unsubstituted C3-C8 cycloalkyl or C3-C8 cycloalkyl optionally substituted with 1 to 3 independent R1 on carbon atoms, unsubstituted C1-C8 haloalkyl or C1-C8 haloalkyl optionally substituted with 1 to 3 independent R1 on carbon atoms, unsubstituted C1-C8 aminoalkyl or C1-C8 aminoalkyl optionally substituted with 1 to 3 independent R1 on carbon atoms or optionally substituted with R2 on heteroatoms, unsubstituted C1-C8 cyanoalkyl or C1-C8 cyanoalkyl optionally substituted with 1 to 3 independent R1 on carbon atoms, unsubstituted C1-C8 hydroxyalkyl or C1-C8 hydroxyalkyl optionally substituted with 1 to 3 independent R1 on carbon atoms, unsubstituted C1-C8 alkoxy or C1-C8 alkoxy optionally substituted with 1 to 3 independent R1 on carbon atoms, unsubstituted C3-C8 heterocycloalkyl or C3-C8 heterocycloalkyl optionally substituted with 1 to 3 independent R1 on carbon atoms or optionally substituted with R2 on heteroatoms, unsubstituted aryl or aryl optionally substituted with 1 to 3 independent R1 on carbon atoms, unsubstituted heteroaryl or heteroaryl optionally substituted with 1 to 3 independent R1 on carbon atoms or optionally substituted with R2 on heteroatoms, carbamoyl, unsubstituted C1-C8 alkyl formyl or C1-C8 alkyl formyl optionally substituted with 1 to 3 independent R1 on carbon atoms, unsubstituted C3-C8 cycloalkyl formyl or C3-C8 cycloalkyl formyl optionally substituted with 1 to 3 independent R1 on carbon atoms, unsubstituted C3-C8 heterocycloalkyl formyl or C3-C8 heterocycloalkyl formyl optionally substituted with 1 to 3 independent R1 on carbon atoms or optionally substituted with R2 on heteroatoms, unsubstituted aryl formyl or aryl formyl optionally substituted with 1 to 3 independent R1 on carbon atoms, unsubstituted C1-C8 alkylamino(C1-C8)alkyl or C1-C8 alkylamino(C1-C8)alkyl optionally substituted with 1 to 3 independent R1 on carbon atoms, unsubstituted C1-C8 alkyl(C3-C6 cycloalkyl) or C1-C8 alkyl(C3-C6 cycloalkyl) optionally substituted with 1 to 3 independent R1 on carbon atoms, unsubstituted C3-C6 cycloalkyl(C1-C8 alkyl) or C3-C6 cycloalkyl(C1-C8 alkyl) optionally substituted with 1 to 3 independent R1 on carbon atoms, unsubstituted C1-C8 alkyl(C3-C6 heterocycloalkyl) or C1-C8 alkyl(C3-C6 heterocycloalkyl) optionally substituted with 1 to 3 independent R1 on carbon atoms or optionally substituted with R2 on heteroatoms, unsubstituted C3-C6 heterocycloalkyl(C1-C8 alkyl) or C3-C6 heterocycloalkyl(C1-C8 alkyl) optionally substituted with 1 to 3 independent R1 on carbon atoms or optionally substituted with R2 on heteroatoms, unsubstituted C1-C8 alkyl(aryl) or C1-C8 alkyl(aryl) optionally substituted with 1 to 3 independent R1 on carbon atoms, unsubstituted C1-C8 alkyl(heteroaryl) or C1-C8 alkyl(heteroaryl) optionally substituted with 1 to 3 independent R1 on carbon atoms or optionally substituted with R2 on heteroatoms, and unsubstituted C1-C8 aminoalkyl(carbamoyl) or C1-C8 aminoalkyl(carbamoyl) optionally substituted with 1 to 3 independent R1 on carbon atoms;

R1 is selected from the group consisting of halogen, amino, nitro, cyano, hydroxy, C1-C8 alkyl, C3-C8 cycloalkyl, C1-C8 alkoxy, aryl, heteroaryl optionally substituted with R2 on heteroatoms, C1-C8 alkoxycarbonyl, C1-C8 alkyl(heteroaryl) optionally substituted with R2 on heteroatoms, and C1-C8 alkyl(C3-C6 heterocycloalkyl) optionally substituted with R2 on heteroatoms;

R2 is selected from the group consisting of amino protecting groups, C1-C8 alkyl, and C1-C8 alkoxycarbonyl. The amino protecting group is independently selected from the group consisting of tert-butoxycarbonyl (Boc), benzyloxycarbonyl (Cbz), 9-fluorenylmethoxycarbonyl (FMOC), benzyl (Bn) and p-methoxyphenyl (PMP).

In some examples, n is preferably 1 or 2.

In some examples, Z is preferably

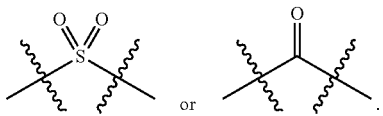

or .

In some examples, R is preferably selected from the group consisting of substituted or unsubstituted C1-C6 alkyl (such as methyl, ethyl, n-propyl, isopropyl, n-butyl, isobutyl, tert-butyl, n-pentyl, isopentyl, and neopentyl, and the like), C1-C4 haloalkyl (such as chloromethyl, trifluoromethyl, trichloromethyl, chloroethyl, bromoethyl, trifluoroethyl, trifluoroethyl, chloropropyl, bromopropyl, chlorobutyl, and bromobutyl, and the like), C3-C6 cycloalkyl (such as cyclopropyl, cyclobutyl, cyclopentyl, and cyclohexyl, and the like), amino, carbamoyl, C1-C6 aminoalkyl (such as methyl, ethyl, propyl, butyl, and pentyl, and the like, substituted with an amino group on any carbon atoms, and optionally substituted with R2, e.g. C1-4 alkyl and the amino protecting groups on N), heteroaryl (such as pyridyl, pyrimidyl, isoxazolyl, and benzodioxolyl, and the like, optionally substituted with an amino group on carbon atoms), C3-C6 heterocycloalkyl (such as piperazinyl, and piperidyl, and the like, optionally substituted with C1-C4 alkyl and C1-C4 alkoxycarbonyl on N atoms), aryl (such as phenyl, optionally substituted with C1-C4 alkoxycarbonyl, p-methyl(piperazinyl)methyl on carbon atoms), C1-C4 cyanoalkyl (for example, cyanomethyl, cyanoethyl, cyanopropyl, and cyanobutyl, and the like), di(C1-C4 alkyl)-N—(C1-C4)alkyl (such as dimethylaminomethyl, diethylaminomethyl, dimethylaminoethyl, diethylaminoethyl, dimethylaminopropyl, and dimethylaminobutyl, and the like), C1-C6 hydroxyalkyl (such as methyl, ethyl, propyl, butyl, and pentyl, and the like, substituted with a hydroxyl group on any carbon atoms, and optionally substituted with an amino group on carbon atoms), C1-C4 alkyl(C3-C6 heterocycloalkyl) (such as morpholinylmethyl, piperazinylmethyl, and piperazinylethyl, and the like, optionally substituted with C1-C4 alkyl on N atoms), C1-C4 alkyl(C3-C6 cycloalkyl) (such as cyclopropylmethyl, cyclobutylmethyl, cyclopentylmethyl, cyclopropylethyl, cyclobutylethyl, cyclopentylethyl, cyclopropylpropyl, and cyclopropylbutyl, and the like), C1-C4 aminoalkyl (carbamoyl) (such as ethyl(carbamoyl), and propyl (carbamoyl), and the like, substituted with an amino group on any carbon atoms), C1-C4 alkyl(heteroaryl) (such as imidazolylethyl, indolylethyl, imidazolypropyl, and indolylpropyl, and the like, optionally substituted with an amino group on carbon atoms), and C1-C4 alkyl(aryl) (such as benzyl, phenylethyl, and phenylpropyl, and the like, optionally substituted with an amino group, a hydroxyl group on carbon atoms).

In some embodiments, m is 1, and X is N, Y is a chemical bond; the compound of the present invention is represented by formula (II):

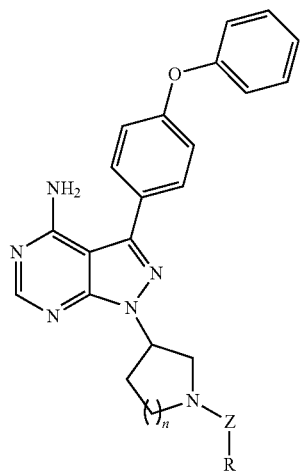

Formula (II)

Wherein, n, Z and R are as defined above. In the embodiment, n is preferably 1 or 2.

In another embodiment, m is 2, and X is N, Y is a chemical bond; the compound of the present invention is represented by formula (III):

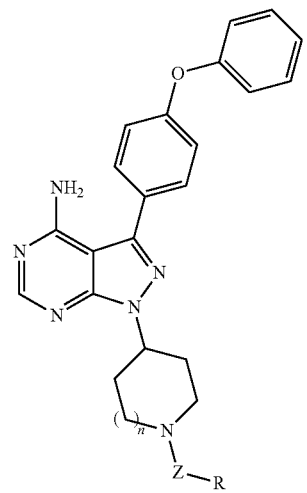

Formula (III)

Wherein, n, Z and R are as defined above. In the embodiment, n is preferably 1.

In yet another embodiment, m is 2, and X is CH, Y is NH; the compound of the present invention is represented by formula (IV):

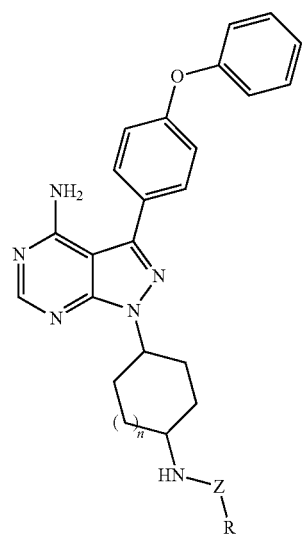

Formula (IV)

Wherein, n, Z and R are as defined above. In the embodiment, n is preferably 1.

The chiral compounds involved in the present invention may be of any configuration or mixed racemates.

In one aspect, it is preferred herein to provide compounds selected from the group consisting of the following compounds, the structures of which are shown in Table 1.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Described herein are novel kinase inhibitors. The pharmaceutically acceptable salts, solvates, isomers, esters, acids, pharmaceutically active metabolites and prodrugs of these compounds are also described herein.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid-addition salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2]oct-2-ene-1-carboxylic acid, 2-naphthalenesulfonic acid, tertiary butylacetic acid, glucoheptonic acid, 4,4'-methylenebis-(3-hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, and the like; (2) base-addition salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

The screening and characterization of the pharmaceutically acceptable salts, polymorphs and/or solvates may be accomplished using a variety of techniques including, but not limited to, thermal analysis, x-ray diffraction, spectroscopy, microscopy, and elemental analysis. The various spectroscopic techniques used include, but are not limited to, Raman, FTIR, UVIS, and NMR (liquid and solid state). The various microscopy techniques include, but are not limited to, IR microscopy and Raman microscopy.

The Pharmaceutical Composition and the Use of the Present Invention

The present invention also relates to a pharmaceutical composition comprising compounds of formula (I), (II), (III) or (IV), or a pharmaceutically acceptable salt, solvate, isomer, ester, acid, metabolite or prodrug thereof, as an active ingredient, and a pharmaceutically acceptable carrier or excipient, and optionally other therapeutic agents.

Compounds of formula (I), (II), (III) or (IV), or a pharmaceutically acceptable salt, solvate, isomer, ester, acid, metabolite or prodrug thereof, as well as the pharmaceutical composition comprising the same, hereinafter referred to as "the substance of the present invention".

The substance of the present invention may be used for treating or preventing cell proliferative conditions and/or FLT3-related conditions, in particular if the conditions respond to an inhibition of a protein tyrosine kinase, especially to an inhibition of FLT3 kinase or mutant FLT3 kinase. FLT3 mutations include ITD mutations and TKD point mutations, especially FLT3/ITD mutations. The "treatment" in the present invention may be therapeutic (e.g., symptomatic treatment) and/or prophylactic. The substance of the present invention may preferably treat or prevent FLT3-related conditions, and in particular, treating or preventing mutant FLT3/ITD-related conditions is preferred.

In particular, the substance of the present invention may be used for treating or preventing cell proliferative conditions selected from the group consisting of benign or malignant tumors, including but not limited to: initiation or progression of solid tumor, B-cell lymphoma, sarcoma, lymphoma, diffuse large B-cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B-cell lymphoma, nodal marginal zone B-cell lymphoma, mantle cell lymphoma, mediastinal (thymic) large B-cell lymphoma, intravascular large B-cell lymphoma, primary effusion lymphoma, Burkitt lymphoma, leukemias, lymphomatoid granulomatosis, breast ductal carcinoma, lobular carcinoma, adenocarcinoma, melanoma, B-cell proliferative disease, brain cancer, kidney cancer, liver cancer, adrenal gland cancer, bladder cancer, breast cancer, lymph cancer, stomach cancer, stomach neoplasm, esophagus cancer, ovarian cancer, colorectal cancer, prostate cancer, pancreas cancer, lung cancer, vagina cancer, membranous adenocarcinoma, thyroid cancer, neck cancer, CNS cancer, malignant glioma, myeloproliferative disease, glioblastoma, multiple myeloma, gastrointestinal cancer, colorectal carcinoma, head and neck neoplasms, brain tumor, epidermal hyperplasia, psoriasis, prostate hyperplasia, neoplasia, neoplasia of epithelial character, lymphomas, breast cancer, or leukemias, or similar diseases, or a combination thereof.

The substance of the present invention may also be used for treating or preventing FLT3-related conditions, especially mutant FLT3/ITD-related conditions, including but not limited to: Hematological malignancies include leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), adult T-cell ALL, AML with trilineage myelodysplasia (AML/TMDS), mixed lineage leukemia (MLL), myelodysplasia syndromes (MDSs), myeloproliferative disorders (MPD), multiple myeloma (MM) and myeloid sarcoma, chronic lymphocytic lymphoma, diffuse large B-cell lymphoma (DLBCL), follicular lymphoma or chronic lymphocytic leukemia, mantle cell lymphoma, mediastinal (thymic) large B-cell lymphoma, intravascular large B-cell lymphoma, primary effusion lymphoma, Burkitt lymphoma, or similar diseases, or a combination thereof.

Compositions for enteral administration, such as nasal, buccal, rectal or, especially, oral administration, and for parenteral administration, such as intravenous, intramuscular or subcutaneous administration, to warm-blooded animals, especially humans, are preferred. The dosage of the active ingredient depends upon the disease to be treated and upon the species, its age, weight, and individual condition, the individual pharmacokinetic data, and the mode of administration.

Said pharmaceutical compositions may optionally be used in combination with known therapeutic methods, such as administration of hormones or radiation. Such other therapeutic agents include, for example, cytostatic agents, other antiproliferative agents.

Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, steroids, antiproliferative antibodies, 17-(allylamino)-17-demethoxygeldanamycin (17-AAG) and temozolomide (TMEMODAL).

The term "aromatase inhibitors" as used herein relates to compounds which inhibit the estrogen production, i.e. the compounds conversed by the substrates androstenedione and testosterone. The term includes, but is not limited to steroids, especially exemestane and formestane and, in particular, non-steroids, especially aminoglutethimide, vorozole, fadrozole, anastrozole and, very especially, letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Aminoglutethimide can be administered, e.g., in the form as it is marketed, e.g. under the trademark ORIMETEN™.

A composition of the present invention comprising an antineoplastic agent which is an aromatase inhibitor may particularly be used for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™ Raloxifene hydrochloride can be administered, e.g., in the form as it is marketed, e.g. under the trademark EVISTA™. Fulvestrant can be formulated as disclosed in U.S. Pat. No. 4,659,516, or it can be administered, e.g., in the form as it is marketed, e.g. under the trademark FASLODEX™.

The term "topoisomerase I inhibitors" as used herein includes, but is not limited to topotecan, irinotecan, 9-nitro-camptothecin conjugate PNU-166148 (Compound A1 in WO99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide. Etoposide can be administered, e.g., in the form as it is marketed, e.g. under the trademark ETOPOPHOS™. Teniposide can be administered, e.g., in the form as it is marketed, e.g. under the trademark VM 26-BRISTOL™. Doxorubicin can be administered, e.g., in the form as it is marketed, e.g. under the trademark ADRIBLASTIN™. Idarubicin can be administered, e.g., in the form as it is marketed, e.g. under the trademark ZAVEDOS™. Mitoxantrone can be administered, e.g., in the form as it is marketed, e.g. under the trademark NOVANTRON™.

The term "microtubule active agents" relates to microtubule stabilizing agents including, but not limited to the taxanes paclitaxel and docetaxel, the vinca alkaloids, e.g., vinblastine, especially vinblastine sulfate, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agents" as used herein includes, but is not limited to cyclophosphamide, ifosfamide and melphalan. Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity. This includes compounds disclosed in WO 02/22577, especially N-hydroxy-3-[[(2-hydroxyethyl) [2-(1H-indol-3-yl)ethyl]-amino]methyl]phenyl]-2E-2-propenamide, N-hydroxy-3-[[(2-hydroxyethyl) [2-(1H-indol-3-yl)ethyl]-amino]methyl]phenyl]-2E-2-propenamide and pharmaceutically acceptable salts thereof. It further especially includes Suberoylanilide hydroxamic acid (SAHA).

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enzyme (COX-2) and which possess antiproliferative activity, e.g., celecoxib (Celebrex), rofecoxib (Vioxx) and lumiracoxib (COX189).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune), everolimus (Certican™), CCI-779 and ABT578.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cis-platin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, Platelet-derived Growth Factor (PDGF), Bcr-Abl, c-Kit, FLT3, Insulin-like Growth Factor I Receptor (IGF-IR) and Cyclin-dependent kinases (CDKs), and anti-angiogenic compounds having another mechanism of action than decreasing the protein kinase activity.

Compounds which decrease the activity of VEGF are especially compounds which inhibit the VEGF receptor, especially the tyrosine kinase activity of the VEGF receptor, and compounds binding to VEGF, and are in particular those compounds, proteins and monoclonal antibodies generically and specifically disclosed in WO98/35958 (describing compounds of formula I), WO00/09495, WO00/27820, WO00/59509, WO98/11223, WO00/27819, WO01/55114, WO01/58899 and EP0769947; those as described by M. Prewett et al. in Cancer Research 59 (1999) 5209-5218, by Z. Zhu et al. in Cancer Res. 58, 1998, 3209-3214, and by J. Mordenti et al in Toxicologic Pathology, vol. 27, no. 1, pp 14-21, 1999; in WO00/37502 and WO94/10202; Angiostatin™, described by M. S. O'Reilly et al., Cell 79, 1994, 315-328.

Compounds which decrease the activity of EGF are especially compounds which inhibit the binding to EGF, and are in particular those compounds generically and specifically disclosed in WO 97/02266 (describing compounds of formula IV), EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980.

Compounds which decrease the activity of c-Src include, but are not limited to, compounds inhibiting the c-Src protein tyrosine kinase activity as defined below and to SH2 interaction inhibitors such as those disclosed in WO97/07131 and WO97/08193.

Compounds inhibiting the c-Src protein tyrosine kinase activity include, but are not limited to, compounds belonging to the structure classes of pyrrolopyrimidines, especially pyrrolo[2,3-d]pyrimidines; purines; pyrazolopyrimidines, especially pyrazolo[3,4-d]pyrimidines; and pyridopyrimidines, especially pyrido[2,3-d]pyrimidines. Preferably, the term relates to those compounds disclosed in WO 96/10028, WO 97/28161, WO97/32879 and WO97/49706.

Compounds which decrease the activity of IGF-IR are especially those disclosed in WO02/92599.

Further specific compounds that decrease protein kinase activity and which may also be used in combination with the compounds of the present invention are Imatinib (Gleevec/Glivec), PKC412, Iressa™ (ZD1839), AEE788 and a pharmaceutically acceptable salt thereof (see also WO03/13541), PTK787 and a pharmaceutically acceptable salt thereof (see also WO98/35958), ZD6474, GW2016, CHIR-200131, CEP-7055/CEP-5214, CP-547632, KRN-633 and SU5416.

Anti-angiogenic compounds having another mechanism of action than decreasing the protein kinase activity include, but are not limited to e.g. thalidomide (THALOMID), celecoxib (Celebrex), and ZD6126.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™. Abarelix can be formulated, e.g., as disclosed in U.S. Pat. No. 5,843,901.

The term "anti-androgens" as used herein includes, but is not limited to bicalutamide (CASODEX™), which can be formulated, e.g., as disclosed in U.S. Pat. No. 4,636,505.

The term "bengamides" relates to bengamides and derivatives thereof having antiproliferative properties.

The term "bisphosphonates" as used herein includes, but is not limited to etridonic acid, pamidronic acid, and alendronic acid. Etridonic acid can be administered, e.g., in the form as it is marketed, e.g. under the trademark DIDRONEL™. Clodronic acid can be administered, e.g., in the form as it is marketed, e.g. under the trademark BONEFOS™ Tiludronic acid can be administered, e.g., in the form as it is marketed, e.g. under the trademark SKELID™. Pamidronic acid can be administered, e.g., in the form as it is marketed, e.g. under the trademark AREDIA™ Alendronic acid can be administered, e.g., in the form as it is marketed, e.g. under the trademark FOSAMAX™. Ibandronic acid can be administered, e.g., in the form as it is marketed, e.g. under the trademark BONDRANAT™. Risedronic acid can be administered, e.g., in the form as it is marketed, e.g. under the trademark ACTONEL™. Zoledronic acid can be administered, e.g., in the form as it is marketed, e.g. under the trademark ZOMETA™.

The term "steroids" includes hydrocortisone, decadron, methylprednisolone and ponisone.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan), PRO64553 (anti-CD40) and 2C4 Antibody.

For the treatment of AML, compounds of formula (I), (II), (III) or (IV) can be used in combination with standard leukemia therapies, especially in combination with therapies used for the treatment of AML. In particular, compounds of formula (I), (II), (III) or (IV) can be administered in combination with e.g. farnesyltransferase inhibitors and/or other drugs used for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of formula (I), (II), (III) or (IV), can be prepared and administered as described in the art such as in the documents cited above.

In the embodiments of the invention, when a patient is treated in accordance with the invention, the amount of a given agent will vary depending upon factors such as the particular dosing regimen, the type of the disease or condition and its severity, the identity (e.g., weight) of the subject or host in need of treatment, but can be routinely determined in a manner known in the art according to the particular circumstances surrounding the case, including, e.g., the specific agent being administered, the route of administration, the condition being treated, and the subject or host being treated. In general, doses employed for adult human treatment will typically be in the range of 0.02-5000 mg per day, such as from about 1-1500 mg per day. The desired dose may conveniently be presented in a single dose or as divided doses administered simultaneously (or over a short period of time) or at appropriate intervals, for example as two, three, four or more sub-doses per day. It will be appreciated by those skilled in the art that, although the above dosage ranges are given, the specific effective amounts may be appropriately adjusted depending on the condition of the patient and the judgment of the practitioner.

Preparation of the Compounds

Compounds of formula (I), (II), (III) or (IV) may be synthesized using standard synthetic techniques known to those of skill in the art or using methods known in the art in combination with methods described herein. In additions, solvents, temperatures and other reaction conditions presented herein may vary according to those of skill in the art.

In certain embodiments, provided herein are methods of making and methods of using kinase inhibitor compounds described herein. In certain embodiments, compounds described herein can be synthesized using the following synthetic schemes. Compounds may be synthesized using methodologies analogous to those described below by the use of appropriate alternative starting materials.

The starring materials used for the synthesis of the compounds described herein may be synthesized or can be obtained from commercial sources. The compounds described herein and other related compounds having different substituents can be synthesized using techniques and materials known to those of skill in the art. Reactions for the preparation of compounds as disclosed herein may be modified by the use of appropriate reagents and conditions, as would be recognized by the skilled person, for the introduction of the various moieties into the molecules as provided herein.

The products of the reactions may be isolated and purified, if desired, using conventional techniques, including, but not limited to, filtration, distillation, crystallization, chromatography and the like. Such products may be characterized using conventional means, including physical constants and spectral data.

Using the synthetic methods described herein, compounds as disclosed herein are obtained in good yields and purity. The compounds prepared by the methods disclosed herein are purified by conventional means known in the art, such as, filtration, recrystallization, chromatography, distillation, and combinations thereof.

Sites on the aromatic ring portion of compounds of formula (I), (II), (III) or (IV) can be susceptible to various metabolic reactions, therefore incorporation of appropriate substituents on the aromatic ring structures, such as, by way of example only, halogens can reduce, minimize or eliminate this metabolic pathway.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent.

The compounds in Examples are shown in Table 1. Non-limiting examples of synthetic schemes for the preparation of compounds of formula (II) are described in Scheme I. Non-limiting examples of synthetic schemes for the preparation of compounds of formula (III) are described in Scheme II. Non-limiting examples of synthetic schemes for the preparation of compounds of formula (IV) are described in Scheme III.

TABLE 1

Structures of compounds in Examples

| Compounds in Examples | Structures of compounds |
|---|---|
| Compound 1 | 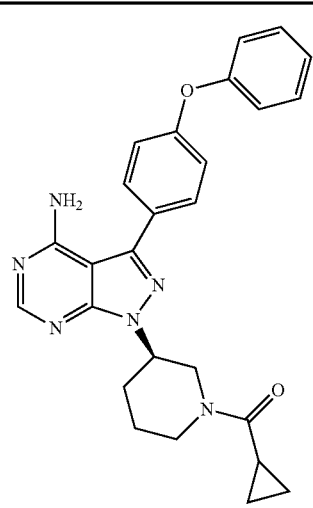 |

TABLE 1-continued
Structures of compounds in Examples
| Compounds in Examples | Structures of compounds |
|---|---|
| Compound 2 | 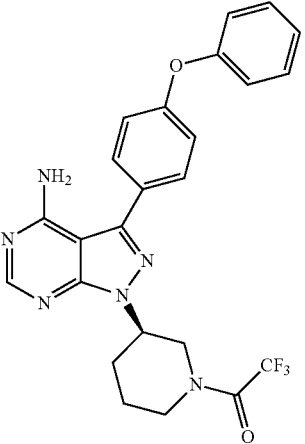 [SMILES: Nc1ncnc2c1c(-c1ccc(Oc3ccccc3)cc1)nn2[C@@H]1CCCN(C(=O)C(F)(F)F)C1] |
| Compound 3 | 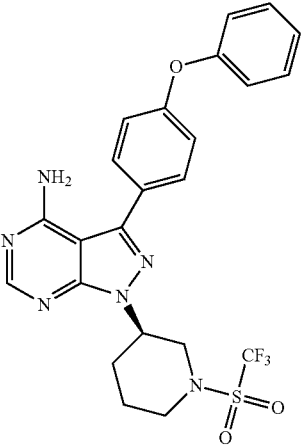 [SMILES: Nc1ncnc2c1c(-c1ccc(Oc3ccccc3)cc1)nn2[C@@H]1CCCN(S(=O)(=O)C(F)(F)F)C1] |
| Compound 4 | 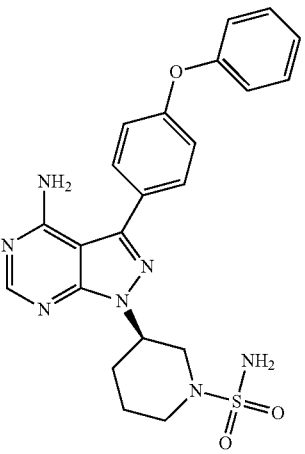 [SMILES: Nc1ncnc2c1c(-c1ccc(Oc3ccccc3)cc1)nn2[C@@H]1CCCN(S(N)(=O)=O)C1] |

TABLE 1-continued

Structures of compounds in Examples

| Compounds in Examples | Structures of compounds |
|---|---|
| Compound 5 | |
| Compound 6 | |
| Compound 7 | |

TABLE 1-continued
Structures of compounds in Examples
| Compounds in Examples | Structures of compounds |
|---|---|
| Compound 8 | 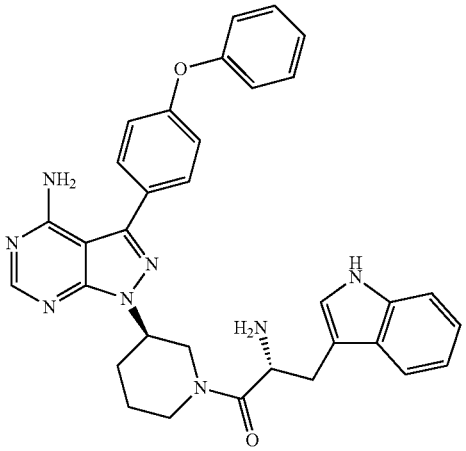 [SMILES: Nc1ncnc2c1c(-c1ccc(Oc3ccccc3)cc1)nn2[C@@H]1CCCN(C(=O)[C@H](N)Cc2c[nH]c3ccccc23)C1] |
| Compound 9 | 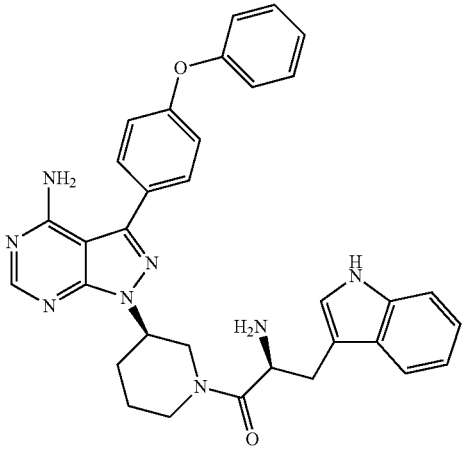 [SMILES: Nc1ncnc2c1c(-c1ccc(Oc3ccccc3)cc1)nn2[C@@H]1CCCN(C(=O)[C@@H](N)Cc2c[nH]c3ccccc23)C1] |
| Compound 10 | 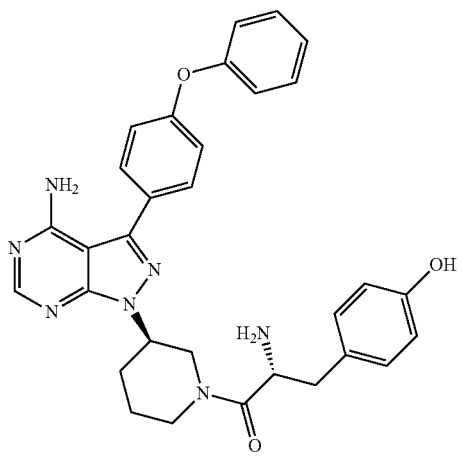 [SMILES: Nc1ncnc2c1c(-c1ccc(Oc3ccccc3)cc1)nn2[C@@H]1CCCN(C(=O)[C@H](N)Cc2ccc(O)cc2)C1] |

TABLE 1-continued
Structures of compounds in Examples
| Compounds in Examples | Structures of compounds |
|---|---|
| Compound 11 | 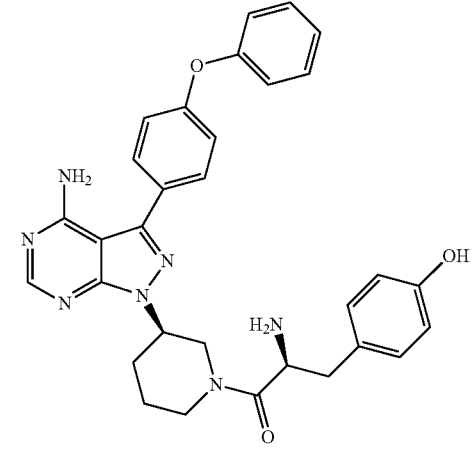 [SMILES: Nc1ncnc2c1c(-c1ccc(Oc3ccccc3)cc1)nn2[C@@H]1CCCN(C(=O)[C@@H](N)Cc2ccc(O)cc2)C1] |
| Compound 12 | 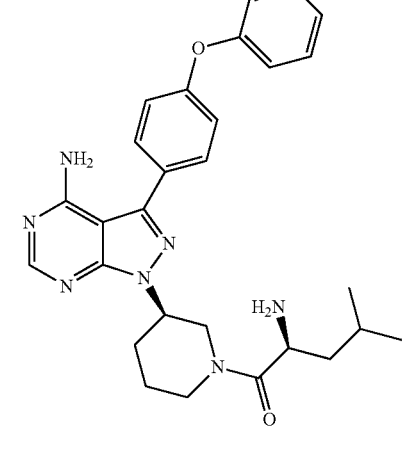 |
| Compound 13 | 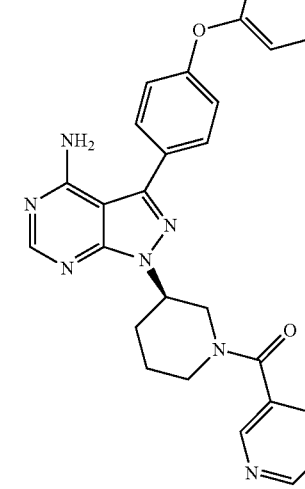 |

TABLE 1-continued
Structures of compounds in Examples
| Compounds in Examples | Structures of compounds |
|---|---|
| Compound 14 | 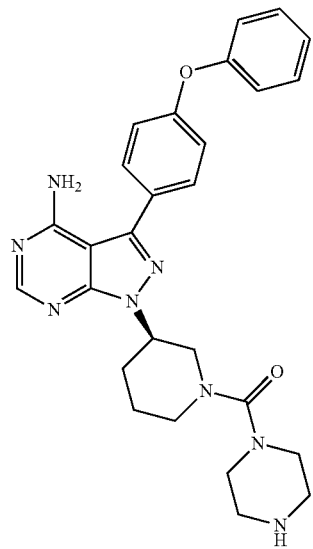 [SMILES: Nc1ncnc2c1c(-c1ccc(Oc3ccccc3)cc1)nn2[C@@H]1CCCN(C(=O)N2CCNCC2)C1] |
| Compound 15 | 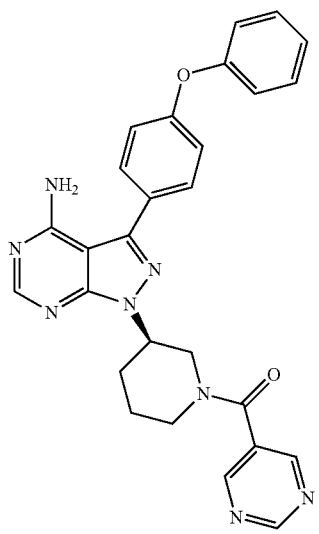 [SMILES: Nc1ncnc2c1c(-c1ccc(Oc3ccccc3)cc1)nn2[C@@H]1CCCN(C(=O)c2cncnc2)C1] |

TABLE 1-continued
Structures of compounds in Examples
| Compounds in Examples | Structures of compounds |
|---|---|
| Compound 16 | 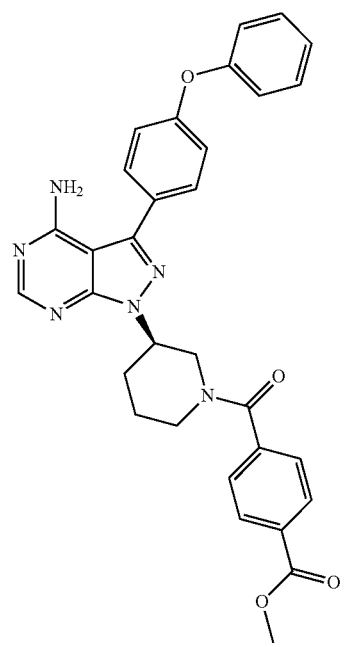 [SMILES: COC(=O)c1ccc(C(=O)N2CCC[C@@H](n3nc(-c4ccc(Oc5ccccc5)cc4)c4c(N)ncnc43)C2)cc1] |
| Compound 17 | 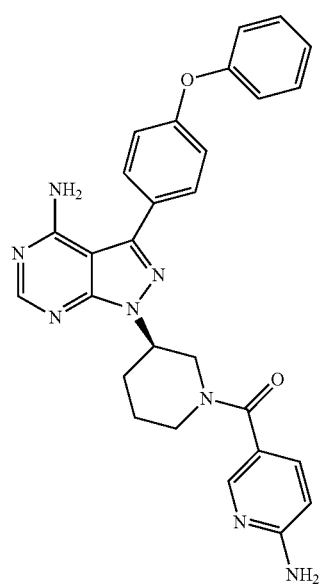 [SMILES: Nc1ccc(C(=O)N2CCC[C@@H](n3nc(-c4ccc(Oc5ccccc5)cc4)c4c(N)ncnc43)C2)cn1] |

TABLE 1-continued
Structures of compounds in Examples
| Compounds in Examples | Structures of compounds |
|---|---|
| Compound 18 | 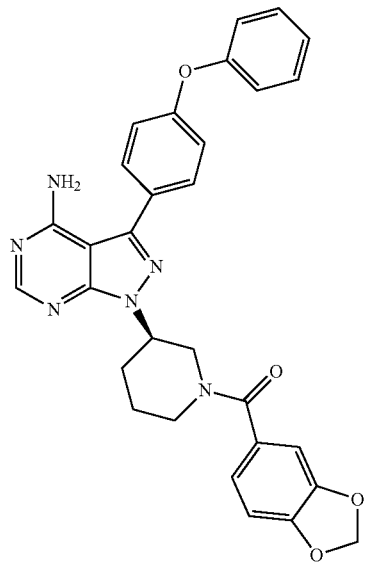 [SMILES: Nc1ncnc2c1c(-c1ccc(Oc3ccccc3)cc1)nn2[C@@H]1CCCN(C(=O)c2ccc3c(c2)OCO3)C1] |
| Compound 19 | 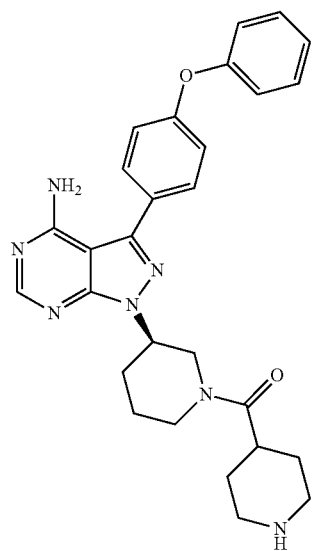 |

TABLE 1-continued

Structures of compounds in Examples

| Compounds in Examples | Structures of compounds |
|---|---|
| Compound 20 | 3-(4-phenoxyphenyl)-1-[(3R)-1-(cyanoacetyl)piperidin-3-yl]-1H-pyrazolo[3,4-d]pyrimidin-4-amine |
| Compound 21 | 3-(4-phenoxyphenyl)-1-[(3R)-1-(2-aminopyrimidine-5-carbonyl)piperidin-3-yl]-1H-pyrazolo[3,4-d]pyrimidin-4-amine |
| Compound 22 | 3-(4-phenoxyphenyl)-1-[(3R)-1-(2-(dimethylamino)acetyl)piperidin-3-yl]-1H-pyrazolo[3,4-d]pyrimidin-4-amine |

TABLE 1-continued

Structures of compounds in Examples

| Compounds in Examples | Structures of compounds |
|---|---|
| Compound 23 | |
| Compound 24 | |
| Compound 25 | |

TABLE 1-continued
Structures of compounds in Examples
| Compounds in Examples | Structures of compounds |
|---|---|
| Compound 26 | 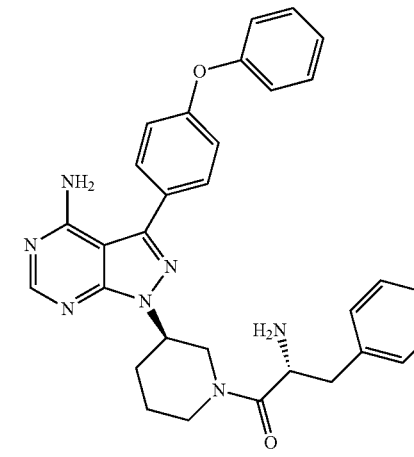 |
| Compound 27 | 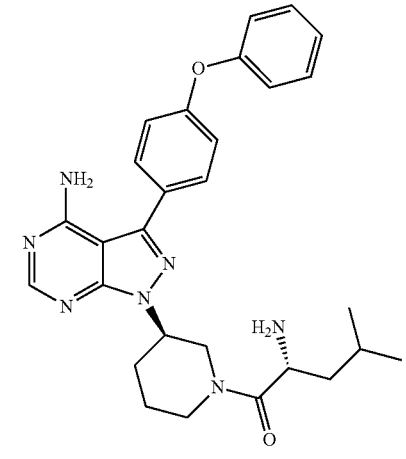 [SMILES: CC(C)C[C@@H](N)C(=O)N1CCC[C@@H](n2nc(-c3ccc(Oc4ccccc4)cc3)c3c(N)ncnc32)C1] |
| Compound 28 | 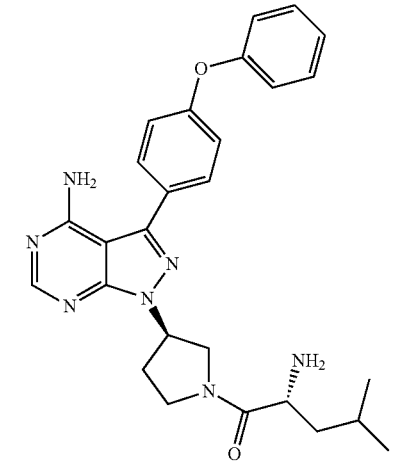 [SMILES: CC(C)C[C@@H](N)C(=O)N1CC[C@@H](n2nc(-c3ccc(Oc4ccccc4)cc3)c3c(N)ncnc32)C1] |

TABLE 1-continued

Structures of compounds in Examples

| Compounds in Examples | Structures of compounds |
|---|---|
| Compound 29 | (structure) |
| Compound 30 | (structure) |
| Compound 31 | (structure) |

TABLE 1-continued
Structures of compounds in Examples
| Compounds in Examples | Structures of compounds |
|---|---|
| Compound 32 | 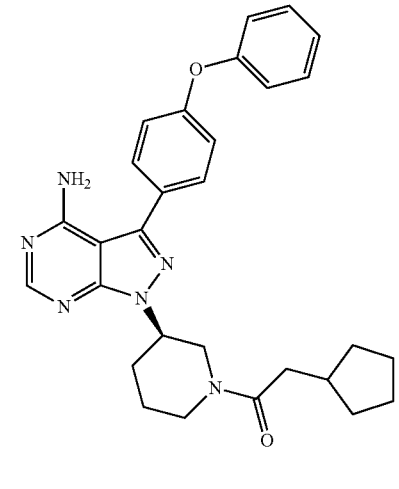 [SMILES: Nc1ncnc2c1c(-c1ccc(Oc3ccccc3)cc1)nn2[C@@H]1CCCN(C(=O)CC2CCCC2)C1] |
| Compound 33 | 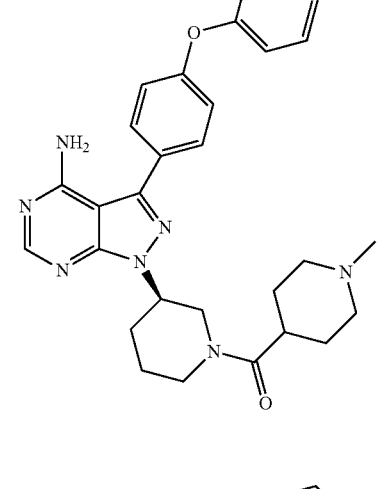 |
| Compound 34 | 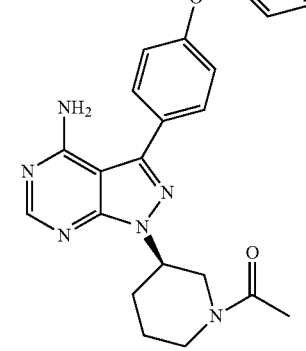 |

TABLE 1-continued

Structures of compounds in Examples

| Compounds in Examples | Structures of compounds |
|---|---|
| Compound 35 | |
| Compound 36 | |
| Compound 37 | |

TABLE 1-continued
Structures of compounds in Examples
| Compounds in Examples | Structures of compounds |
|---|---|
| Compound 38 | 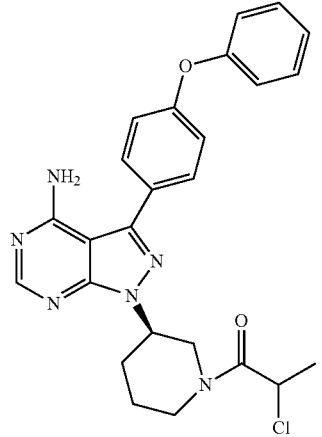 [SMILES: CC(Cl)C(=O)N1CCC[C@@H](n2nc(-c3ccc(Oc4ccccc4)cc3)c3c(N)ncnc32)C1] |
| Compound 39 | 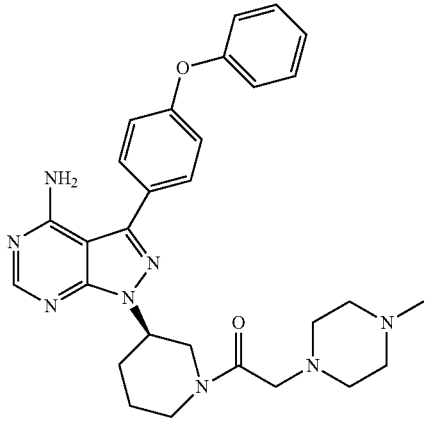 [SMILES: CN1CCN(CC(=O)N2CCC[C@@H](n3nc(-c4ccc(Oc5ccccc5)cc4)c4c(N)ncnc43)C2)CC1] |
| Compound 40 | 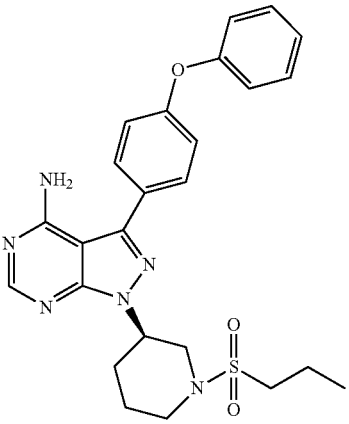 [SMILES: CCCS(=O)(=O)N1CCC[C@@H](n2nc(-c3ccc(Oc4ccccc4)cc3)c3c(N)ncnc32)C1] |

TABLE 1-continued
Structures of compounds in Examples
| Compounds in Examples | Structures of compounds |
|---|---|
| Compound 41 | 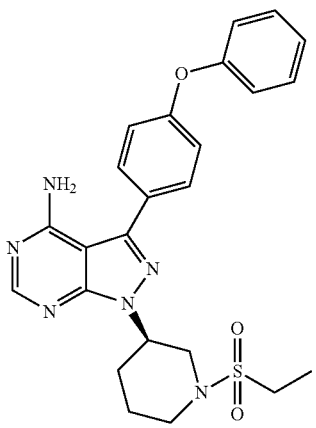 [SMILES: CCS(=O)(=O)N1CCC[C@@H](n2nc(-c3ccc(Oc4ccccc4)cc3)c3c(N)ncnc32)C1] |
| Compound 42 | 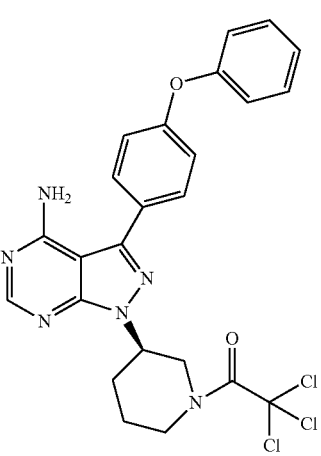 [SMILES: Nc1ncnc2c1c(-c1ccc(Oc3ccccc3)cc1)nn2[C@@H]1CCCN(C(=O)C(Cl)(Cl)Cl)C1] |
| Compound 43 | 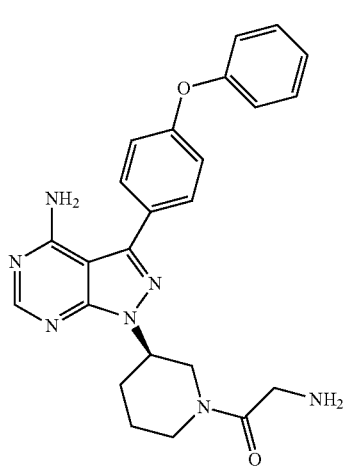 [SMILES: NCC(=O)N1CCC[C@@H](n2nc(-c3ccc(Oc4ccccc4)cc3)c3c(N)ncnc32)C1] |

TABLE 1-continued

Structures of compounds in Examples

| Compounds in Examples | Structures of compounds |
|---|---|
| Compound 44 | (structure: 4-amino-3-(4-phenoxyphenyl)-1H-pyrazolo[3,4-d]pyrimidine linked to piperidine N-acylated with 2-amino-3-hydroxybutanoyl group) |
| Compound 45 | (structure: 4-amino-3-(4-phenoxyphenyl)-1H-pyrazolo[3,4-d]pyrimidine linked to piperidine N-acylated with 2-amino-3-methylbutanoyl (valyl) group) |
| Compound 46 | (structure: 4-amino-3-(4-phenoxyphenyl)-1H-pyrazolo[3,4-d]pyrimidine linked to piperidine N-acylated with 3-aminopropanoyl (β-alanyl) group) |

TABLE 1-continued
Structures of compounds in Examples
| Compounds in Examples | Structures of compounds |
|---|---|
| Compound 47 | 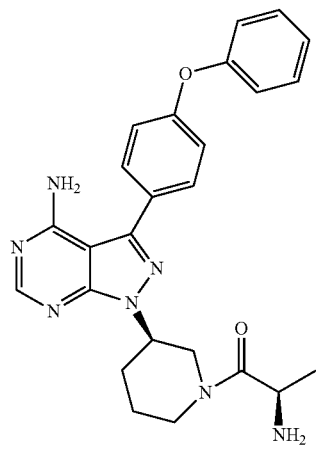 [SMILES: C[C@@H](N)C(=O)N1CCC[C@@H](n2nc(-c3ccc(Oc4ccccc4)cc3)c3c(N)ncnc32)C1] |
| Compound 48 | 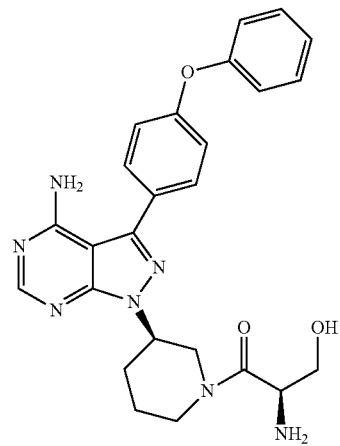 [SMILES: Nc1ncnc2c1c(-c1ccc(Oc3ccccc3)cc1)nn2[C@@H]1CCCN(C(=O)[C@H](N)CO)C1] |
| Compound 49 | 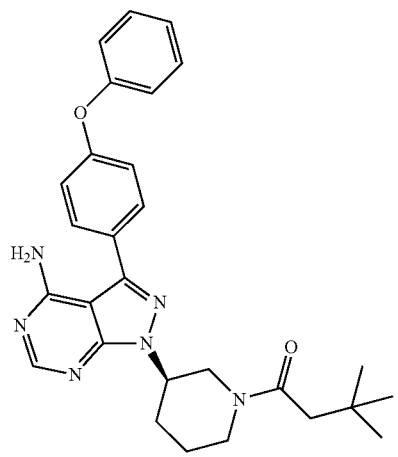 [SMILES: CC(C)(C)CC(=O)N1CCC[C@@H](n2nc(-c3ccc(Oc4ccccc4)cc3)c3c(N)ncnc32)C1] |

TABLE 1-continued
Structures of compounds in Examples
| Compounds in Examples | Structures of compounds |
|---|---|
| Compound 50 | 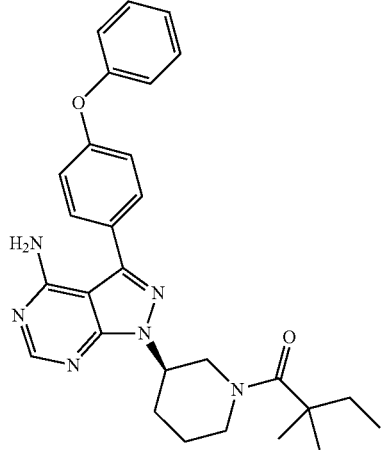 [SMILES: CCC(C)(C)C(=O)N1CCC[C@@H](n2nc(-c3ccc(Oc4ccccc4)cc3)c3c(N)ncnc32)C1] |
| Compound 51 | 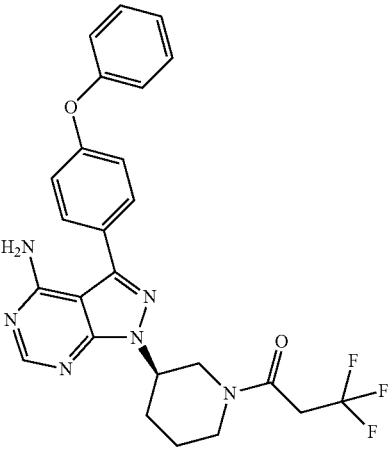 [SMILES: Nc1ncnc2c1c(-c1ccc(Oc3ccccc3)cc1)nn2[C@@H]1CCCN(C(=O)CC(F)(F)F)C1] |
| Compound 52 | 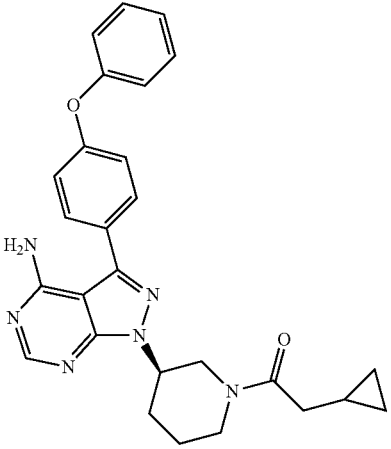 [SMILES: Nc1ncnc2c1c(-c1ccc(Oc3ccccc3)cc1)nn2[C@@H]1CCCN(C(=O)CC2CC2)C1] |

TABLE 1-continued
Structures of compounds in Examples
| Compounds in Examples | Structures of compounds |
|---|---|
| Compound 53 | 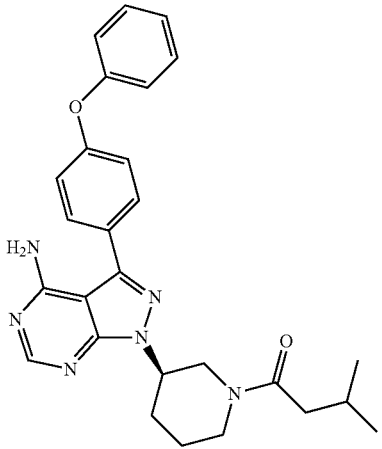 [SMILES: CC(C)CC(=O)N1CCC[C@@H](n2nc(-c3ccc(Oc4ccccc4)cc3)c3c(N)ncnc32)C1] |
| Compound 54 | 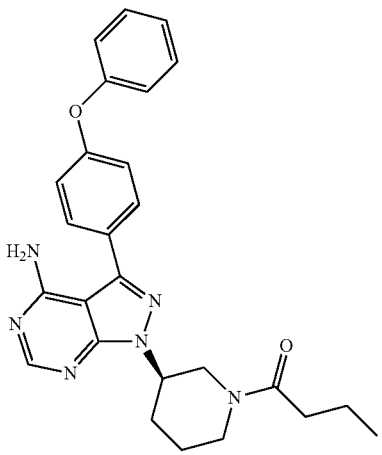 [SMILES: CCCC(=O)N1CCC[C@@H](n2nc(-c3ccc(Oc4ccccc4)cc3)c3c(N)ncnc32)C1] |
| Compound 55 | 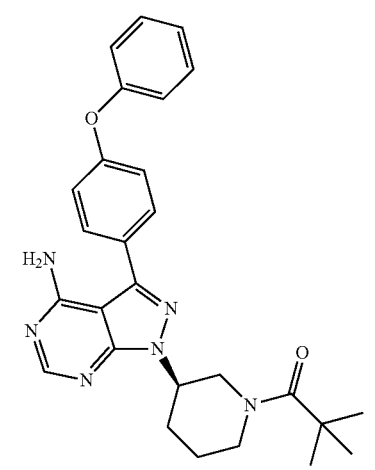 [SMILES: CC(C)(C)C(=O)N1CCC[C@@H](n2nc(-c3ccc(Oc4ccccc4)cc3)c3c(N)ncnc32)C1] |

TABLE 1-continued
Structures of compounds in Examples
| Compounds in Examples | Structures of compounds |
|---|---|
| Compound 56 | 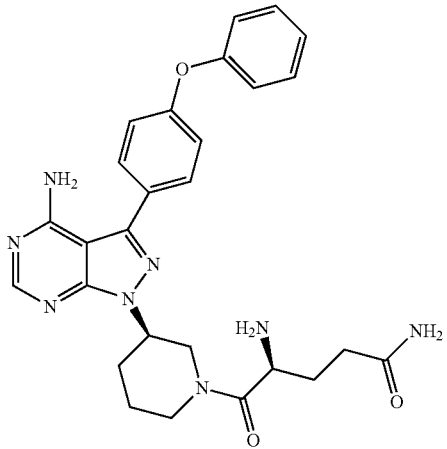 [SMILES: NC(=O)CC[C@H](N)C(=O)N1CCC[C@@H](n2nc(-c3ccc(Oc4ccccc4)cc3)c3c(N)ncnc32)C1] |
| Compound 57 | 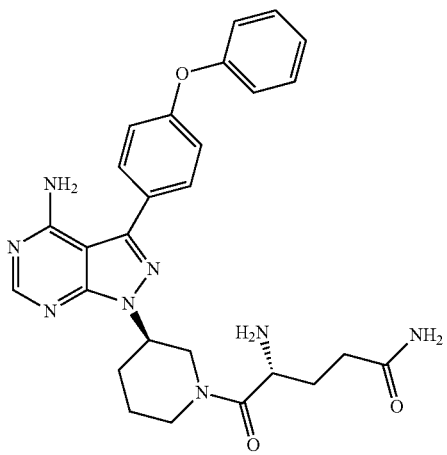 [SMILES: NC(=O)CC[C@@H](N)C(=O)N1CCC[C@@H](n2nc(-c3ccc(Oc4ccccc4)cc3)c3c(N)ncnc32)C1] |
| Compound 58 | 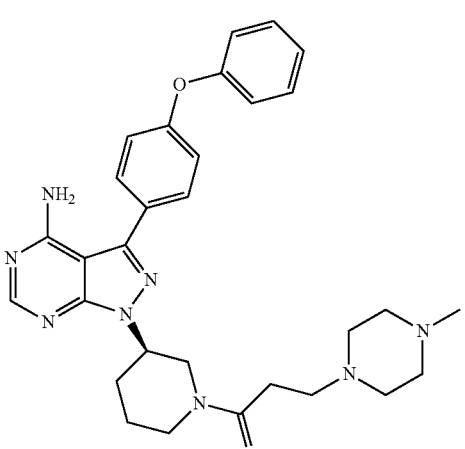 |

TABLE 1-continued
Structures of compounds in Examples
| Compounds in Examples | Structures of compounds |
|---|---|
| Compound 59 | 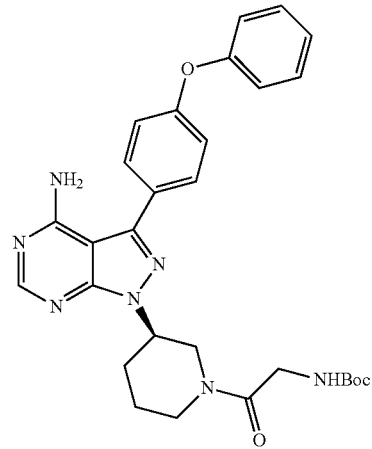 [SMILES: CC(C)(C)OC(=O)NCC(=O)N1CCC[C@@H](n2nc(-c3ccc(Oc4ccccc4)cc3)c3c(N)ncnc32)C1] |
| Compound 60 | 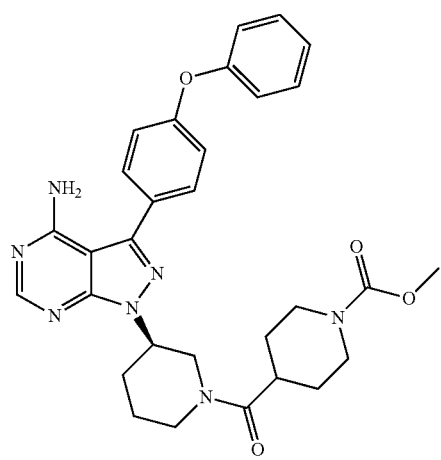 [SMILES: COC(=O)N1CCC(C(=O)N2CCC[C@@H](n3nc(-c4ccc(Oc5ccccc5)cc4)c4c(N)ncnc43)C2)CC1] |
| Compound 61 | 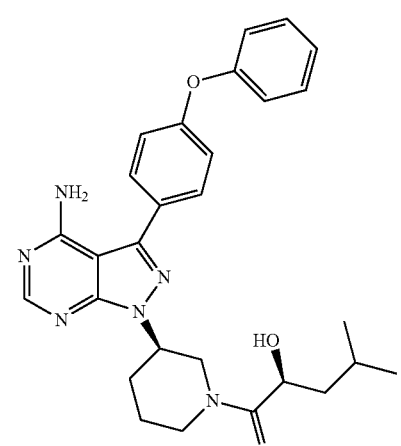 |

TABLE 1-continued

Structures of compounds in Examples

| Compounds in Examples | Structures of compounds |
|---|---|
| Compound 62 | |
| Compound 63 | |
| Compound 64 | |

TABLE 1-continued
Structures of compounds in Examples
| Compounds in Examples | Structures of compounds |
|---|---|
| Compound 65 | 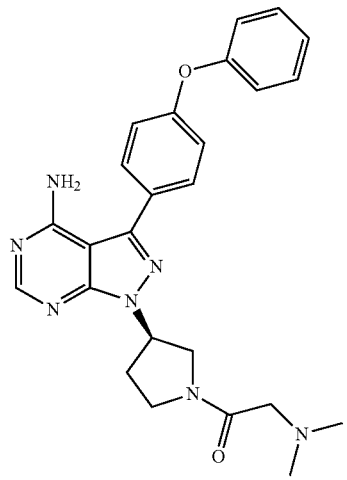 [SMILES: CN(C)CC(=O)N1CC[C@@H](n2nc(-c3ccc(Oc4ccccc4)cc3)c3c(N)ncnc32)C1] |
| Compound 66 | 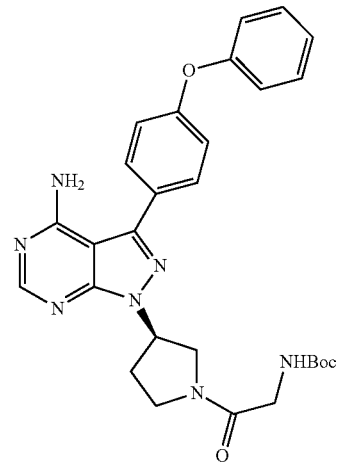 [SMILES: CC(C)(C)OC(=O)NCC(=O)N1CC[C@@H](n2nc(-c3ccc(Oc4ccccc4)cc3)c3c(N)ncnc32)C1] |
| Compound 67 | 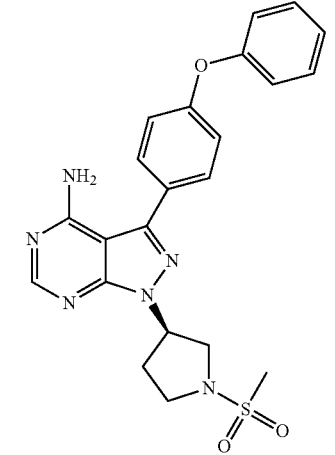 [SMILES: CS(=O)(=O)N1CC[C@@H](n2nc(-c3ccc(Oc4ccccc4)cc3)c3c(N)ncnc32)C1] |

TABLE 1-continued
Structures of compounds in Examples
| Compounds in Examples | Structures of compounds |
|---|---|
| Compound 68 | 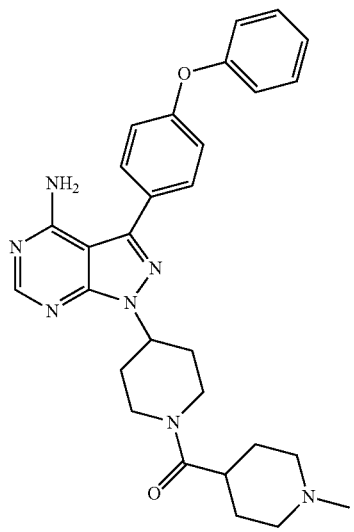 [SMILES: CN1CCC(C(=O)N2CCC(n3nc(-c4ccc(Oc5ccccc5)cc4)c4c(N)ncnc43)CC2)CC1] |
| Compound 69 | 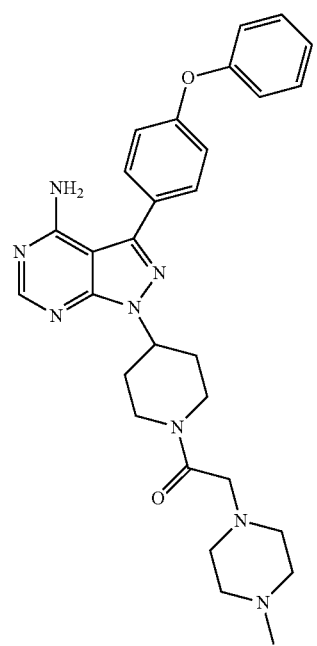 [SMILES: CN1CCN(CC(=O)N2CCC(n3nc(-c4ccc(Oc5ccccc5)cc4)c4c(N)ncnc43)CC2)CC1] |

TABLE 1-continued
Structures of compounds in Examples
| Compounds in Examples | Structures of compounds |
|---|---|
| Compound 70 | 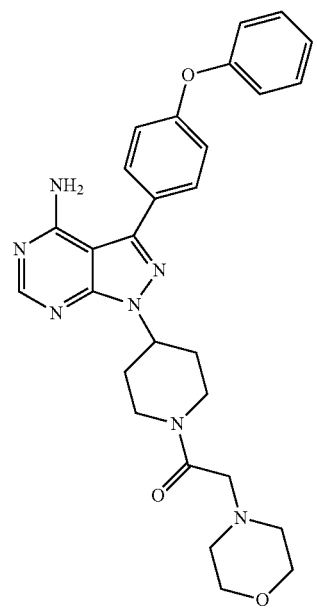 [SMILES: Nc1ncnc2c1c(-c1ccc(Oc3ccccc3)cc1)nn2C1CCN(C(=O)CN2CCOCC2)CC1] |
| Compound 71 | 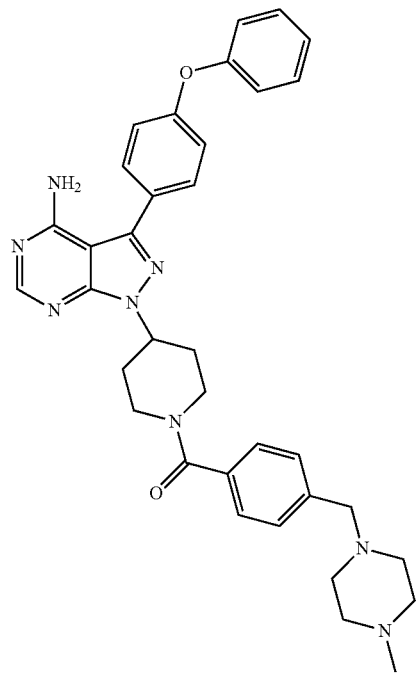 [SMILES: CN1CCN(Cc2ccc(C(=O)N3CCC(n4nc(-c5ccc(Oc6ccccc6)cc5)c5c(N)ncnc54)CC3)cc2)CC1] |

TABLE 1-continued

Structures of compounds in Examples

| Compounds in Examples | Structures of compounds |
|---|---|
| Compound 72 | |
| Compound 73 | |
| Compound 74 | |

TABLE 1-continued
Structures of compounds in Examples
| Compounds in Examples | Structures of compounds |
|---|---|
| Compound 75 | 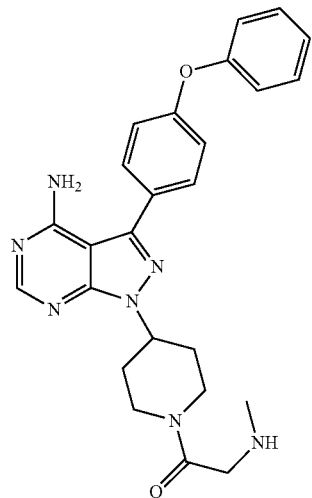 [SMILES: CNCC(=O)N1CCC(n2nc(-c3ccc(Oc4ccccc4)cc3)c3c(N)ncnc32)CC1] |
| Compound 76 | 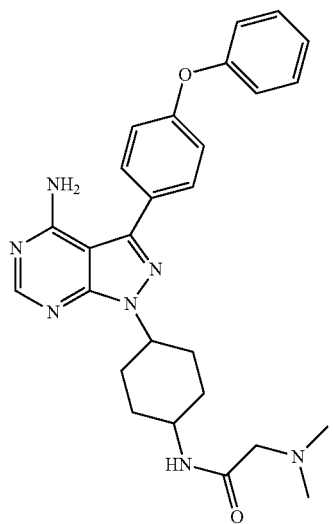 [SMILES: CN(C)CC(=O)NC1CCC(n2nc(-c3ccc(Oc4ccccc4)cc3)c3c(N)ncnc32)CC1] |

TABLE 1-continued
Structures of compounds in Examples
| Compounds in Examples | Structures of compounds |
|---|---|
| Compound 77 | 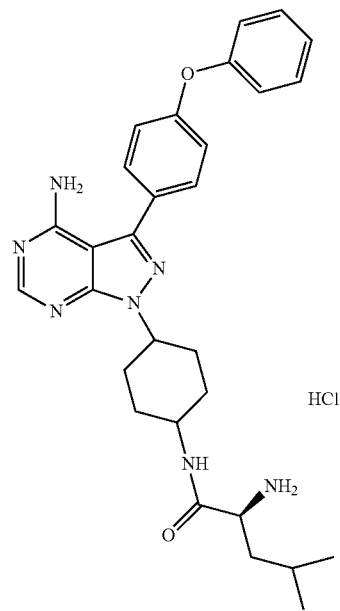 [SMILES: CC(C)C[C@H](N)C(=O)NC1CCC(n2nc(-c3ccc(Oc4ccccc4)cc3)c3c(N)ncnc32)CC1 ; Cl] |
| Compound 78 | 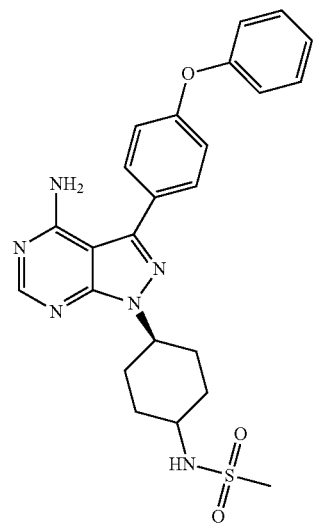 |

TABLE 1-continued
Structures of compounds in Examples
| Compounds in Examples | Structures of compounds |
| --- | --- |
| Compound 79 | 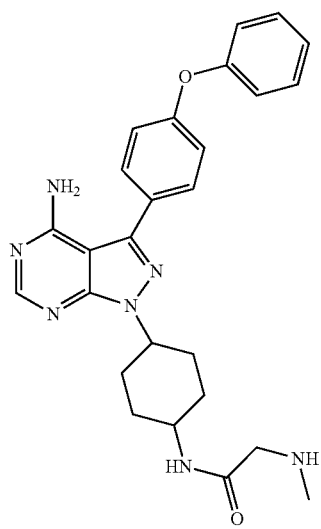 [SMILES: CNCC(=O)NC1CCC(n2nc(-c3ccc(Oc4ccccc4)cc3)c3c(N)ncnc32)CC1] |
| Compound 80 | 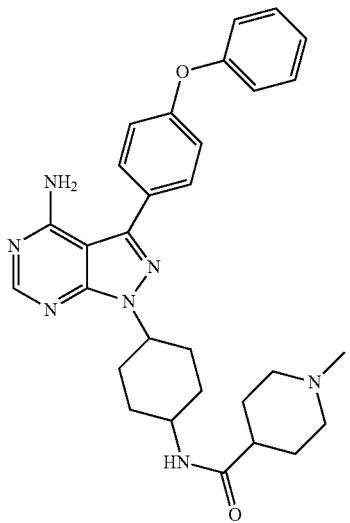 [SMILES: CN1CCC(C(=O)NC2CCC(n3nc(-c4ccc(Oc5ccccc5)cc4)c4c(N)ncnc43)CC2)CC1] |

TABLE 1-continued
Structures of compounds in Examples
| Compounds in Examples | Structures of compounds |
|---|---|
| Compound 81 | 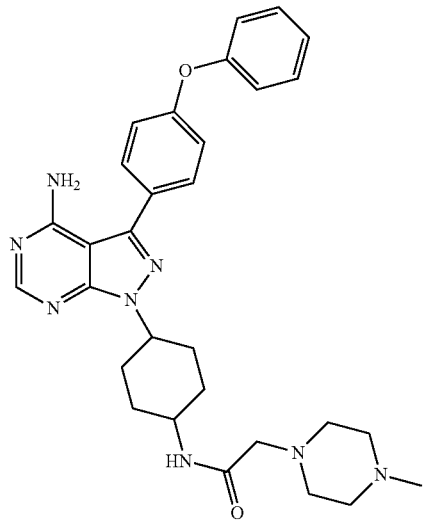 [SMILES: CN1CCN(CC(=O)NC2CCC(n3nc(-c4ccc(Oc5ccccc5)cc4)c4c(N)ncnc43)CC2)CC1] |
| Compound 82 | 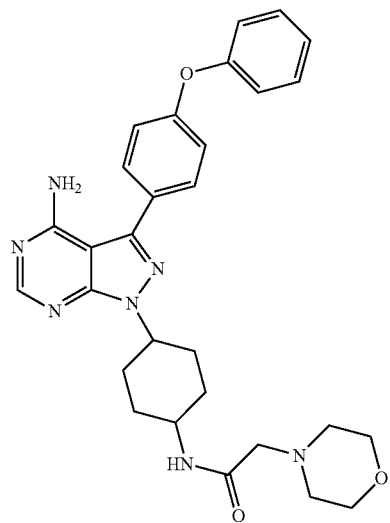 [SMILES: Nc1ncnc2c1c(-c1ccc(Oc3ccccc3)cc1)nn2C1CCC(NC(=O)CN2CCOCC2)CC1] |

TABLE 1-continued
Structures of compounds in Examples
| Compounds in Examples | Structures of compounds |
|---|---|
| Compound 83 | 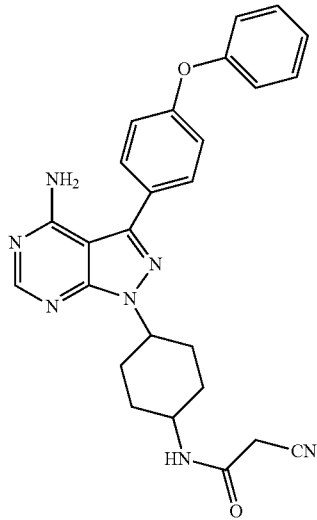 [SMILES: N#CCC(=O)NC1CCC(n2nc(-c3ccc(Oc4ccccc4)cc3)c3c(N)ncnc32)CC1] |
| Compound 84 | 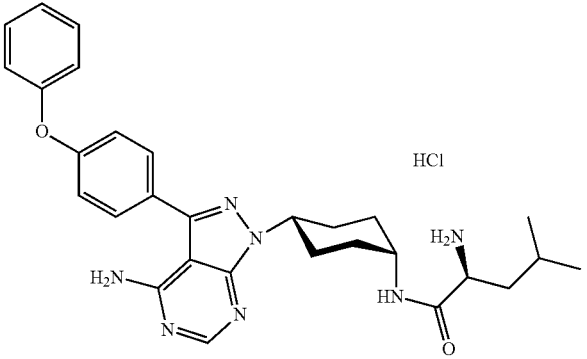 |
| Compound 85 | 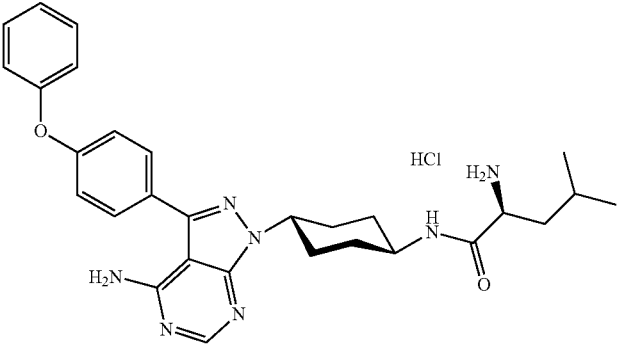 |

TABLE 1-continued
Structures of compounds in Examples
| Compounds in Examples | Structures of compounds |
|---|---|
| Compound 86 | 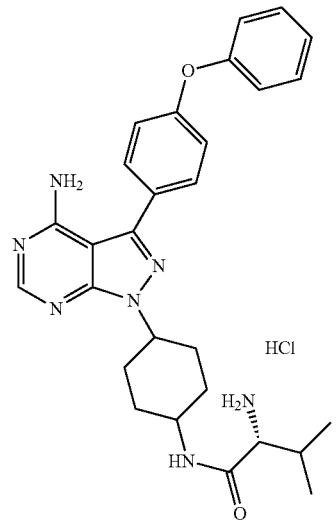 [SMILES: CC(C)[C@@H](N)C(=O)NC1CCC(n2nc(-c3ccc(Oc4ccccc4)cc3)c3c(N)ncnc32)CC1 ; Cl] |
| Compound 87 | 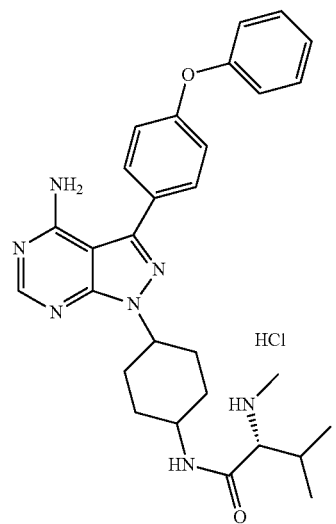 [SMILES: CN[C@@H](C(=O)NC1CCC(n2nc(-c3ccc(Oc4ccccc4)cc3)c3c(N)ncnc32)CC1)C(C)C ; Cl] |

TABLE 1-continued
Structures of compounds in Examples
| Compounds in Examples | Structures of compounds |
|---|---|
| Compound 88 | 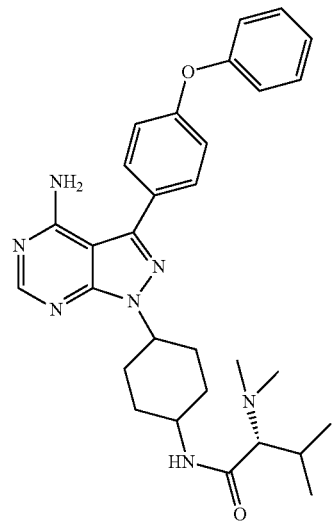 [SMILES: CC(C)[C@H](C(=O)NC1CCC(n2nc(-c3ccc(Oc4ccccc4)cc3)c3c(N)ncnc32)CC1)N(C)C] |
| Compound 89 | 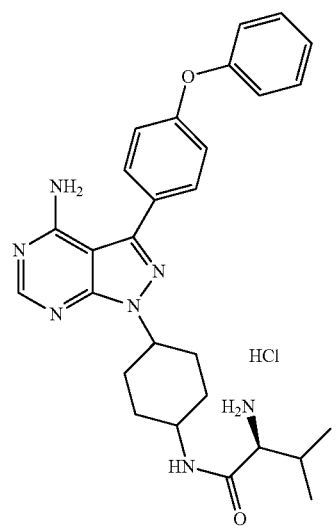 [SMILES: CC(C)[C@H](N)C(=O)NC1CCC(n2nc(-c3ccc(Oc4ccccc4)cc3)c3c(N)ncnc32)CC1 ; Cl] |

TABLE 1-continued
Structures of compounds in Examples
| Compounds in Examples | Structures of compounds |
|---|---|
| Compound 90 | 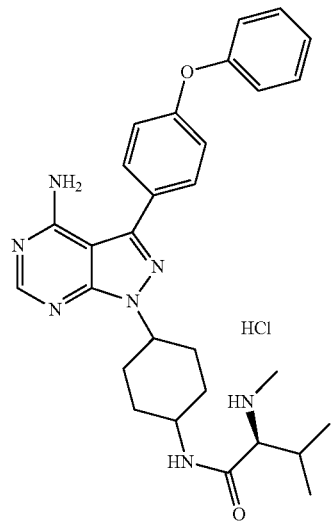 [SMILES: CN[C@H](C(=O)NC1CCC(n2nc(-c3ccc(Oc4ccccc4)cc3)c3c(N)ncnc32)CC1)C(C)C ; Cl] |
| Compound 91 | 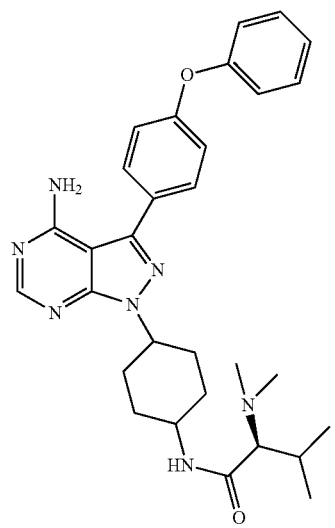 [SMILES: CC(C)[C@@H](C(=O)NC1CCC(n2nc(-c3ccc(Oc4ccccc4)cc3)c3c(N)ncnc32)CC1)N(C)C] |

TABLE 1-continued
Structures of compounds in Examples
| Compounds in Examples | Structures of compounds |
|---|---|
| Compound 92 | 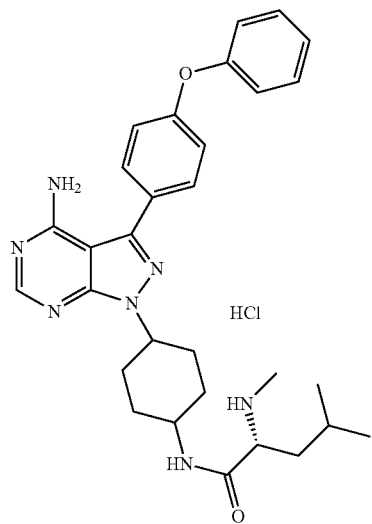 [SMILES: CN[C@H](CC(C)C)C(=O)NC1CCC(n2nc(-c3ccc(Oc4ccccc4)cc3)c3c(N)ncnc32)CC1 ; Cl] HCl |
| Compound 93 | 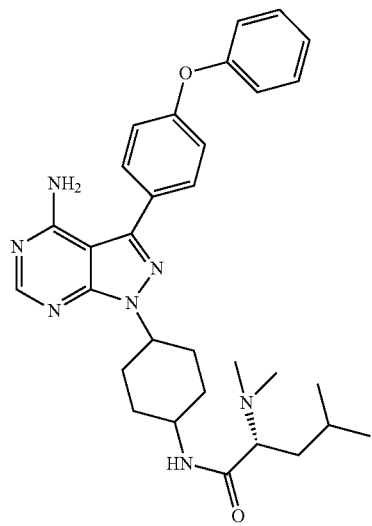 [SMILES: CC(C)C[C@H](C(=O)NC1CCC(n2nc(-c3ccc(Oc4ccccc4)cc3)c3c(N)ncnc32)CC1)N(C)C] |

TABLE 1-continued
Structures of compounds in Examples
| Compounds in Examples | Structures of compounds |
|---|---|
| Compound 94 | 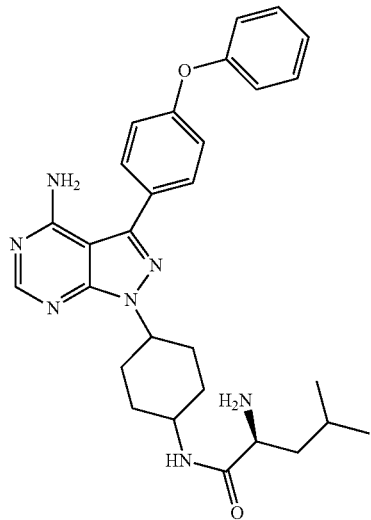 [SMILES: CC(C)C[C@H](N)C(=O)NC1CCC(n2nc(-c3ccc(Oc4ccccc4)cc3)c3c(N)ncnc32)CC1] |
| Compound 95 | 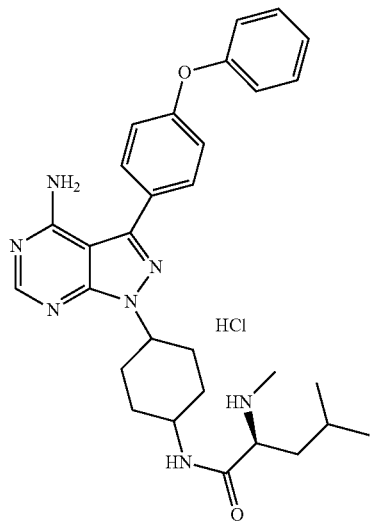 [SMILES: CN[C@@H](CC(C)C)C(=O)NC1CCC(n2nc(-c3ccc(Oc4ccccc4)cc3)c3c(N)ncnc32)CC1 ; Cl] |

TABLE 1-continued
Structures of compounds in Examples
| Compounds in Examples | Structures of compounds |
|---|---|
| Compound 96 | 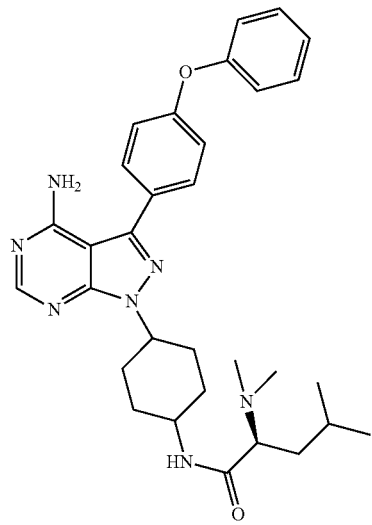 [SMILES: CC(C)C[C@@H](C(=O)NC1CCC(n2nc(-c3ccc(Oc4ccccc4)cc3)c3c(N)ncnc32)CC1)N(C)C] |
| Compound 97 | 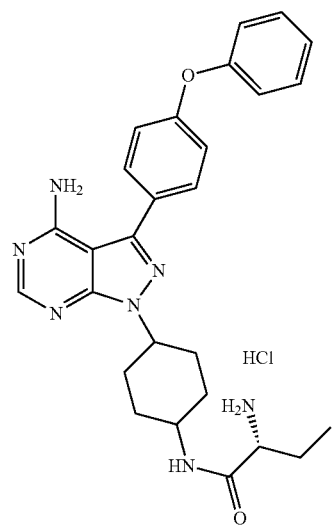 [SMILES: CC[C@@H](N)C(=O)NC1CCC(n2nc(-c3ccc(Oc4ccccc4)cc3)c3c(N)ncnc32)CC1 ; Cl] |

TABLE 1-continued
Structures of compounds in Examples
| Compounds in Examples | Structures of compounds |
|---|---|
| Compound 98 | 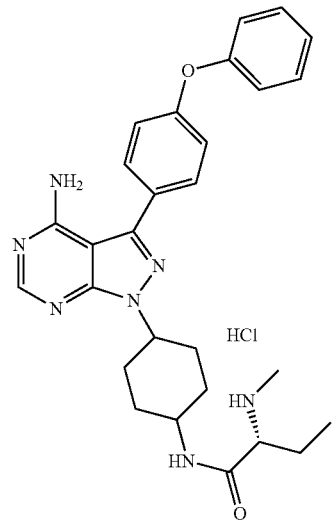 [SMILES: CC[C@@H](NC)C(=O)NC1CCC(n2nc(-c3ccc(Oc4ccccc4)cc3)c3c(N)ncnc32)CC1 ; Cl] |
| Compound 99 | 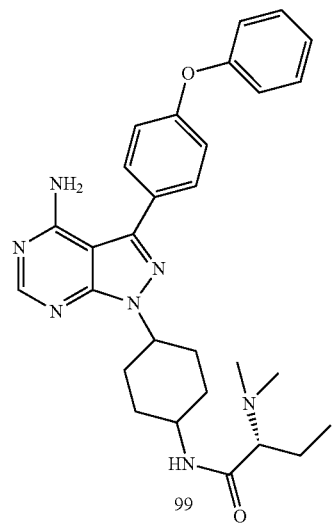 [SMILES: CC[C@H](C(=O)NC1CCC(n2nc(-c3ccc(Oc4ccccc4)cc3)c3c(N)ncnc32)CC1)N(C)C] |

TABLE 1-continued
Structures of compounds in Examples
| Compounds in Examples | Structures of compounds |
|---|---|
| Compound 100 | 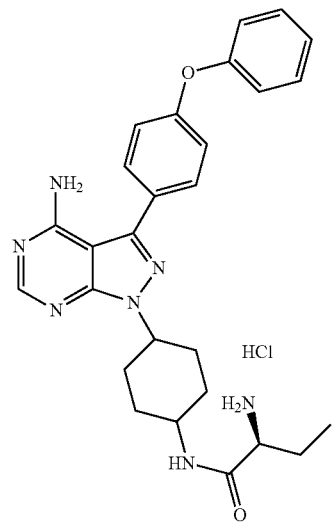 [SMILES: CC[C@H](N)C(=O)NC1CCC(n2nc(-c3ccc(Oc4ccccc4)cc3)c3c(N)ncnc32)CC1 ; Cl] |
| Compound 101 | 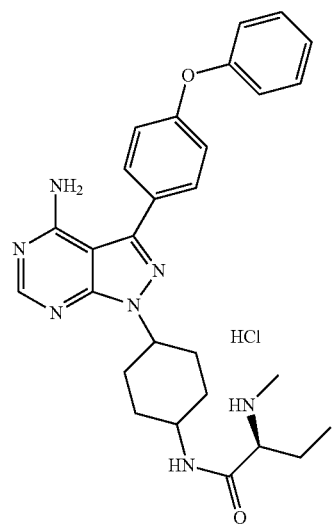 [SMILES: CC[C@H](NC)C(=O)NC1CCC(n2nc(-c3ccc(Oc4ccccc4)cc3)c3c(N)ncnc32)CC1 ; Cl] |

TABLE 1-continued
Structures of compounds in Examples
| Compounds in Examples | Structures of compounds |
|---|---|
| Compound 102 | 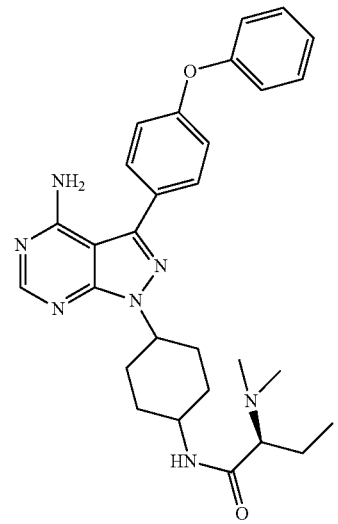 [SMILES: CC[C@@H](C(=O)NC1CCC(n2nc(-c3ccc(Oc4ccccc4)cc3)c3c(N)ncnc32)CC1)N(C)C] |
| Compound 103 | 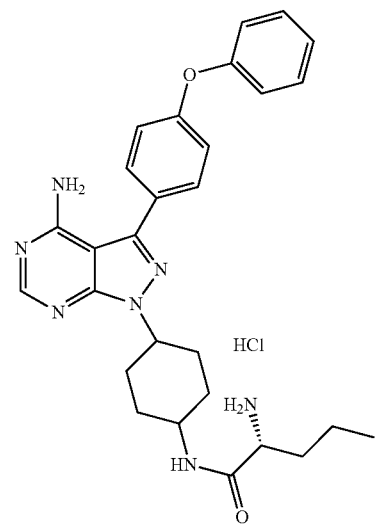 [SMILES: CCC[C@@H](N)C(=O)NC1CCC(n2nc(-c3ccc(Oc4ccccc4)cc3)c3c(N)ncnc32)CC1 ; Cl] |

TABLE 1-continued
Structures of compounds in Examples
| Compounds in Examples | Structures of compounds |
|---|---|
| Compound 104 | 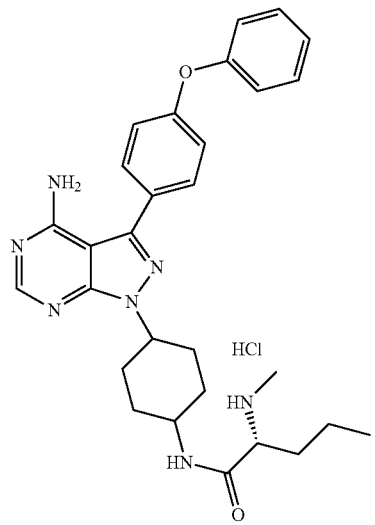 [SMILES: CCC[C@@H](NC)C(=O)NC1CCC(n2nc(-c3ccc(Oc4ccccc4)cc3)c3c(N)ncnc32)CC1 ; Cl] |
| Compound 105 | 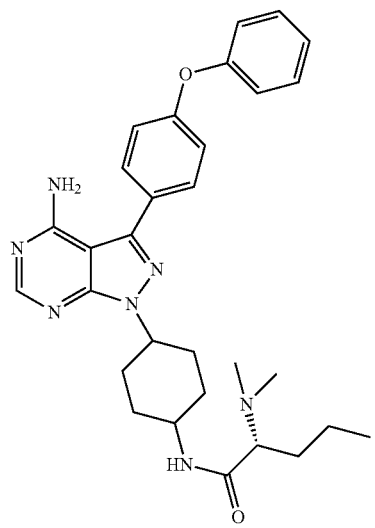 |

TABLE 1-continued
Structures of compounds in Examples
| Compounds in Examples | Structures of compounds |
|---|---|
| Compound 106 | 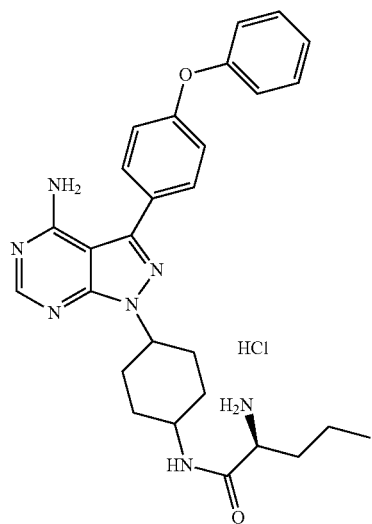 [SMILES: CCC[C@H](N)C(=O)NC1CCC(n2nc(-c3ccc(Oc4ccccc4)cc3)c3c(N)ncnc32)CC1 ; Cl] |
| Compound 107 | 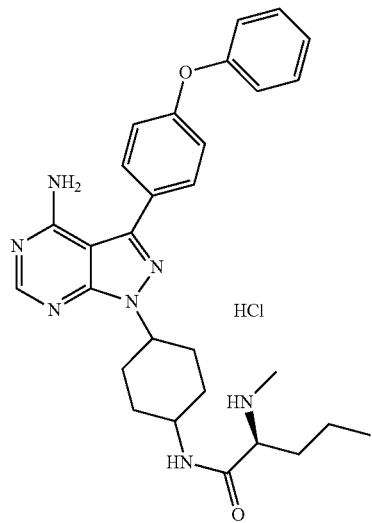 [SMILES: CCC[C@H](NC)C(=O)NC1CCC(n2nc(-c3ccc(Oc4ccccc4)cc3)c3c(N)ncnc32)CC1 ; Cl] |

TABLE 1-continued
Structures of compounds in Examples
| Compounds in Examples | Structures of compounds |
| --- | --- |
| Compound 108 | 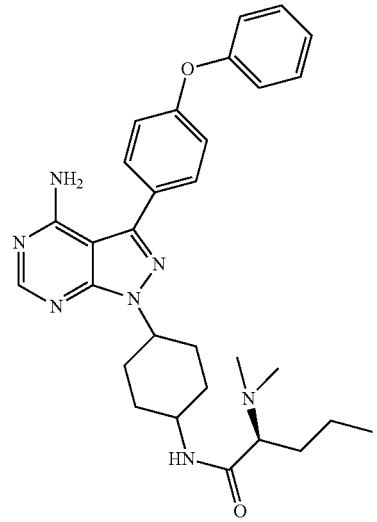 |
| Compound 109 | 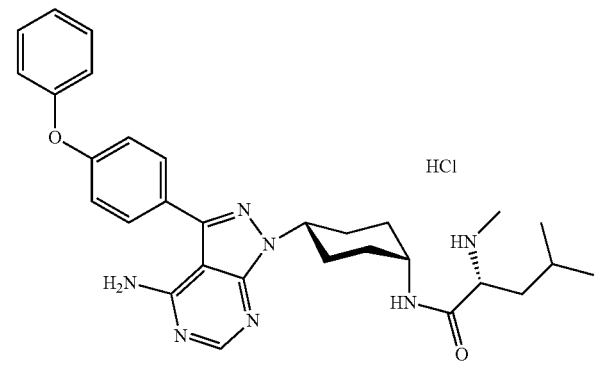 |
| Compound 110 | 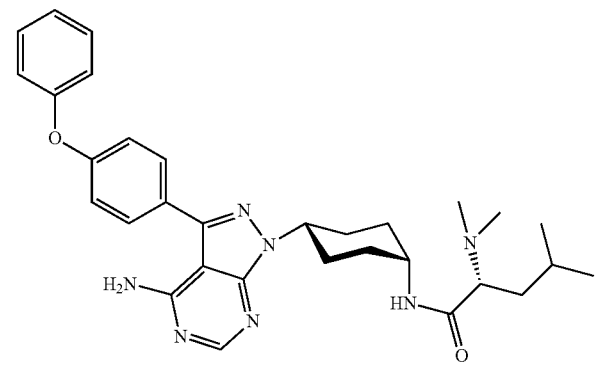 |

TABLE 1-continued
Structures of compounds in Examples
| Compounds in Examples | Structures of compounds |
|---|---|
| Compound 111 | 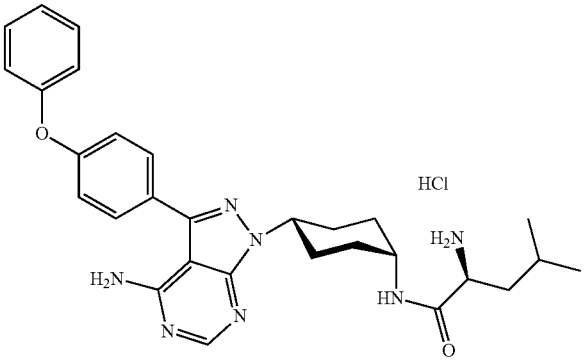 |
| Compound 112 | 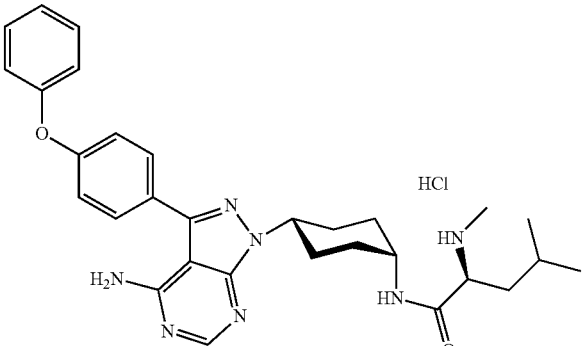 |
| Compound 113 | 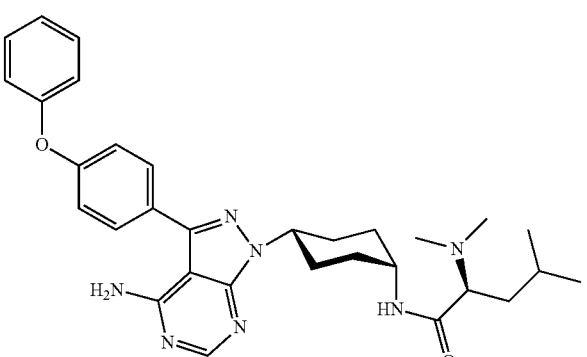 |
| Compound 114 | 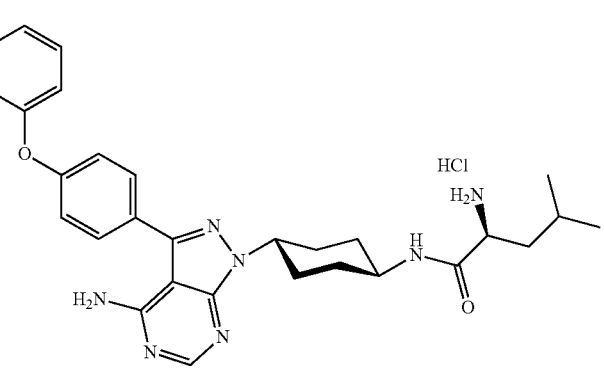 |

TABLE 1-continued
Structures of compounds in Examples
| Compounds in Examples | Structures of compounds |
|---|---|
| Compound 115 | 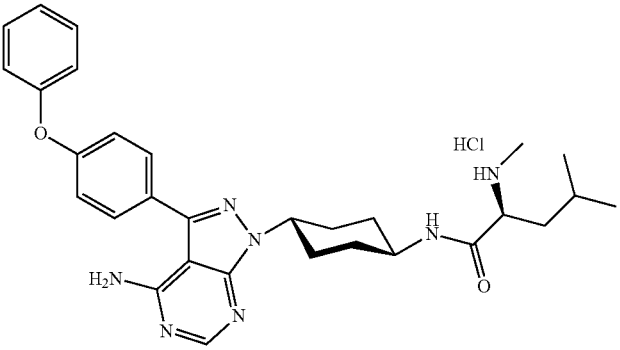 |
| Compound 116 | 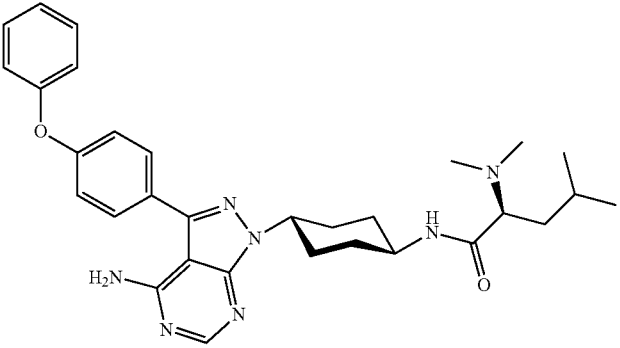 |
| Compound 117 | 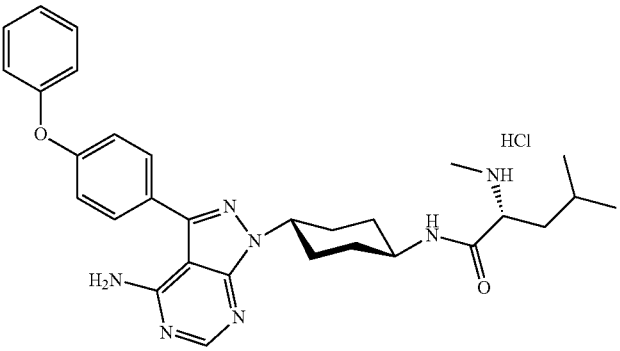 |
| Compound 118 | 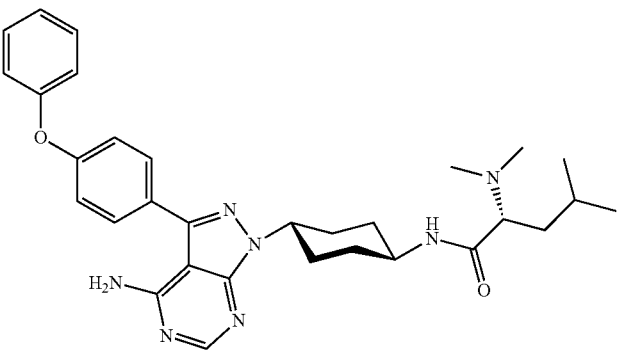 |

TABLE 1-continued
Structures of compounds in Examples
| Compounds in Examples | Structures of compounds |
|---|---|
| Compound 119 | 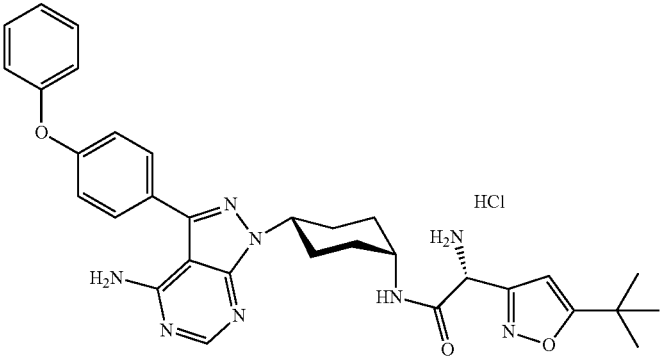 |
| Compound 120 | 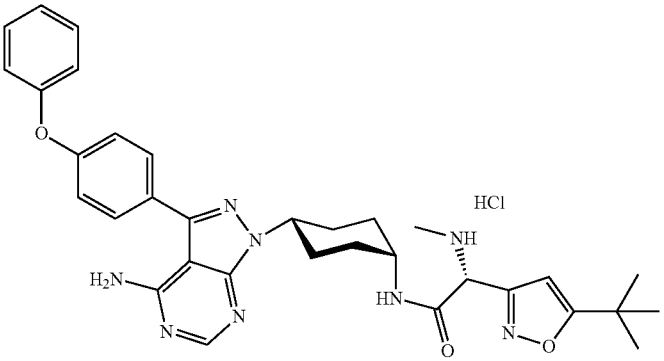 |
| Compound 121 | 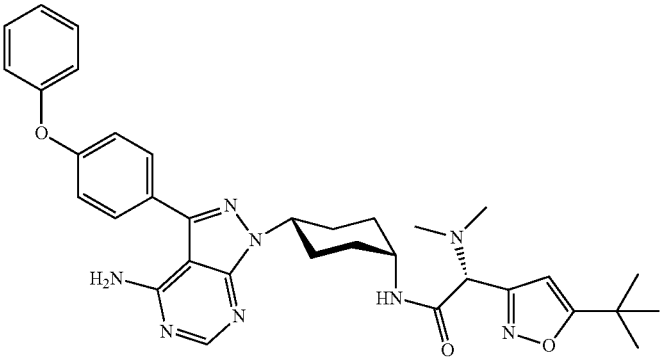 |
| Compound 122 | 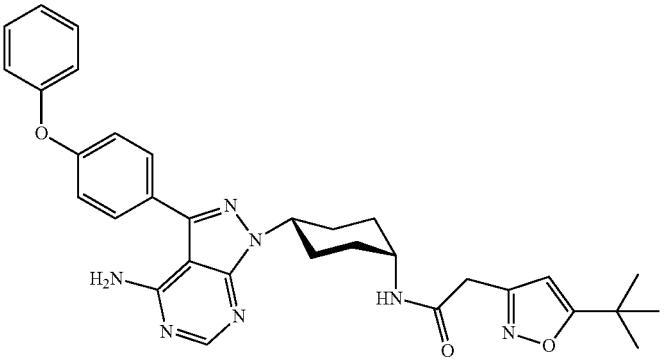 |

TABLE 1-continued

Structures of compounds in Examples

| Compounds in Examples | Structures of compounds |
|---|---|
| Compound 123 | |
| Compound 124 | |
| Compound 125 | |
| Compound 126 | |

Scheme I

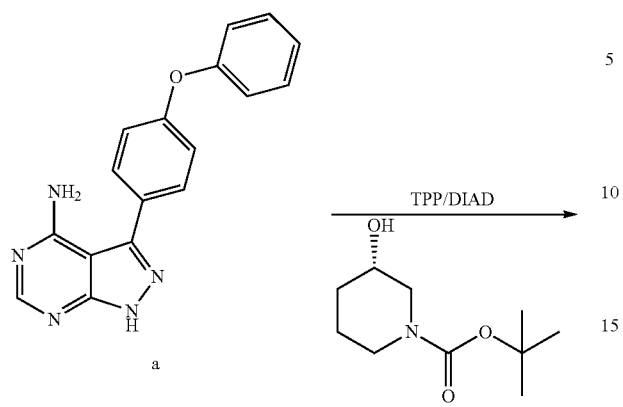

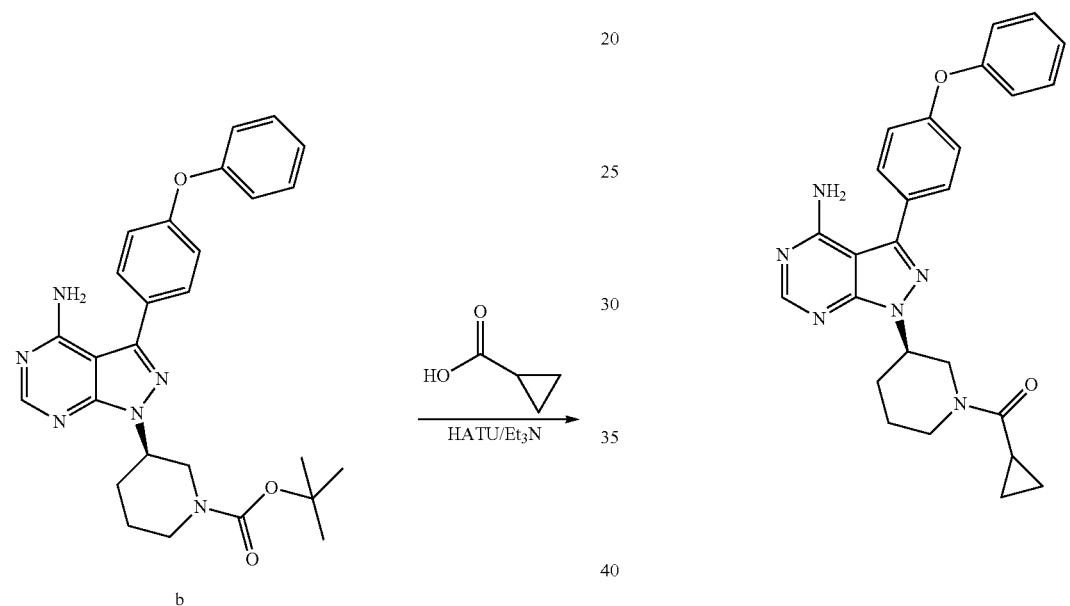

Example 1

Synthesis of Compound 1

(R)-(3-(4-amino-(4-phenoxyphenyl)-1H-pyrazolo[3,4-d]pyrimidin-1-yl)piperidin-1-yl)(cyclopropyl)methanone As shown in Scheme I, b was synthesized by using a, wherein a may be prepared by a method known in the art or commercially available. In the synthesis of b from a, (S)-N-tert-butoxycarbonyl-3-piperidinol was used to obtain the intermediate b in R configuration. The intermediate b (0.1 g) was treated with 4N HCl in dioxane (1 ml) and was stirred at room temperature for 1 hour, and then was concentrated to a dry product of 0.08 g, which was dissolved in 4 ml of dichloromethane, and diisopropylethylamine (0.2 ml), cyclopropanecarboxylic acid (0.03 g), 2-(7-azobenzotriazole)-N,N,N',N'-tetramethyluronium hexafluorophosphate HATU (0.15 g) were subsequently added, the mixture was stirred at room temperature for 30 minutes, then was diluted with 20 ml of methylene chloride, washed subsequently with water and saturated saline solution, dried with anhydrous $Na_2SO_4$, filtered and dried in vacuum. The residue was purified by column chromatography to obtain Compound 1 (0.03 g), Exact Mass (calculated): 454.21; MS(ESI) m/z(M+1)$^+$: 455.22.

Example 2

Synthesis of Compound 2

(R)-1-(3-(4-amino-(4-phenoxyphenyl)-1H-pyrazolo[3,4-d]pyrimidin-1-yl)piperidin-1-yl)-2,2,2-trifluoroethanone

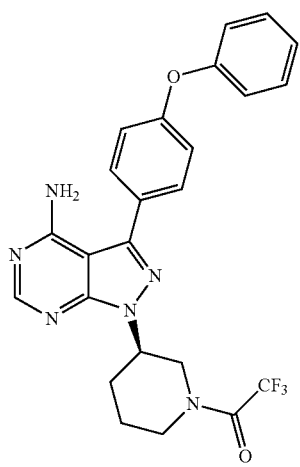 [SMILES: Nc1ncnc2c1c(-c1ccc(Oc3ccccc3)cc1)nn2[C@@H]1CCCN(C(=O)C(F)(F)F)C1]

The synthesis of Compound 2 was accomplished by using a procedure similar to that described in Example 1. Exact Mass (calculated): 482.17; MS(ESI) m/z(M+1)⁺: 483.1722.

Example 3

Synthesis of Compound 3

(R)-3-(4-phenoxyphenyl)-1-(1-((trifluoromethyl)sulfonyl)piperidin-3-yl)-1H-pyrazolo[3,4-d]pyrimidin-4-amine

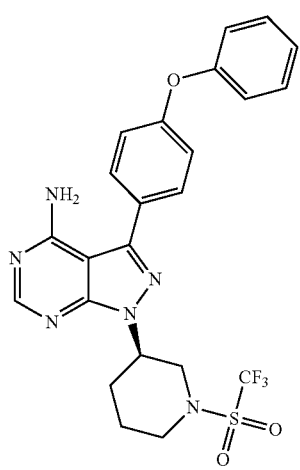 [SMILES: Nc1ncnc2c1c(-c1ccc(Oc3ccccc3)cc1)nn2[C@@H]1CCCN(S(=O)(=O)C(F)(F)F)C1]

The synthesis of Compound 3 was accomplished by using a procedure similar to that described in Example 1. Exact Mass (calculated): 518.13; MS(ESI) m/z(M+1)⁺: 519.1315.

Example 4

Synthesis of Compound 4

(R)-3-(4-amino-(4-phenoxyphenyl)-1H-pyrazolo[3,4-d]pyrimidin-1-yl)piperidin-1-sulfonamide

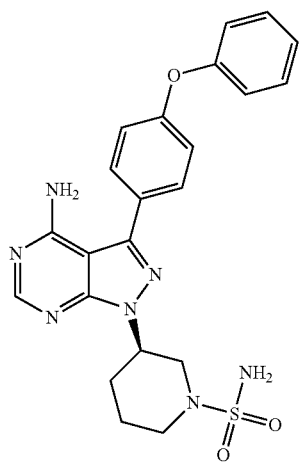 [SMILES: Nc1ncnc2c1c(-c1ccc(Oc3ccccc3)cc1)nn2[C@@H]1CCCN(S(N)(=O)=O)C1]

The synthesis of Compound 4 was accomplished by using a procedure similar to that described in Example 1. Exact Mass (calculated): 465.16; MS(ESI) m/z(M+1)⁺: 466.1615.

Example 5

Synthesis of Compound 5

(R)-2-(3-(4-amino-(4-phenoxyphenyl)-1H-pyrazolo[3,4-d]pyrimidin-1-yl)piperidin-1-yl)-2-oxamide

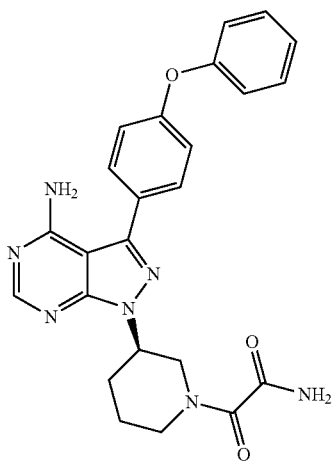 [SMILES: NC(=O)C(=O)N1CCC[C@@H](n2nc(-c3ccc(Oc4ccccc4)cc3)c3c(N)ncnc32)C1]

The synthesis of Compound 5 was accomplished by using a procedure similar to that described in Example 1. Exact Mass (calculated): 457.19; MS(ESI) m/z(M+1)⁺: 458.1915.

Example 6

Synthesis of Compound 6

(S)-2-amino-1-((R)-3-(4-amino-(4-phenoxyphenyl)-1H-pyrazolo[3,4-d]pyrimidin-1-yl)piperidin-1-yl)-3-(1H-imidazol-4-yl)propan-1-one

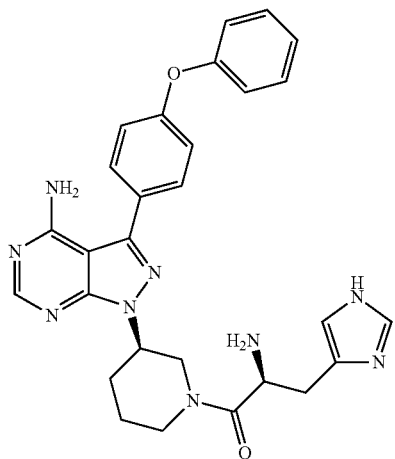 [SMILES: Nc1ncnc2c1c(-c1ccc(Oc3ccccc3)cc1)nn2[C@@H]1CCCN(C(=O)[C@@H](N)Cc2c[nH]cn2)C1]

The synthesis of Compound 6 was accomplished by using a procedure similar to that described in Example 1. Exact Mass (calculated): 523.24; MS(ESI) m/z(M+1)$^+$: 524.2413.

Example 7

Synthesis of Compound 7

(R)-2-amino-1-((R)-3-(4-amino-(4-phenoxyphenyl)-1H-pyrazolo[3,4-d]pyrimidin-1-yl)piperidin-1-yl)-3-(1H-imidazol-4-yl)propan-1-one

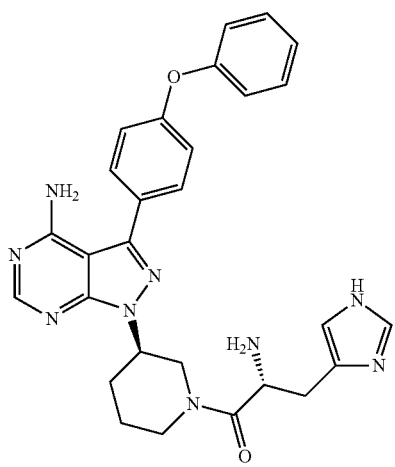 [SMILES: Nc1ncnc2c1c(-c1ccc(Oc3ccccc3)cc1)nn2[C@@H]1CCCN(C(=O)[C@H](N)Cc2c[nH]cn2)C1]

The synthesis of Compound 7 was accomplished by using a procedure similar to that described in Example 1. Exact Mass (calculated): 523.23; MS(ESI) m/z(M+1)$^+$: 524.2314.

Example 8

Synthesis of Compound 8

(R)-2-amino-1-((R)-3-(4-amino-(4-phenoxyphenyl)-1H-pyrazolo[3,4-d]pyrimidin-1-yl)piperidin-1-yl)-3-(1H-indol-3-yl)propan-1-one

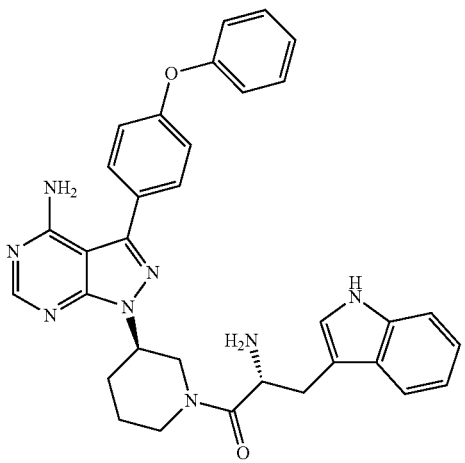 [SMILES: Nc1ncnc2c1c(-c1ccc(Oc3ccccc3)cc1)nn2[C@@H]1CCCN(C(=O)[C@H](N)Cc2c[nH]c3ccccc23)C1]

The synthesis of Compound 8 was accomplished by using a procedure similar to that described in Example 1. Exact Mass (calculated): 572.26; MS(ESI) m/z(M+1)$^+$: 573.2615.

Example 9

Synthesis of Compound 9

(S)-2-amino-1-((R)-3-(4-amino-(4-phenoxyphenyl)-1H-pyrazolo[3,4-d]pyrimidin-1-yl)piperidin-1-yl)-3-(1H-indol-3-yl)propan-1-one

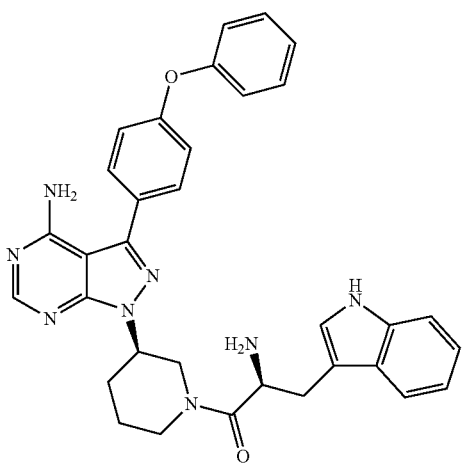 [SMILES: Nc1ncnc2c1c(-c1ccc(Oc3ccccc3)cc1)nn2[C@@H]1CCCN(C(=O)[C@@H](N)Cc2c[nH]c3ccccc23)C1]

The synthesis of Compound 9 was accomplished by using a procedure similar to that described in Example 1. Exact Mass (calculated): 572.26; MS(ESI) m/z(M+1)$^+$: 573.2614.

Example 10

Synthesis of Compound 10

(R)-2-amino-1-((R)-3-(4-amino-(4-phenoxyphenyl)-1H-pyrazolo[3,4-d]pyrimidin-1-yl)piperidin-1-yl)-3-(4-hydroxyphenyl)propan-1-one

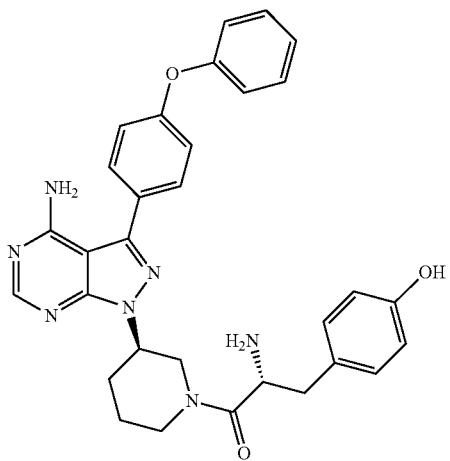 [SMILES: Nc1ncnc2c1c(-c1ccc(Oc3ccccc3)cc1)nn2[C@@H]1CCCN(C(=O)[C@H](N)Cc2ccc(O)cc2)C1]

The synthesis of Compound 10 was accomplished by using a procedure similar to that described in Example 1. Exact Mass (calculated): 549.25; MS(ESI) m/z(M+1)$^+$: 550.2514.

Example 11

Synthesis of Compound 11

(S)-2-amino-1-((R)-3-(4-amino-(4-phenoxyphenyl)-1H-pyrazolo[3,4-d]pyrimidin-1-yl)piperidin-1-yl)-3-(4-hydroxyphenyl)propan-1-one

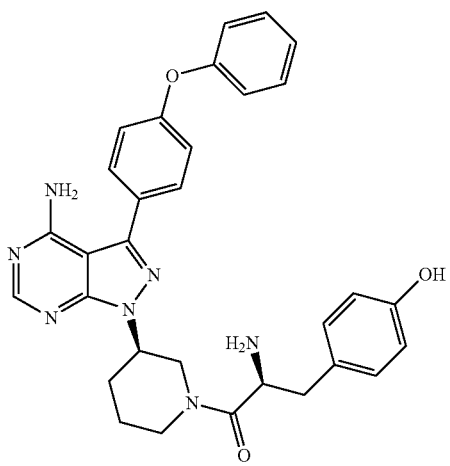 [SMILES: Nc1ncnc2c1c(-c1ccc(Oc3ccccc3)cc1)nn2[C@@H]1CCCN(C(=O)[C@@H](N)Cc2ccc(O)cc2)C1]

The synthesis of Compound 11 was accomplished by using a procedure similar to that described in Example 1. Exact Mass (calculated): 549.25; MS(ESI) m/z(M+1)$^+$: 550.2516.

Example 12

Synthesis of Compound 12

(S)-2-amino-1-((R)-3-(4-amino-(4-phenoxyphenyl)-1H-pyrazolo[3,4-d]pyrimidin-1-yl)piperidin-1-yl)-4-methylpentan-1-one

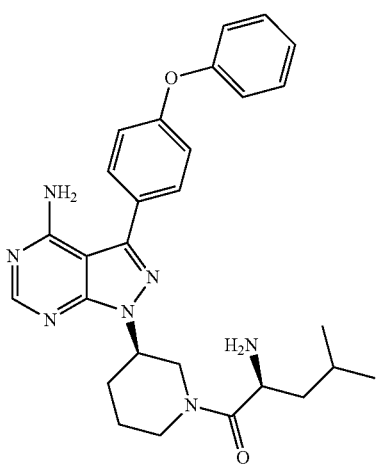 [SMILES: CC(C)C[C@H](N)C(=O)N1CCC[C@@H](n2nc(-c3ccc(Oc4ccccc4)cc3)c3c(N)ncnc32)C1]

The synthesis of Compound 12 was accomplished by using a procedure similar to that described in Example 1. Exact Mass (calculated): 499.27; MS(ESI) m/z(M+1)$^+$: 500.2716.

Example 13

Synthesis of Compound 13

(R)-(3-(4-amino-(4-phenoxyphenyl)-1H-pyrazolo[3,4-d]pyrimidin-1-yl)piperidin-1-yl)(pyridin-3-yl)methanone

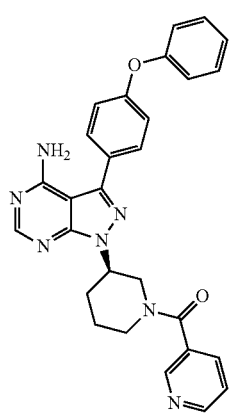 [SMILES: Nc1ncnc2c1c(-c1ccc(Oc3ccccc3)cc1)nn2[C@@H]1CCCN(C(=O)c2cccnc2)C1]

The synthesis of Compound 13 was accomplished by using a procedure similar to that described in Example 1. Exact Mass (calculated): 491.21; MS(ESI) m/z(M+1)$^+$: 492.2121.

Example 14

Synthesis of Compound 14

(R)-(3-(4-amino-(4-phenoxyphenyl)-1H-pyrazolo[3,4-d]pyrimidin-1-yl)piperidin-1-yl)(piperazin-1-yl)methanone

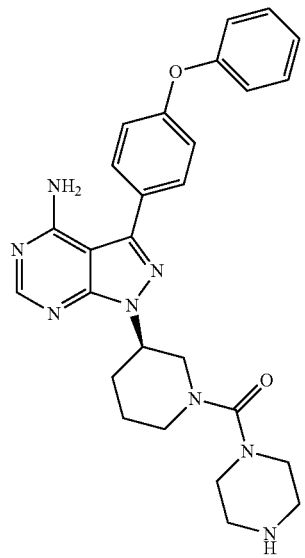 [SMILES: Nc1ncnc2c1c(-c1ccc(Oc3ccccc3)cc1)nn2[C@@H]1CCCN(C(=O)N2CCNCC2)C1]

The synthesis of Compound 14 was accomplished by using a procedure similar to that described in Example 1. Exact Mass (calculated): 498.58; MS(ESI) m/z(M+1)$^+$: 499.5821.

Example 15

Synthesis of Compound 15

(R)-(3-(4-amino-(4-phenoxyphenyl)-1H-pyrazolo[3,4-d]pyrimidin-1-yl)piperidin-1-yl)(pyrimidin-5-yl)methanone

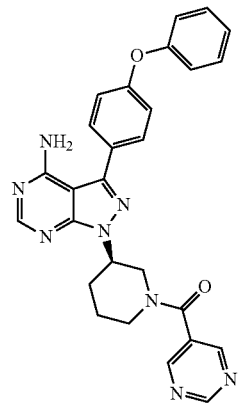 [SMILES: Nc1ncnc2c1c(-c1ccc(Oc3ccccc3)cc1)nn2[C@@H]1CCCN(C(=O)c2cncnc2)C1]

The synthesis of Compound 15 was accomplished by using a procedure similar to that described in Example 1. Exact Mass (calculated): 492.20; MS(ESI) m/z(M+1)$^+$: 493.2021.

Example 16

Synthesis of Compound 16

(R)-methyl 4-(3-(4-amino-(4-phenoxyphenyl)-1H-pyrazolo[3,4-d]pyrimidin-1-yl)piperidine-1-carbonyl)benzoate

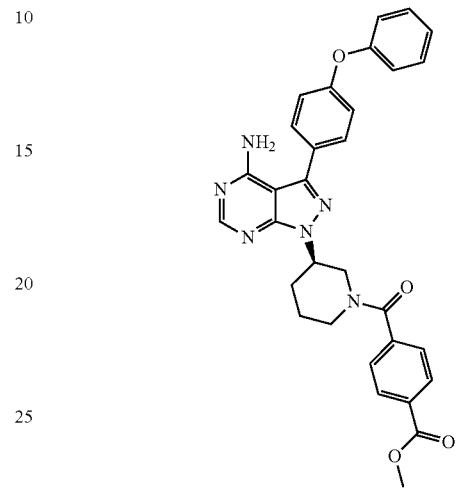

The synthesis of Compound 16 was accomplished by using a procedure similar to that described in Example 1. Exact Mass (calculated): 548.22; MS(ESI) m/z(M+1)$^+$: 549.2221.

Example 17

Synthesis of Compound 17

(R)-(3-(4-amino-(4-phenoxyphenyl)-1H-pyrazolo[3,4-d]pyrimidin-1-yl)piperidin-1-yl)(6-aminopyridin-3-yl)methanone

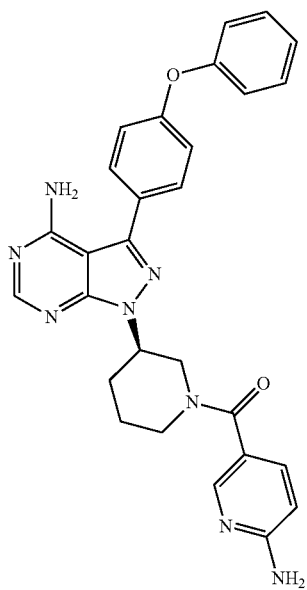 [SMILES: Nc1ccc(C(=O)N2CCC[C@@H](n3nc(-c4ccc(Oc5ccccc5)cc4)c4c(N)ncnc43)C2)cn1]

The synthesis of Compound 17 was accomplished by using a procedure similar to that described in Example 1. Exact Mass (calculated): 506.22; MS(ESI) m/z(M+1)+: 507.2221.

Example 18

Synthesis of Compound 18

(R)-(3-(4-amino-(4-phenoxyphenyl)-1H-pyrazolo[3,4-d]pyrimidin-1-yl)piperidin-1-yl)-(3,4-methylenedioxyphenyl)mathanone

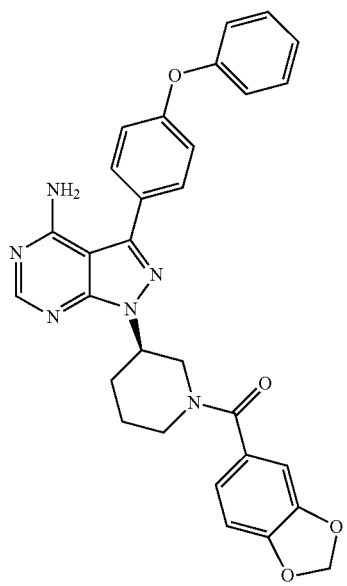 [SMILES: Nc1ncnc2c1c(-c1ccc(Oc3ccccc3)cc1)nn2[C@@H]1CCCN(C(=O)c2ccc3c(c2)OCO3)C1]

The synthesis of Compound 18 was accomplished by using a procedure similar to that described in Example 1. Exact Mass (calculated): 534.20; MS(ESI) m/z(M+1)+: 535.2021.

Example 19

Synthesis of Compound 19

(R)-(3-(4-amino-(4-phenoxyphenyl)-1H-pyrazolo[3,4-d]pyrimidin-1-yl)piperidin-1-yl)-4-piperidinmethanone

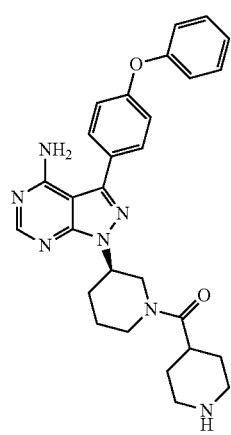 [SMILES: Nc1ncnc2c1c(-c1ccc(Oc3ccccc3)cc1)nn2[C@@H]1CCCN(C(=O)C2CCNCC2)C1]

The synthesis of Compound 19 was accomplished by using a procedure similar to that described in Example 1. Exact Mass (calculated): 497.25; MS(ESI) m/z(M+1)+: 498.2521.

Example 20

Synthesis of Compound 20

(R)-3-(3-(4-amino-(4-phenoxyphenyl)-1H-pyrazolo[3,4-d]pyrimidin-1-yl)piperidin-1-yl)-3-cyanoacetone

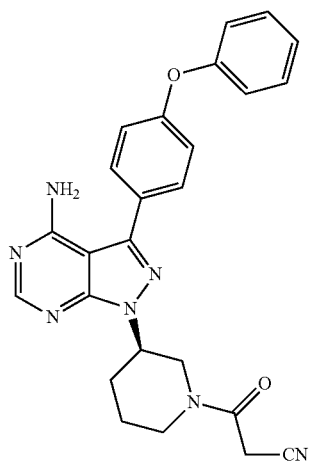 [SMILES: N#CCC(=O)N1CCC[C@@H](n2nc(-c3ccc(Oc4ccccc4)cc3)c3c(N)ncnc32)C1]

The synthesis of Compound 20 was accomplished by using a procedure similar to that described in Example 1. Exact Mass (calculated): 453.19; MS(ESI) m/z(M+1)+: 454.1922.

Example 21

Synthesis of Compound 21

(R)-(3-(4-amino-(4-phenoxyphenyl)-1H-pyrazolo[3,4-d]pyrimidin-1-yl)piperidin-1-yl)(2-aminopyrimidin-5-yl)methanone

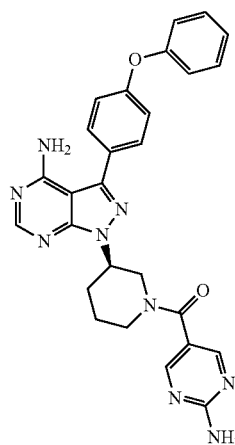

The synthesis of Compound 21 was accomplished by using a procedure similar to that described in Example 1. Exact Mass (calculated): 507.21; MS(ESI) m/z(M+1)+: 508.2134.

Example 22

Synthesis of Compound 22

(R)-1-(3-(4-amino-(4-phenoxyphenyl)-1H-pyrazolo [3,4-d]pyrimidin-1-yl)piperidin-1-yl)-2-(dimethyl-amino)ethanone

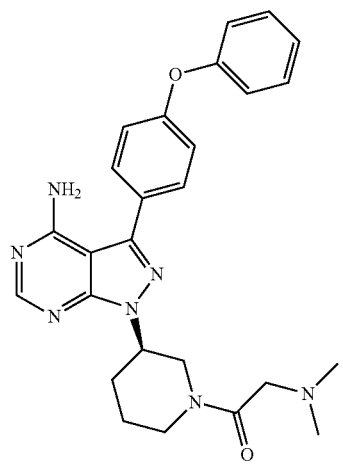 [SMILES: CN(C)CC(=O)N1CCC[C@@H](n2nc(-c3ccc(Oc4ccccc4)cc3)c3c(N)ncnc32)C1]

The synthesis of Compound 22 was accomplished by using a procedure similar to that described in Example 1. Exact Mass (calculated): 471.24; MS(ESI) m/z(M+1)+: 472.2431.

Example 23

Synthesis of Compound 23

1-((R)-3-(4-amino-(4-phenoxyphenyl)-1H-pyrazolo [3,4-d]pyrimidin-1-yl)piperidin-1-yl)-2-hydroxylpropan-1-one

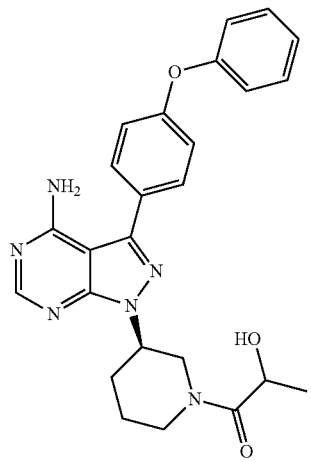 [SMILES: CC(O)C(=O)N1CCC[C@@H](n2nc(-c3ccc(Oc4ccccc4)cc3)c3c(N)ncnc32)C1]

The synthesis of Compound 23 was accomplished by using a procedure similar to that described in Example 1. Exact Mass (calculated): 458.21; MS(ESI) m/z(M+1)+: 458.2124.

Example 24

Synthesis of Compound 24

(R)-2-amino-1-((R)-3-(4-amino-(4-phenoxyphenyl)-1H-pyrazolo[3,4-d]pyrimidin-1-yl)piperidin-1-yl) propan-1-one

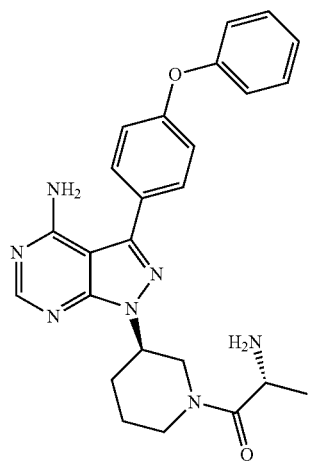

The synthesis of Compound 24 was accomplished by using a procedure similar to that described in Example 1. Exact Mass (calculated): 457.22; MS(ESI) m/z(M+1)+: 458.2234.

Example 25

Synthesis of Compound 25

(2R,3R)-2-amino-1-((R)-3-(4-amino-(4-phenoxyphenyl)-1H-pyrazolo[3,4-d]pyrimidin-1-yl)piperidin-1-yl)-3-methylpentan-1-one

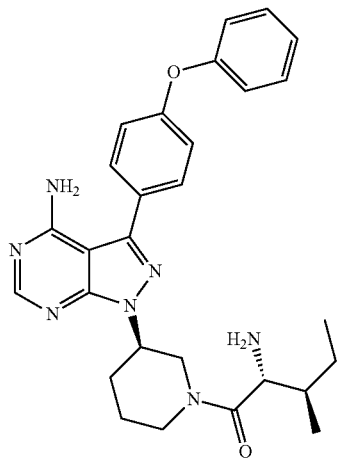 [SMILES: CC[C@@H](C)[C@@H](N)C(=O)N1CCC[C@@H](n2nc(-c3ccc(Oc4ccccc4)cc3)c3c(N)ncnc32)C1]

The synthesis of Compound 25 was accomplished by using a procedure similar to that described in Example 1. Exact Mass (calculated): 499.27; MS(ESI) m/z(M+1)$^+$: 500.2731.

Example 26

Synthesis of Compound 26

(R)-2-amino-1-((R)-3-(4-amino-(4-phenoxyphenyl)-1H-pyrazolo[3,4-d]pyrimidin-1-yl)piperidin-1-yl)-3-phenylpropan-1-one

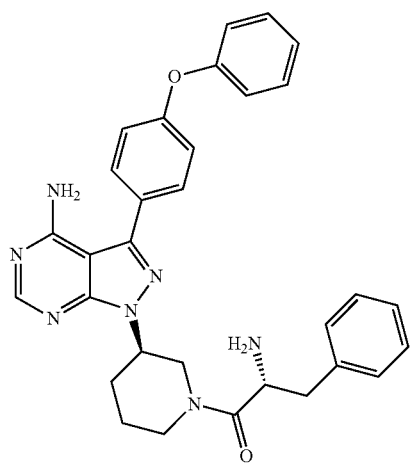 [SMILES: Nc1ncnc2c1c(-c1ccc(Oc3ccccc3)cc1)nn2[C@@H]1CCCN(C(=O)[C@H](N)Cc2ccccc2)C1]

The synthesis of Compound 26 was accomplished by using a procedure similar to that described in Example 1. Exact Mass (calculated): 533.25; MS(ESI) m/z(M+1)$^+$: 534.2541.

Example 27

Synthesis of Compound 27

(R)-2-amino-1-((R)-3-(4-amino-(4-phenoxyphenyl)-1H-pyrazolo[3,4-d]pyrimidin-1-yl)piperidin-1-yl)-4-methylpentan-1-one

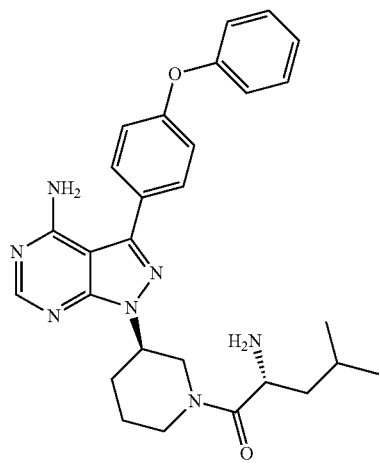 [SMILES: CC(C)C[C@@H](N)C(=O)N1CCC[C@@H](n2nc(-c3ccc(Oc4ccccc4)cc3)c3c(N)ncnc32)C1]

The synthesis of Compound 27 was accomplished by using a procedure similar to that described in Example 1. Exact Mass (calculated): 499.27; MS(ESI) m/z(M+1)$^+$: 500.2733.

Example 28

Synthesis of Compound 28

(R)-2-amino-1-((R)-3-(4-amino-(4-phenoxyphenyl)-1H-pyrazolo[3,4-d]pyrimidin-1-yl)pyrrolidin-1-yl)-4-methylpentan-1-one

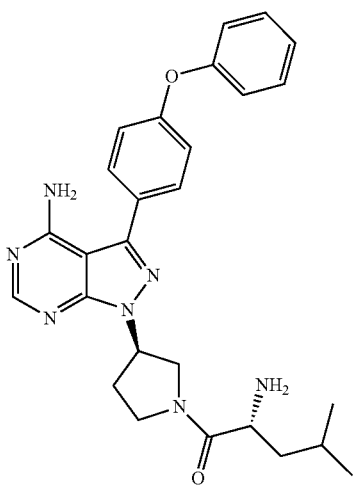 [SMILES: CC(C)C[C@@H](N)C(=O)N1CC[C@@H](n2nc(-c3ccc(Oc4ccccc4)cc3)c3c(N)ncnc32)C1]

The synthesis of Compound 28 was accomplished by using a procedure similar to that described in Example 1. Exact Mass (calculated): 485.58; MS(ESI) m/z(M+1)$^+$: 486.5833.

Example 29

Synthesis of Compound 29

(R)-(3-(4-amino-(4-phenoxyphenyl)-1H-pyrazolo[3,4-d]pyrimidin-1-yl)piperidin-1-yl)(isoxazol-5-yl)methanone

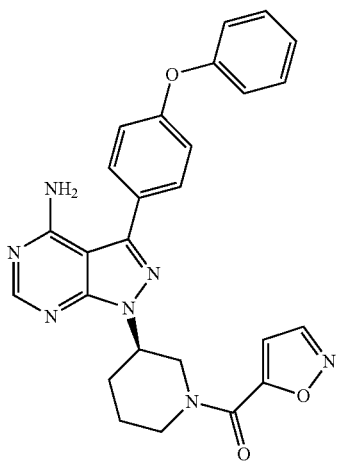 [SMILES: Nc1ncnc2c1c(-c1ccc(Oc3ccccc3)cc1)nn2[C@@H]1CCCN(C(=O)c2ccno2)C1]

The synthesis of Compound 29 was accomplished by using a procedure similar to that described in Example 1. Exact Mass (calculated): 481.19; MS(ESI) m/z(M+1)$^+$: 482.1921.

Example 30

Synthesis of Compound 30

(R)-1-(1-(methylsulfonyl)piperidin-3-yl)-3-(4-phenoxyphenyl)-1H-pyrazolo[3,4-d]pyrimidin-4-amine

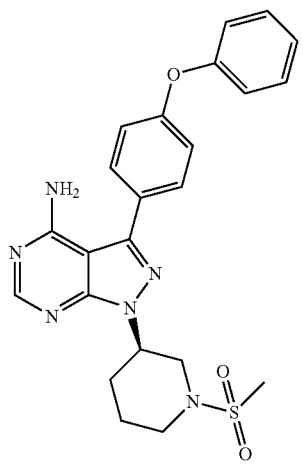 [SMILES: CS(=O)(=O)N1CCC[C@@H](n2nc(-c3ccc(Oc4ccccc4)cc3)c3c(N)ncnc32)C1]

The synthesis of Compound 30 was accomplished by using a procedure similar to that described in Example 1. Exact Mass (calculated): 464.16; MS(ESI) m/z(M+1)$^+$: 465.1622.

Example 31

Synthesis of Compound 31

(R)-3-(4-amino-(4-phenoxyphenyl)-1H-pyrazolo[3,4-d]pyrimidin-1-yl) piperidin-1-yl)-2-morpholinoethanone

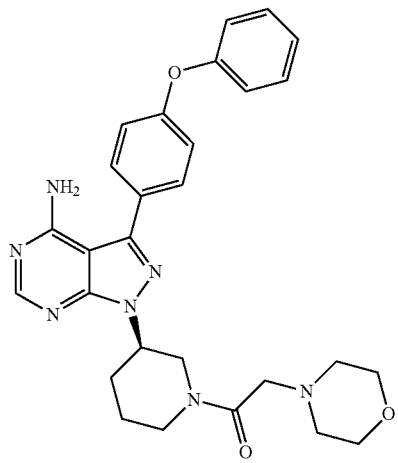 [SMILES: Nc1ncnc2c1c(-c1ccc(Oc3ccccc3)cc1)nn2[C@@H]1CCCN(C(=O)CN2CCOCC2)C1]

The synthesis of Compound 31 was accomplished by using a procedure similar to that described in Example 1. Exact Mass (calculated): 513.25; MS(ESI) m/z(M+1)$^+$: 514.2531.

Example 32

Synthesis of Compound 32

(R)-3-(4-amino-(4-phenoxyphenyl)-1H-pyrazolo[3,4-d]pyrimidin-1-yl) piperidin-1-yl)(cyclopentan-2-yl)ethanone

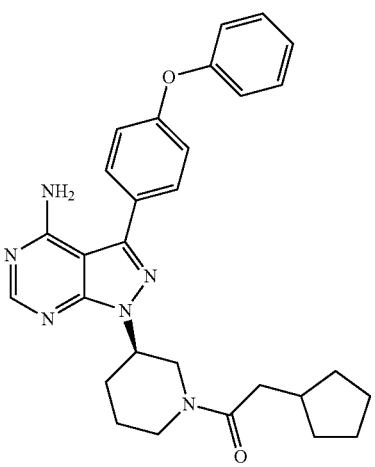 [SMILES: Nc1ncnc2c1c(-c1ccc(Oc3ccccc3)cc1)nn2[C@@H]1CCCN(C(=O)CC2CCCC2)C1]

The synthesis of Compound 32 was accomplished by using a procedure similar to that described in Example 1. Exact Mass (calculated): 496.26; MS(ESI) m/z(M+1)$^+$: 496.2631.

Example 33

Synthesis of Compound 33

(R)-(3-(4-amino-(4-phenoxyphenyl)-1H-pyrazolo[3,4-d]pyrimidin-1-yl)piperidin-1-yl)(1-methylpiperidin-4-yl)methanone

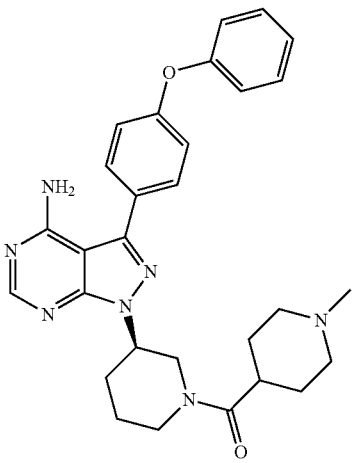 [SMILES: CN1CCC(C(=O)N2CCC[C@@H](n3nc(-c4ccc(Oc5ccccc5)cc4)c4c(N)ncnc43)C2)CC1]

The synthesis of Compound 33 was accomplished by using a procedure similar to that described in Example 1. Exact Mass (calculated): 511.27; MS(ESI) m/z(M+1)+: 512.2731.

Example 34

Synthesis of Compound 34

(R)-3-(4-amino-(4-phenoxyphenyl)-1H-pyrazolo[3,4-d]pyrimidin-1-yl) piperidin-1-yl)ethanone

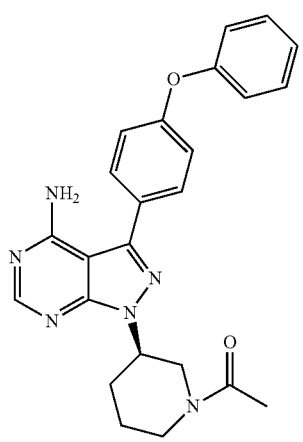 [SMILES: CC(=O)N1CCC[C@@H](n2nc(-c3ccc(Oc4ccccc4)cc3)c3c(N)ncnc32)C1]

The synthesis of Compound 34 was accomplished by using a procedure similar to that described in Example 1. Exact Mass (calculated): 428.20; MS(ESI) m/z(M+1)+: 429.2031.

Example 35

Synthesis of Compound 35

(R)-(3-(4-amino-(4-phenoxyphenyl)-1H-pyrazolo[3,4-d]pyrimidin-1-yl)piperidin-1-yl)(4-((4-methylpiperazin-1-yl)methyl)phenyl)methanone

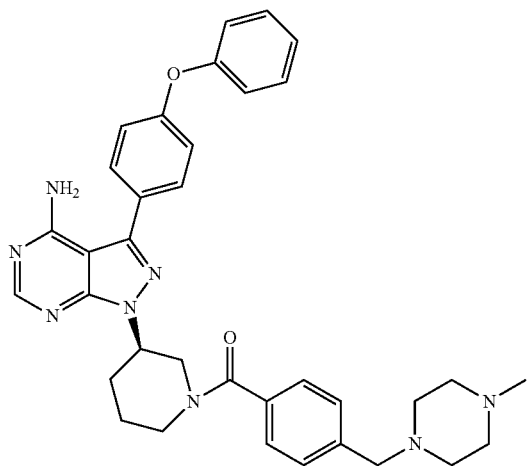 [SMILES: CN1CCN(Cc2ccc(C(=O)N3CCC[C@@H](n4nc(-c5ccc(Oc6ccccc6)cc5)c5c(N)ncnc54)C3)cc2)CC1]

The synthesis of Compound 35 was accomplished by using a procedure similar to that described in Example 1. Exact Mass (calculated): 602.31; MS(ESI) m/z(M+1)+: 602.3123.

Example 36

Synthesis of Compound 36

(R)-3-(4-amino-(4-phenoxyphenyl)-1H-pyrazolo[3,4-d]pyrimidin-1-yl) piperidin-1-yl)-3-chloroacetone

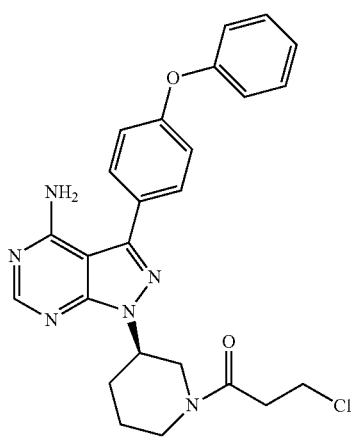 [SMILES: Nc1ncnc2c1c(-c1ccc(Oc3ccccc3)cc1)nn2[C@@H]1CCCN(C(=O)CCCl)C1]

The synthesis of Compound 36 was accomplished by using a procedure similar to that described in Example 1. Exact Mass (calculated): 476.17; MS(ESI) m/z(M+1)+: 477.1723.

Example 37

Synthesis of Compound 37

(R)-3-(4-amino-(4-phenoxyphenyl)-1H-pyrazolo[3,4-d]pyrimidin-1-yl) piperidin-1-yl)-2-bromoacetone

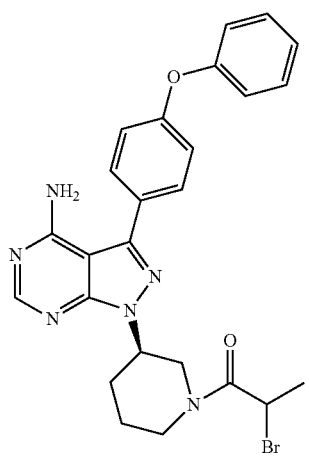 [SMILES: CC(Br)C(=O)N1CCC[C@@H](n2nc(-c3ccc(Oc4ccccc4)cc3)c3c(N)ncnc32)C1]

The synthesis of Compound 37 was accomplished by using a procedure similar to that described in Example 1. Exact Mass (calculated): 520.12; MS(ESI) m/z(M+1)⁺: 522.1217.

Example 38

Synthesis of Compound 38

(R)-3-(4-amino-(4-phenoxyphenyl)-1H-pyrazolo[3,4-d]pyrimidin-1-yl) piperidin-1-yl)-2-chloroacetone

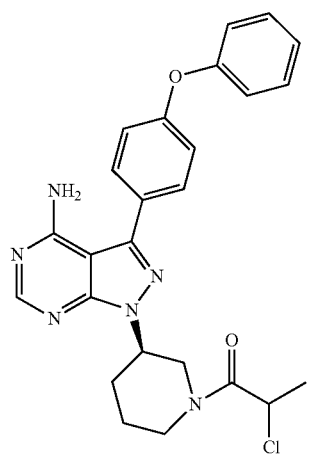 [SMILES: CC(Cl)C(=O)N1CCC[C@@H](n2nc(-c3ccc(Oc4ccccc4)cc3)c3c(N)ncnc32)C1]

The synthesis of Compound 38 was accomplished by using a procedure similar to that described in Example 1. Exact Mass (calculated): 476.17; MS(ESI) m/z(M+1)⁺: 477.1725.

Example 39

Synthesis of Compound 39

(R)-3-(4-amino-(4-phenoxyphenyl)-1H-pyrazolo[3,4-d]pyrimidin-1-yl) piperidin-1-yl)-2-(4-methylpiperazin-1-yl)ethanone

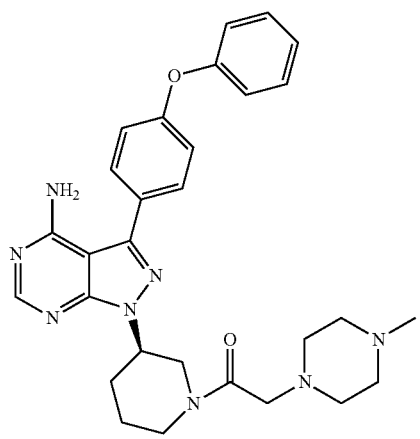 [SMILES: CN1CCN(CC(=O)N2CCC[C@@H](n3nc(-c4ccc(Oc5ccccc5)cc4)c4c(N)ncnc43)C2)CC1]

The synthesis of Compound 39 was accomplished by using a procedure similar to that described in Example 1. Exact Mass (calculated): 526.28; MS(ESI) m/z(M+1)⁺: 527.2826.

Example 40

Synthesis of Compound 40

(R)-3-(4-phenoxyphenyl)-1-(1-(propylsulfonyl)piperidin-3-yl)-1H-pyrazolo[3,4-d]pyrimidin-4-amine

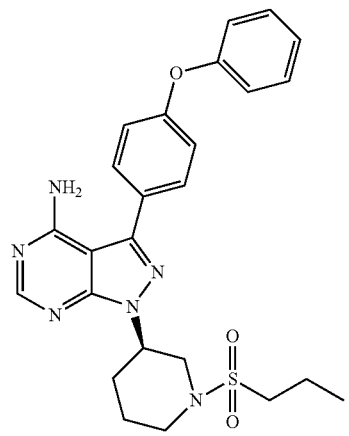 [SMILES: CCCS(=O)(=O)N1CCC[C@@H](n2nc(-c3ccc(Oc4ccccc4)cc3)c3c(N)ncnc32)C1]

The synthesis of Compound 40 was accomplished by using a procedure similar to that described in Example 1. Exact Mass (calculated): 492.19; MS(ESI) m/z(M+1)⁺: 493.1921.

Example 41

Synthesis of Compound 41

(R)-3-(4-phenoxyphenyl)-1-(1-(ethylsulfonyl)piperidin-3-yl)-1H-pyrazolo[3,4-d]pyrimidin-4-amine

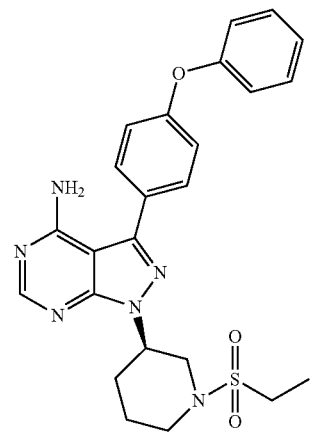 [SMILES: CCS(=O)(=O)N1CCC[C@@H](n2nc(-c3ccc(Oc4ccccc4)cc3)c3c(N)ncnc32)C1]

The synthesis of Compound 41 was accomplished by using a procedure similar to that described in Example 1. Exact Mass (calculated): 478.18; MS(ESI) m/z(M+1)⁺: 479.1821.

Example 42

Synthesis of Compound 42

(R)-3-(4-amino-(4-phenoxyphenyl)-1H-pyrazolo[3,4-d]pyrimidin-1-yl) piperidin-1-yl)trichloroethanone

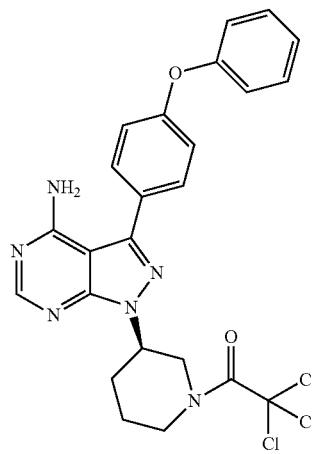

The synthesis of Compound 42 was accomplished by using a procedure similar to that described in Example 1. Exact Mass (calculated): 478.18; MS(ESI) m/z(M+1)$^+$: 479.1821.

Example 43

Synthesis of Compound 43

(R)-2-amino-1-(3-(4-amino-(4-phenoxyphenyl)-1H-pyrazolo[3,4-d]pyrimidin-1-yl)piperidin-1-yl)ethanone

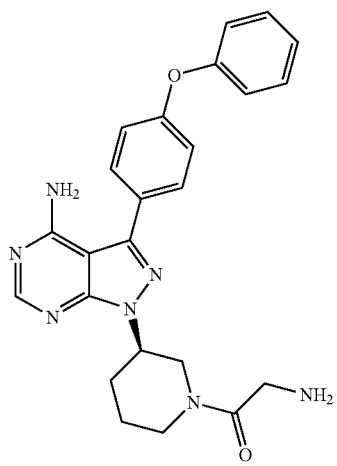 [SMILES: NCC(=O)N1CCC[C@@H](n2nc(-c3ccc(Oc4ccccc4)cc3)c3c(N)ncnc32)C1]

The synthesis of Compound 43 was accomplished by using a procedure similar to that described in Example 1. Exact Mass (calculated): 443.21; MS(ESI) m/z(M+1)$^+$: 444.2118.

Example 44

Synthesis of Compound 44

(R)-2-amino-1-((R)-3-(4-amino-(4-phenoxyphenyl)-1H-pyrazolo[3,4-d]pyrimidin-1-yl)piperidin-1-yl)-3-hydroxybutanone

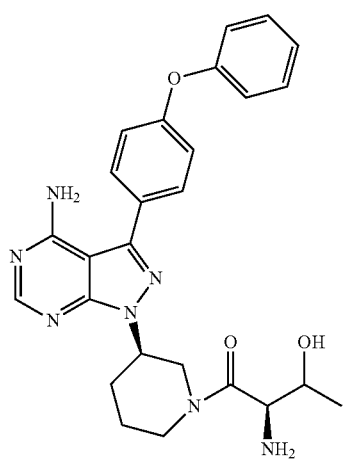 [SMILES: CC(O)[C@@H](N)C(=O)N1CCC[C@@H](n2nc(-c3ccc(Oc4ccccc4)cc3)c3c(N)ncnc32)C1]

The synthesis of Compound 44 was accomplished by using a procedure similar to that described in Example 1. Exact Mass (calculated): 487.23; MS(ESI) m/z(M+1)$^+$: 488.2321.

Example 45

Synthesis of Compound 45

(R)-2-amino-1-((R)-3-(4-amino-(4-phenoxyphenyl)-1H-pyrazolo[3,4-d]pyrimidin-1-yl)piperidin-1-yl)-3-methylbutanone

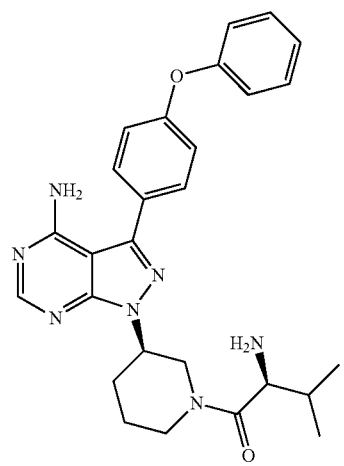 [SMILES: CC(C)[C@H](N)C(=O)N1CCC[C@@H](n2nc(-c3ccc(Oc4ccccc4)cc3)c3c(N)ncnc32)C1]

The synthesis of Compound 45 was accomplished by using a procedure similar to that described in Example 1. Exact Mass (calculated): 485.25; MS(ESI) m/z(M+1)$^+$: 486.2531.

Example 46

Synthesis of Compound 46

(R)-3-amino-1-(3-(4-amino-(4-phenoxyphenyl)-1H-pyrazolo[3,4-d]pyrimidin-1-yl)piperidin-1-yl)acetone

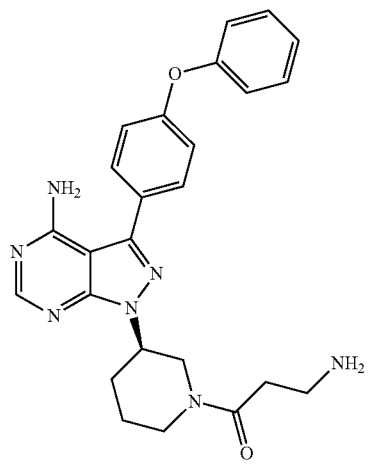 [SMILES: NCCC(=O)N1CCC[C@@H](n2nc(-c3ccc(Oc4ccccc4)cc3)c3c(N)ncnc32)C1]

The synthesis of Compound 46 was accomplished by using a procedure similar to that described in Example 1. Exact Mass (calculated): 457.22; MS(ESI) m/z(M+1)$^+$: 457.2221.

Example 47

Synthesis of Compound 47

(R)-2-amino-1-((R)-(3-(4-amino-(4-phenoxyphenyl)-1H-pyrazolo[3,4-d]pyrimidin-1-yl)piperidin-1-yl)acetone

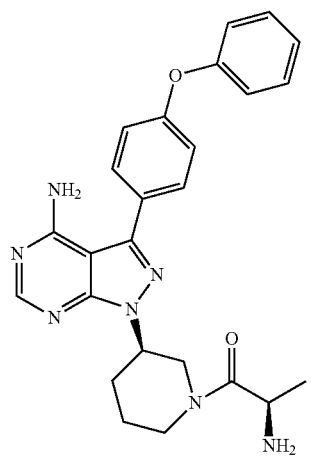 [SMILES: C[C@@H](N)C(=O)N1CCC[C@@H](n2nc(-c3ccc(Oc4ccccc4)cc3)c3c(N)ncnc32)C1]

The synthesis of Compound 47 was accomplished by using a procedure similar to that described in Example 1. Exact Mass (calculated): 457.22; MS(ESI) m/z(M+1)$^+$: 458.2226.

Example 48

Synthesis of Compound 48

(R)-2-amino-1-((R)-(3-(4-amino-(4-phenoxyphenyl)-1H-pyrazolo[3,4-d]pyrimidin-1-yl)piperidin-1-yl)-3-hydroxylacetone

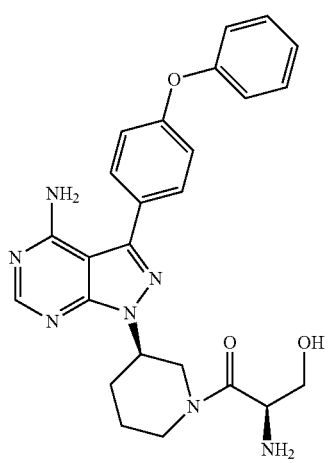 [SMILES: Nc1ncnc2c1c(-c1ccc(Oc3ccccc3)cc1)nn2[C@@H]1CCCN(C(=O)[C@H](N)CO)C1]

The synthesis of Compound 48 was accomplished by using a procedure similar to that described in Example 1. Exact Mass (calculated): 473.22; MS(ESI) m/z(M+1)$^+$: 474.2225.

Example 49

Synthesis of Compound 49

(R)-3-(4-amino-(4-phenoxyphenyl)-1H-pyrazolo[3,4-d]pyrimidin-1-yl) piperidin-1-yl)-3,3-dimethylbutanone

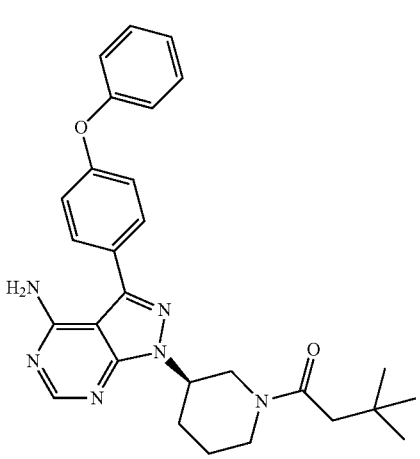 [SMILES: CC(C)(C)CC(=O)N1CCC[C@@H](n2nc(-c3ccc(Oc4ccccc4)cc3)c3c(N)ncnc32)C1]

The synthesis of Compound 49 was accomplished by using a procedure similar to that described in Example 1. Exact Mass (calculated): 473.22; MS(ESI) m/z(M+1)$^+$: 474.2225.

Example 50

Synthesis of Compound 50

(R)-3-(4-amino-(4-phenoxyphenyl)-1H-pyrazolo[3,4-d]pyrimidin-1-yl) piperidin-1-yl)-2,2-dimethylbutanone

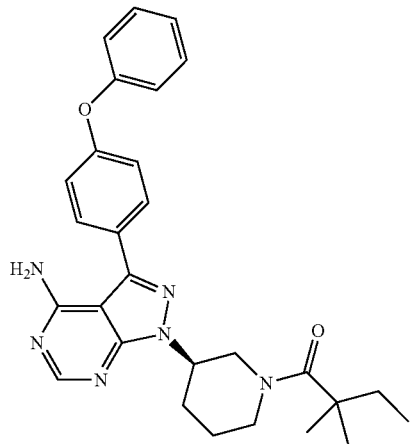 [SMILES: CCC(C)(C)C(=O)N1CCC[C@@H](n2nc(-c3ccc(Oc4ccccc4)cc3)c3c(N)ncnc32)C1]

The synthesis of Compound 50 was accomplished by using a procedure similar to that described in Example 1. Exact Mass (calculated): 473.22; MS(ESI) m/z(M+1)$^+$: 474.2226.

Example 51

Synthesis of Compound 51

(R)-3-(4-amino-(4-phenoxyphenyl)-1H-pyrazolo[3,4-d]pyrimidin-1-yl) piperidin-1-yl)-3,3,3-trifluoroacetone

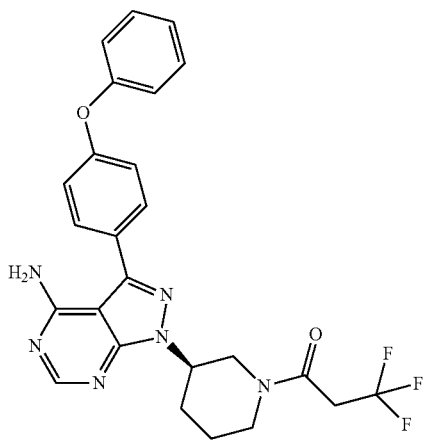 [SMILES: Nc1ncnc2c1c(-c1ccc(Oc3ccccc3)cc1)nn2[C@@H]1CCCN(C(=O)CC(F)(F)F)C1]

The synthesis of Compound 51 was accomplished by using a procedure similar to that described in Example 1. Exact Mass (calculated): 496.18; MS(ESI) m/z(M+1)$^+$: 497.1824.

Example 52

Synthesis of Compound 52

(R)-3-(4-amino-(4-phenoxyphenyl)-1H-pyrazolo[3,4-d]pyrimidin-1-yl) piperidin-1-yl)-2-cyclopropyl-ethanone

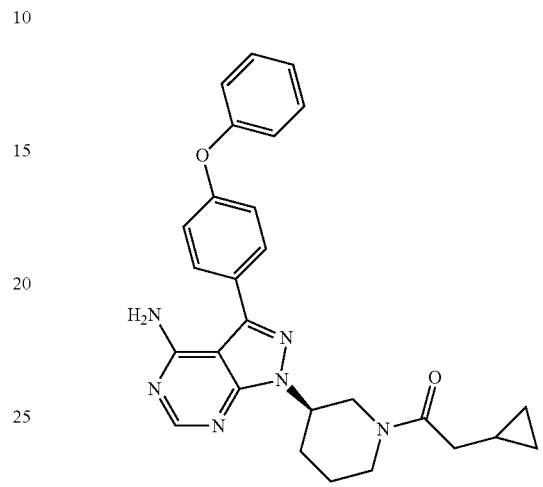

The synthesis of Compound 52 was accomplished by using a procedure similar to that described in Example 1. Exact Mass (calculated): 468.23; MS(ESI) m/z(M+1)$^+$: 469.2327.

Example 53

Synthesis of Compound 53

(R)-3-(4-amino-(4-phenoxyphenyl)-1H-pyrazolo[3,4-d]pyrimidin-1-yl) piperidin-1-yl)-3-methylbutanone

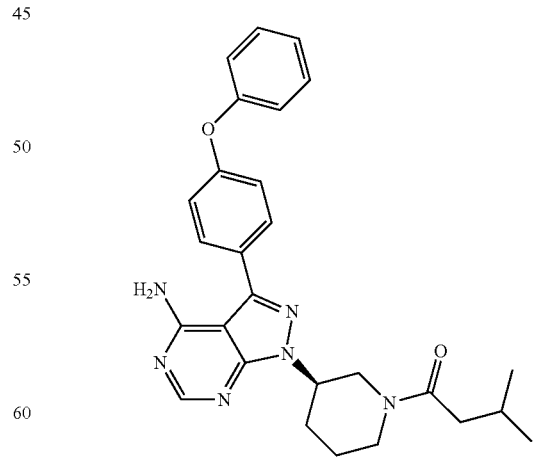

The synthesis of Compound 53 was accomplished by using a procedure similar to that described in Example 1. Exact Mass (calculated): 470.24; MS(ESI) m/z(M+1)$^+$: 471.2427.

Example 54

Synthesis of Compound 54

(R)-3-(4-amino-(4-phenoxyphenyl)-1H-pyrazolo[3,4-d]pyrimidin-1-yl) piperidin-1-yl)butanone

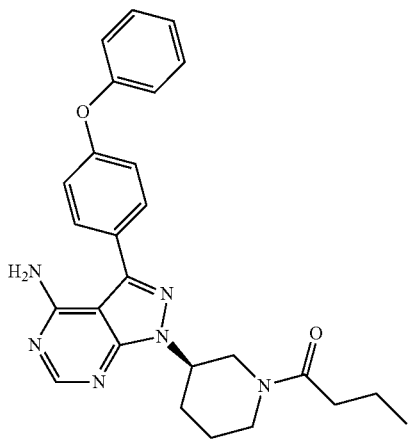 [SMILES: CCCC(=O)N1CCC[C@@H](n2nc(-c3ccc(Oc4ccccc4)cc3)c3c(N)ncnc32)C1]

The synthesis of Compound 54 was accomplished by using a procedure similar to that described in Example 1. Exact Mass (calculated): 456.23; MS(ESI) m/z(M+1)$^+$: 457.2327.

Example 55

Synthesis of Compound 55

(R)-3-(4-amino-(4-phenoxyphenyl)-1H-pyrazolo[3,4-d]pyrimidin-1-yl) piperidin-1-yl)-2,2-dimethylacetone

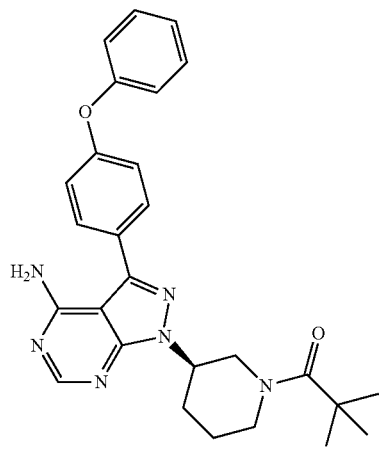 [SMILES: CC(C)(C)C(=O)N1CCC[C@@H](n2nc(-c3ccc(Oc4ccccc4)cc3)c3c(N)ncnc32)C1]

The synthesis of Compound 55 was accomplished by using a procedure similar to that described in Example 1. Exact Mass (calculated): 470.24; MS(ESI) m/z(M+1)$^+$: 471.2426.

Example 56

Synthesis of Compound 56

(S)-4-amino-5-((R)-3-(4-amino-(4-phenoxyphenyl)-1H-pyrazolo[3,4-d]pyrimidin-1-yl)piperidin-1-yl)-5-carbonylpentanamide

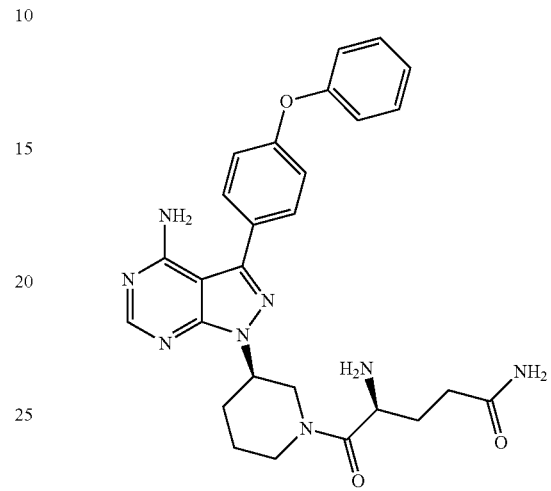

The synthesis of Compound 56 was accomplished by using a procedure similar to that described in Example 1. Exact Mass (calculated): 514.24; MS(ESI) m/z(M+1)$^+$: 515.2428.

Example 57

Synthesis of Compound 57

(R)-4-amino-5-((R)-3-(4-amino-(4-phenoxyphenyl)-1H-pyrazolo[3,4-d]pyrimidin-1-yl)piperidin-1-yl)-5-carbonylpentanamide

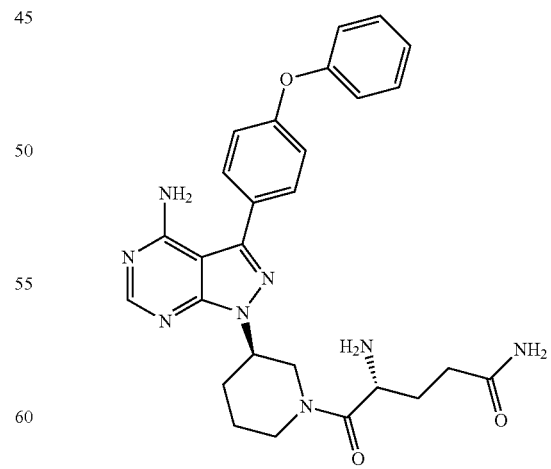

The synthesis of Compound 57 was accomplished by using a procedure similar to that described in Example 1. Exact Mass (calculated): 514.24; MS(ESI) m/z(M+1)$^+$: 515.2427.

Example 58

Synthesis of Compound 58

(R)-1-(3-(4-amino-(4-phenoxyphenyl)-1H-pyrazolo[3,4-d]pyrimidin-1-yl)piperidin-1-yl)-3-(4-methylpiperazin-1-yl)acetone

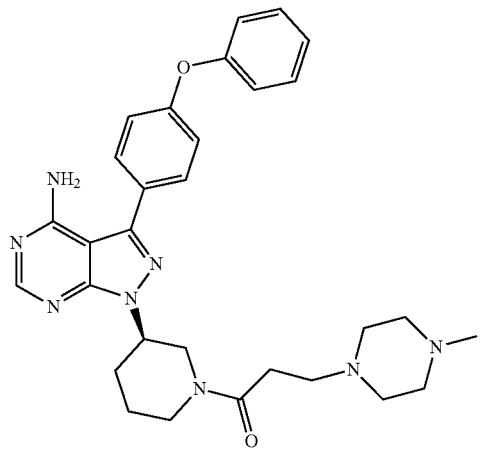 [SMILES: CN1CCN(CCC(=O)N2CCC[C@@H](n3nc(-c4ccc(Oc5ccccc5)cc4)c4c(N)ncnc43)C2)CC1]

The synthesis of Compound 58 was accomplished by using a procedure similar to that described in Example 1. Exact Mass (calculated): 540.31; MS(ESI) m/z(M+1)$^+$: 541.3135.

Example 59

Synthesis of Compound 59

(R)-tert-butyl 2-(3-(4-amino-3-(4-phenoxyphenyl)-1H-pyrazolo[3,4-d]pyrimidin-1-yl)piperidin-1-yl)-2-oxoethylcarbamate

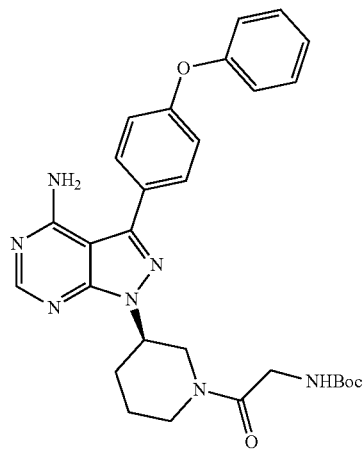 [SMILES: CC(C)(C)OC(=O)NCC(=O)N1CCC[C@@H](n2nc(-c3ccc(Oc4ccccc4)cc3)c3c(N)ncnc32)C1]

The synthesis of Compound 59 was accomplished by using a procedure similar to that described in Example 1. Exact Mass (calculated): 543.26; MS(ESI) m/z(M+1)$^+$: 544.2627.

Example 60

Synthesis of Compound 60

(R)-methyl 4-(3-(4-amino-(4-phenoxyphenyl)-1H-pyrazolo[3,4-d]pyrimidin-1-yl)piperidine-1-carbonyl)piperidin-1-carboxylate

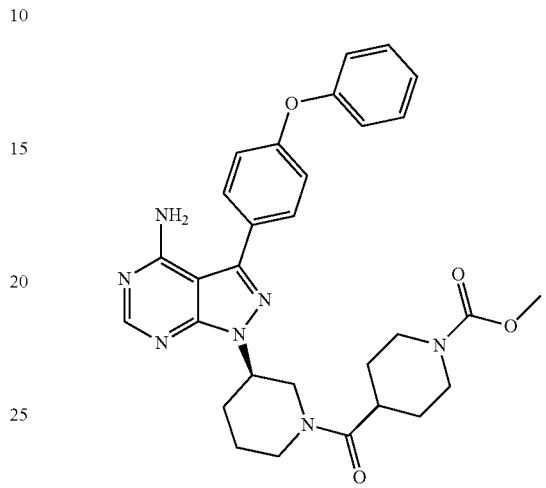

The synthesis of Compound 60 was accomplished by using a procedure similar to that described in Example 1. Exact Mass (calculated): 555.26; MS(ESI) m/z(M+1)$^+$: 556.2627.

Example 61

Synthesis of Compound 61

(R)-1-((R)-3-(4-amino-(4-phenoxyphenyl)-1H-pyrazolo[3,4-d]pyrimidin-1-yl)piperidin-1-yl)-2-hydroxyl-4-methylpentan-1-one

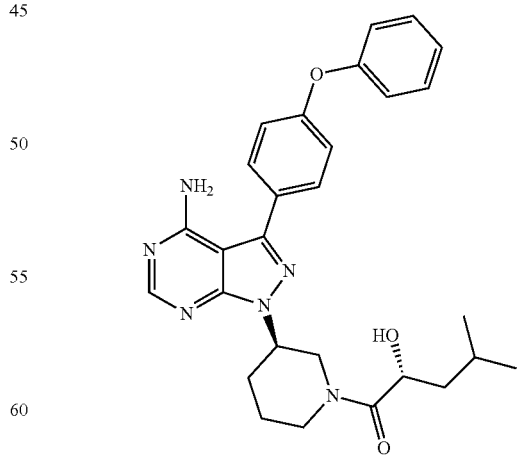

The synthesis of Compound 61 was accomplished by using a procedure similar to that described in Example 1. Exact Mass (calculated): 500.25; MS(ESI) m/z(M+1)$^+$: 501.2527.

Example 62

Synthesis of Compound 62

(R)-3-(4-amino-(4-phenoxyphenyl)-1H-pyrazolo[3,4-d]pyrimidin-1-yl) piperidin-1-yl)-5-aminopentanone

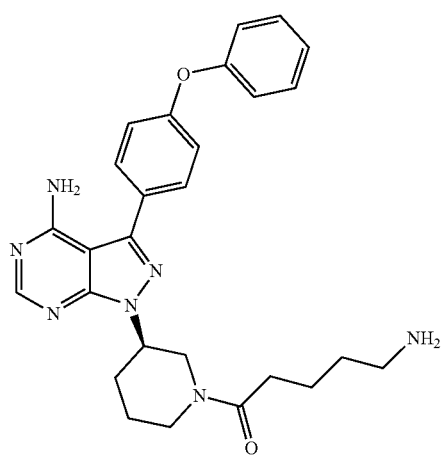 [SMILES: NCCCCC(=O)N1CCC[C@@H](n2nc(-c3ccc(Oc4ccccc4)cc3)c3c(N)ncnc32)C1]

The synthesis of Compound 62 was accomplished by using a procedure similar to that described in Example 1. Exact Mass (calculated): 485.25; MS(ESI) m/z(M+1)$^+$: 486.2526.

Example 63

Synthesis of Compound 63

(R)-3-(4-amino-(4-phenoxyphenyl)-1H-pyrazolo[3,4-d]pyrimidin-1-yl) piperidin-1-yl)-2-hydroxyl-hexan-1-one

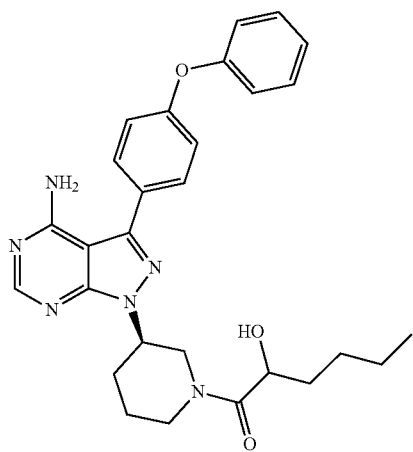 [SMILES: CCCCC(O)C(=O)N1CCC[C@@H](n2nc(-c3ccc(Oc4ccccc4)cc3)c3c(N)ncnc32)C1]

The synthesis of Compound 63 was accomplished by using a procedure similar to that described in Example 1. Exact Mass (calculated): 500.25; MS(ESI) m/z(M+1)$^+$: 501.2528.

Example 64

Synthesis of Compound 64

(R)-3-(4-amino-(4-phenoxyphenyl)-1H-pyrazolo[3,4-d]pyrimidin-1-yl) pyrrolidin-1-yl)-2-aminoethanone

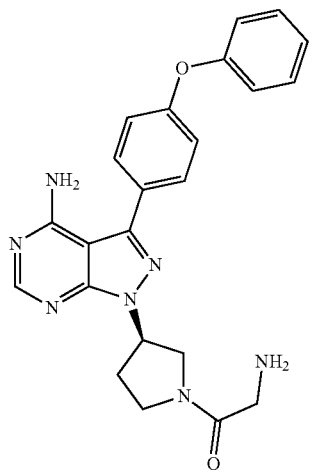 [SMILES: NCC(=O)N1CC[C@@H](n2nc(-c3ccc(Oc4ccccc4)cc3)c3c(N)ncnc32)C1]

The synthesis of Compound 64 was accomplished by using a procedure similar to that described in Example 1. Exact Mass (calculated): 429.19; MS(ESI) m/z(M+1)$^+$: 430.1928.

Example 65

Synthesis of Compound 65

(R)-3-(4-amino-(4-phenoxyphenyl)-1H-pyrazolo[3,4-d]pyrimidin-1-yl) pyrrolidin-1-yl)-2-(dimethylamino)ethanone

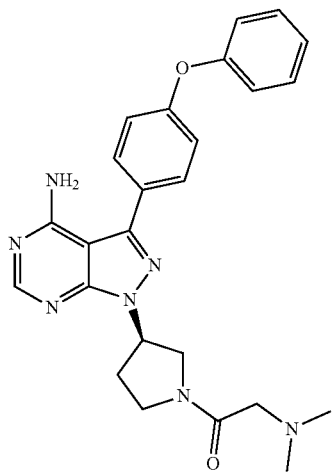 [SMILES: CN(C)CC(=O)N1CC[C@@H](n2nc(-c3ccc(Oc4ccccc4)cc3)c3c(N)ncnc32)C1]

The synthesis of Compound 65 was accomplished by using a procedure similar to that described in Example 1. Exact Mass (calculated): 457.22; MS(ESI) m/z(M+1)$^+$: 458.2225.

Example 66

Synthesis of Compound 66

(R)-tert-butyl 2-(3-(4-amino-(4-phenoxyphenyl)-1H-pyrazolo[3,4-d]pyrimidin-1-yl)pyrrolidin-1-yl)-2-oxoethylcarbamate

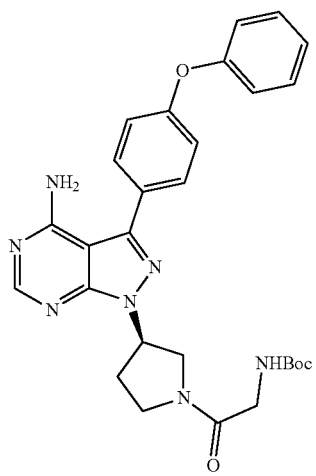 [SMILES: CC(C)(C)OC(=O)NCC(=O)N1CC[C@@H](n2nc(-c3ccc(Oc4ccccc4)cc3)c3c(N)ncnc32)C1]

The synthesis of Compound 66 was accomplished by using a procedure similar to that described in Example 1. Exact Mass (calculated): 529.24; MS(ESI) m/z(M+1)$^+$: 530.2427.

Example 67

Synthesis of Compound 67

(R)-1-(1-(methylsulfonyl)pyrrolidin-3-yl)-3-(4-phenoxyphenyl)-1H-pyrazolo[3,4-d]pyrimidin-4-amine

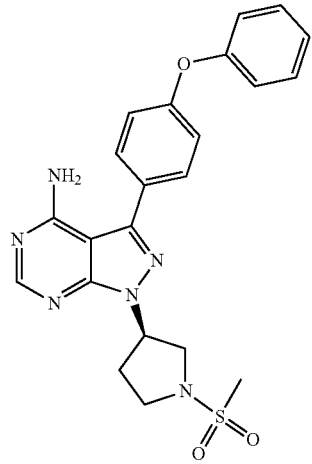 [SMILES: CS(=O)(=O)N1CC[C@@H](n2nc(-c3ccc(Oc4ccccc4)cc3)c3c(N)ncnc32)C1]

The synthesis of Compound 67 was accomplished by using a procedure similar to that described in Example 1. Exact Mass (calculated): 450.15; MS(ESI) m/z(M+1)$^+$: 451.1527.

Example 68

Synthesis of Compound 68

(4-(4-amino-(4-phenoxyphenyl)-1H-pyrazolo[3,4-d]pyrimidin-1-yl)piperidin-1-yl)(1-methylpiperidin-4-yl)methanone

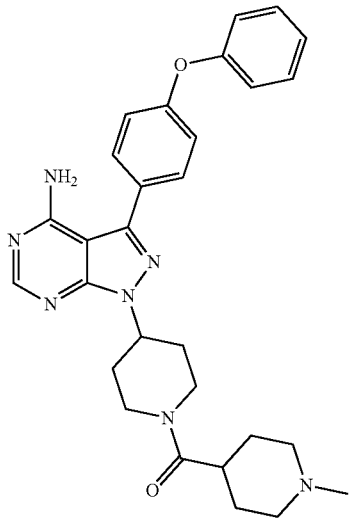 [SMILES: CN1CCC(C(=O)N2CCC(n3nc(-c4ccc(Oc5ccccc5)cc4)c4c(N)ncnc43)CC2)CC1]

Scheme II

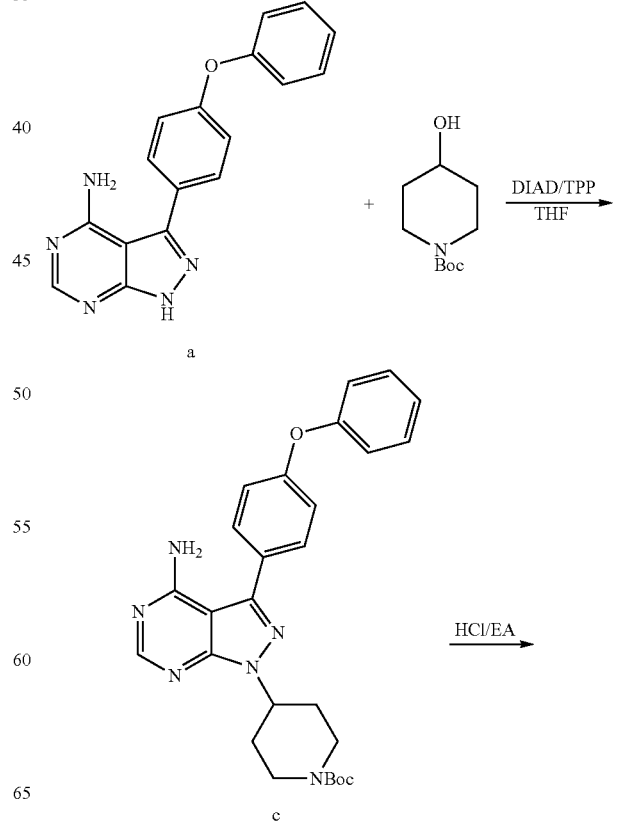

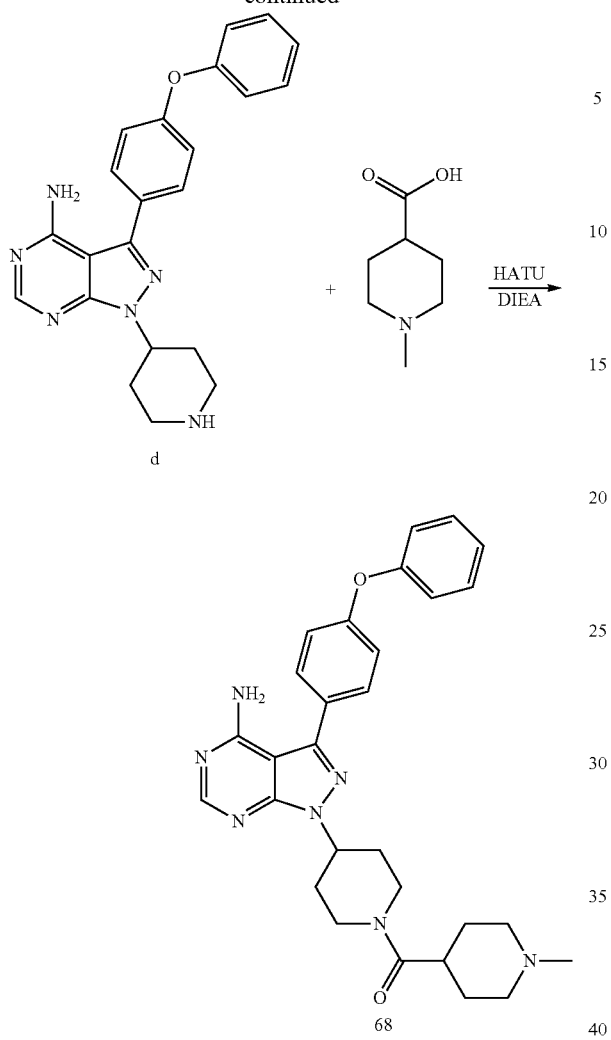

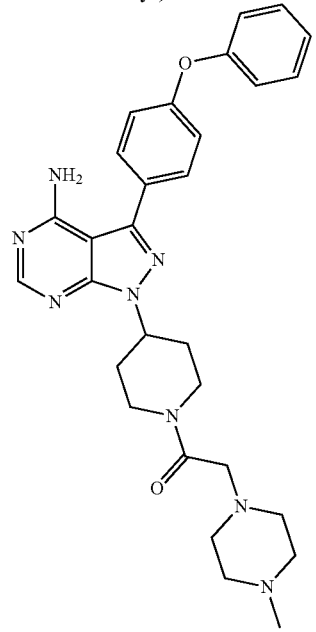 [SMILES: CN1CCN(CC(=O)N2CCC(n3nc(-c4ccc(Oc5ccccc5)cc4)c4c(N)ncnc43)CC2)CC1]

Example 69

Synthesis of Compound 69

1-(4-(4-amino-(4-phenoxyphenyl)-1H-pyrazolo[3,4-d]pyrimidin-1-yl)piperidin-1-yl)-2-(4-methylpiperazin-1-yl)ethanone The synthesis of Compound 69 was accomplished by using a procedure similar to that described in Example 68. Exact Mass (calculated): 526.63; MS(ESI) m/z(M+1)$^+$: 527.6329.

Example 70

Synthesis of Compound 70

1-(4-(4-amino-(4-phenoxyphenyl)-1H-pyrazolo[3,4-d]pyrimidin-1-yl) piperidin-1-yl)-2-morpholinoethanone

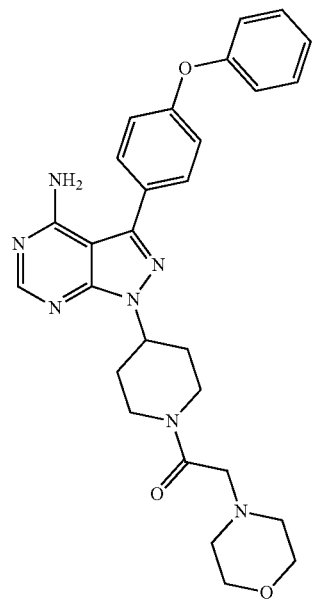 [SMILES: Nc1ncnc2c1c(-c1ccc(Oc3ccccc3)cc1)nn2C1CCN(C(=O)CN2CCOCC2)CC1]

The synthesis of Compound 70 was accomplished by using a procedure similar to that described in Example 68. Exact Mass (calculated): 513.59; MS(ESI) m/z(M+1)$^+$: 514.5917.

As shown in Scheme II, the synthesis of Compound 68 was accomplished by the synthesis from a to c by using a method similar to that described in Example 1 except that (S)-N-tert-butoxycarbonyl-3-piperidinol was replaced by N-tert-butoxycarbonyl-4-piperidinol as the starting material. The compound c was dissolved in methylene chloride and trifluoroacetic acid was added. The mixture was stirred at room temperature for 2 hours. After concentration, ethyl acetate and water-soluble potassium carbonate was added to the residue. The organic phase was dried, concentrated by filtration, and 4.0 M HCl in 4-dioxane solution was added under stirring, the solid was collected and was washed with ethyl acetate. The solid was then dissolved in a solution of ethyl acetate and potassium carbonate. The organic phase was dried and was concentrated to obtain intermediate d. The compound d (20 mg, 0.05 mmol) was dissolved in N, N-dimethylformamide (2 ml). 1-methylpiperidin-4-carboxylic acid (7.4 mg, 0.05 mmol), di isopropylethylamine (7.4 mg, 0.05 mmol), HATU (21.6 mg, 0.05 mmol) was added. The mixture was stirred at room temperature for 0.5 hour, then was diluted with ethyl acetate, washed with water, dried and concentrated by column chromatography to obtain 12 mg of white solid compound 68. Exact Mass (calculated): 511.62; MS(ESI) m/z(M+1)$^+$: 512.6227.

Example 71

Synthesis of Compound 71

(4-(4-amino-(4-phenoxyphenyl)-1H-pyrazolo[3,4-d]pyrimidin-1-yl)piperidin-1-yl)(4-((4-methylpiperazin-1-yl)methyl)phenyl)methanone

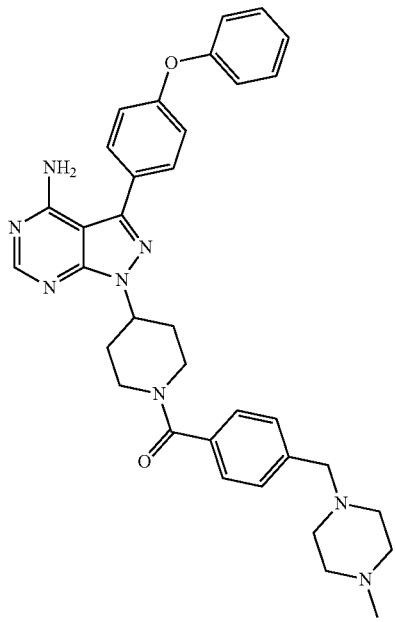 [SMILES: CN1CCN(Cc2ccc(C(=O)N3CCC(n4nc(-c5ccc(Oc6ccccc6)cc5)c5c(N)ncnc54)CC3)cc2)CC1]

The synthesis of Compound 71 was accomplished by using a procedure similar to that described in Example 68. Exact Mass (calculated): 602.73; MS(ESI) m/z(M+1)$^+$: 603.7325.

Example 72

Synthesis of Compound 72

1-(4-(4-amino-(4-phenoxyphenyl)-1H-pyrazolo[3,4-d]pyrimidin-1-yl) piperidin-1-yl)-2-(dimethylamino)ethanone

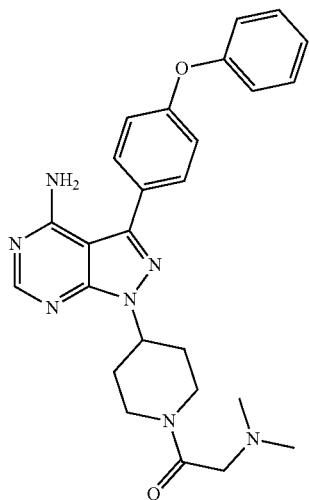 [SMILES: CN(C)CC(=O)N1CCC(n2nc(-c3ccc(Oc4ccccc4)cc3)c3c(N)ncnc32)CC1]

The synthesis of Compound 72 was accomplished by using a procedure similar to that described in Example 68. Exact Mass (calculated): 471.55; MS(ESI) m/z(M+1)$^+$: 472.5532.

Example 73

Synthesis of Compound 73

1-(1-(methylsulfonyl)piperidin-4-yl)-3-(4-phenoxyphenyl)-1H-pyrazolo[3,4-d]pyrimidin-4-amine

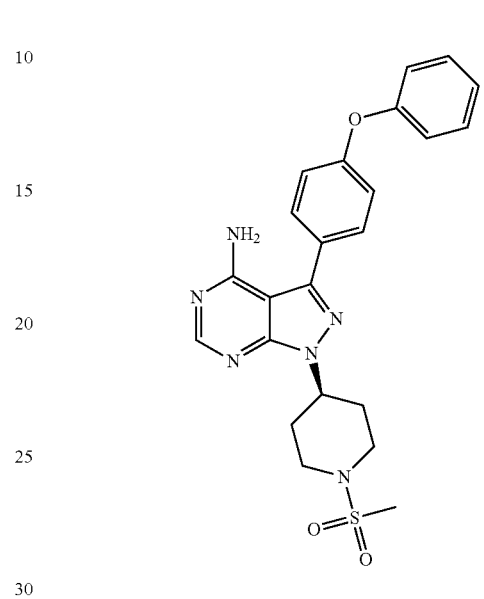

The synthesis of Compound 73 was accomplished by using a procedure similar to that described in Example 68. Exact Mass (calculated): 464.54; MS(ESI) m/z(M+1)$^+$: 465.5423.

Example 74

Synthesis of Compound 74

(R)-2-amino-1-(4-(4-amino-(4-phenoxyphenyl)-1H-pyrazolo[3,4-d]pyrimidin-1-yl)piperidin-1-yl)-4-methylpentan-1-one

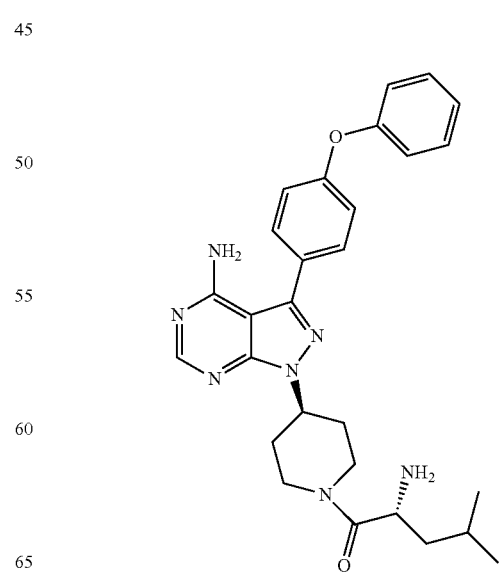

The synthesis of Compound 74 was accomplished by using a procedure similar to that described in Example 68. Exact Mass (calculated): 499.61; MS(ESI) m/z(M+1)+: 500.6128.

Example 75

Synthesis of Compound 75

1-(4-(4-amino-(4-phenoxyphenyl)-1H-pyrazolo[3,4-d]pyrimidin-1-yl) piperidin-1-yl)-2-(methylamino) ethanone

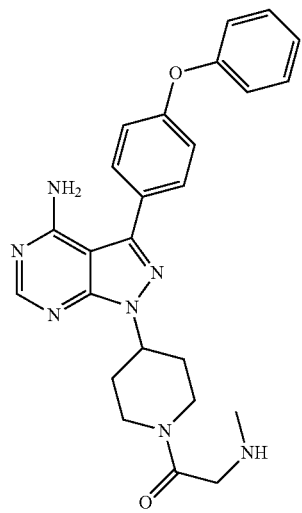 [SMILES: CNCC(=O)N1CCC(n2nc(-c3ccc(Oc4ccccc4)cc3)c3c(N)ncnc32)CC1]

The synthesis of Compound 75 was accomplished by using a procedure similar to that described in Example 68. Exact Mass (calculated): 457.53; MS(ESI) m/z(M+1)+: 458.5316.

Example 76

Synthesis of Compound 76

N-(4-(4-amino-3-(4-phenoxyphenyl)-1H-pyrazolo[3,4-d]pyrimidin-1-yl)cyclohexyl)-2-(dimethylamino) acetamide

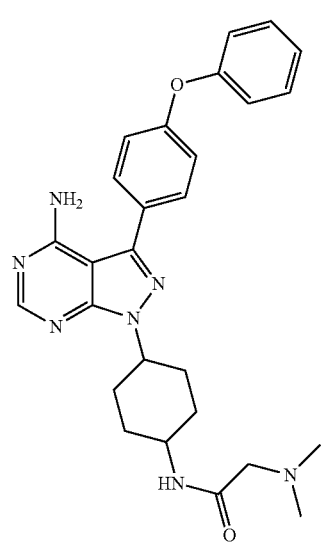 [SMILES: CN(C)CC(=O)NC1CCC(n2nc(-c3ccc(Oc4ccccc4)cc3)c3c(N)ncnc32)CC1]

Scheme III

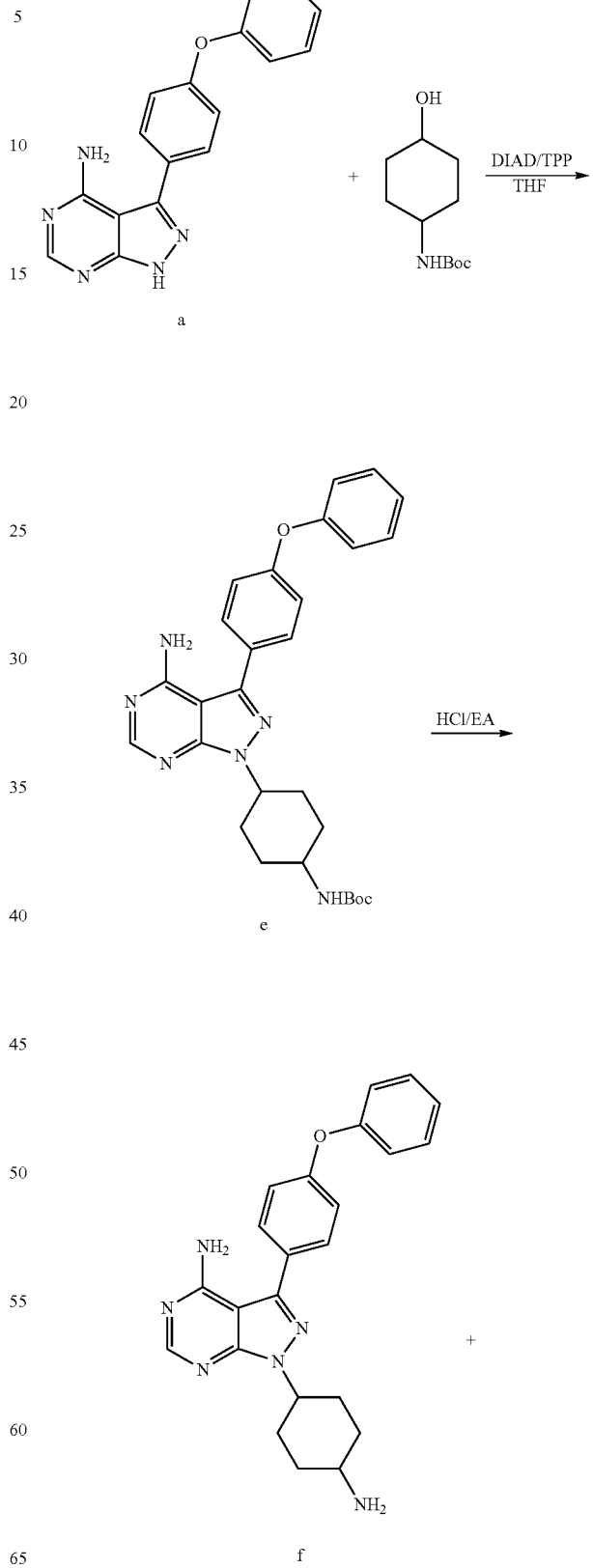

159
-continued

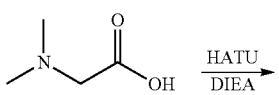

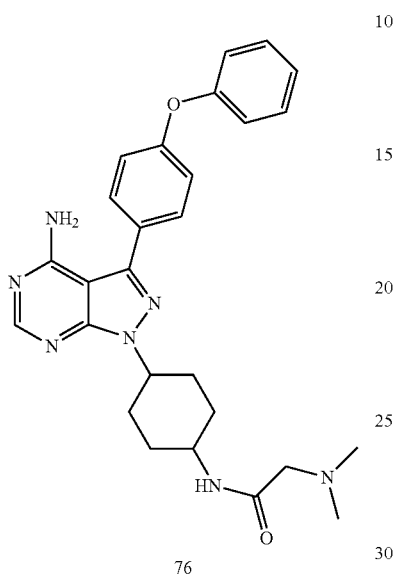

76

As shown in Scheme II, the synthesis of Compound 76 was accomplished by the synthesis from a to e by using a method similar to that described in Example 1 except that (S)-N-tert-butoxycarbonyl-3-piperidinol was replaced by N-Boc-4-aminocyclohexanol as the starting material. The compound e was dissolved in methylene chloride and trifluoroacetic acid was added. The mixture was stirred at room temperature for 2 hours. After concentration, ethyl acetate and water-soluble potassium carbonate was added to the residue. The organic phase was dried, concentrated by filtration, and 4.0 M HCl in 4-dioxane solution was added under stifling, the solid was collected and was washed with ethyl acetate. The solid was then dissolved in a solution of ethyl acetate and potassium carbonate. The organic phase was dried and was concentrated to obtain intermediate f. The compound f (20 mg, 0.05 mmol) was dissolved in N,N-dimethylformamide (2 ml). 2-(dimethylamino)acetic acid (5.1 mg, 0.05 mmol), di isopropylethylamine (7.4 mg, 0.05 mmol), HATU (21.6 mg, 0.05 mmol) was added. The mixture was stirred at room temperature for 0.5 hour, then was diluted with ethyl acetate, washed with water, dried and concentrated by column chromatography to obtain 16 mg of white solid compound 76. Exact Mass (calculated): 485.58; MS(ESI) m/z(M+1)$^+$: 486.5816.

160

Example 77

Synthesis of Compound 77

(R)-2-amino-N-(4-(4-amino-3-(4-phenoxyphenyl)-1H-pyrazolo[3,4-d]pyrimidin-1-yl)cyclohexyl)-4-methylpentanamide hydrochloride

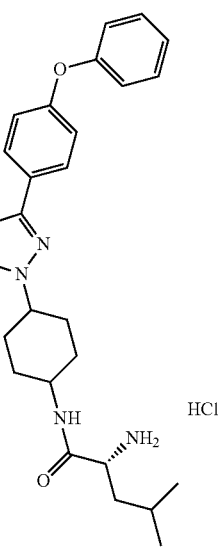

The synthesis of Compound 77 was accomplished by using a procedure similar to that described in Example 76. Exact Mass (calculated): 513.64; MS(ESI) m/z(M+1)$^+$: 514.6423.

Example 78

Synthesis of Compound 78

N-(4-(4-amino-3-(4-phenoxyphenyl)-1H-pyrazolo[3,4-d]pyrimidin-1-yl)cyclohexyl)methanesulfonamide

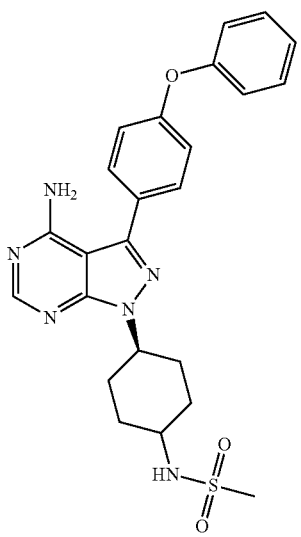

The synthesis of Compound 78 was accomplished by using a procedure similar to that described in Example 76. Exact Mass (calculated): 478.57; MS(ESI) m/z(M+1)⁺: 479.5717.

Example 79

Synthesis of Compound 79

N-(4-(4-amino-3-(4-phenoxyphenyl)-1H-pyrazolo[3,4-d]pyrimidin-1-yl)cyclohexyl)-2-(methylamino)acetamide

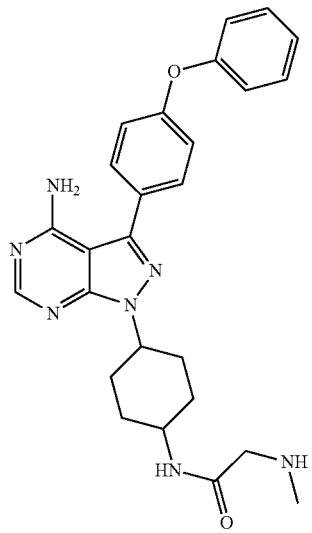

The synthesis of Compound 79 was accomplished by using a procedure similar to that described in Example 76. Exact Mass (calculated): 471.55; MS(ESI) m/z(M+1)⁺: 472.5521.

Example 80

Synthesis of Compound 80

N-(4-(4-amino-3-(4-phenoxyphenyl)-1H-pyrazolo[3,4-d]pyrimidin-1-yl)cyclohexyl)-1-methylaminopiperidin-4-carboxamide

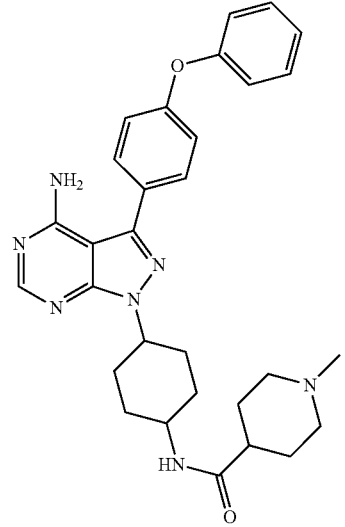 [SMILES: CN1CCC(C(=O)NC2CCC(n3nc(-c4ccc(Oc5ccccc5)cc4)c4c(N)ncnc43)CC2)CC1]

The synthesis of Compound 80 was accomplished by using a procedure similar to that described in Example 76. Exact Mass (calculated): 525.64; MS(ESI) m/z(M+1)⁺: 526.6422.

Example 81

Synthesis of Compound 81

N-(4-(4-amino-3-(4-phenoxyphenyl)-1H-pyrazolo[3,4-d]pyrimidin-1-yl)cyclohexyl)-2-(4-methylpiperazin-1-yl)acetamide

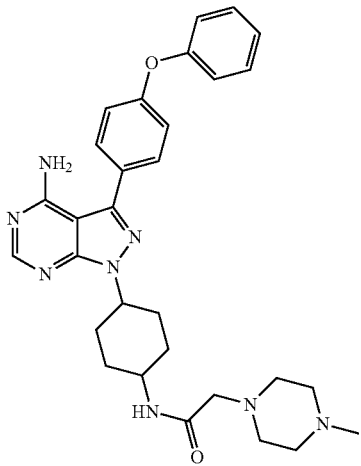 [SMILES: CN1CCN(CC(=O)NC2CCC(n3nc(-c4ccc(Oc5ccccc5)cc4)c4c(N)ncnc43)CC2)CC1]

The synthesis of Compound 81 was accomplished by using a procedure similar to that described in Example 76. Exact Mass (calculated): 540.66; MS(ESI) m/z(M+1)⁺: 541.6625.

Example 82

Synthesis of Compound 82

N-(4-(4-amino-3-(4-phenoxyphenyl)-1H-pyrazolo[3,4-d]pyrimidin-1-yl)cyclohexyl)-2-morpholinoacetamide

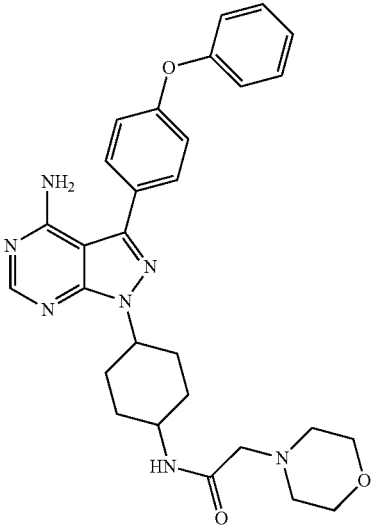 [SMILES: Nc1ncnc2c1c(-c1ccc(Oc3ccccc3)cc1)nn2C1CCC(NC(=O)CN2CCOCC2)CC1]

The synthesis of Compound 82 was accomplished by using a procedure similar to that described in Example 76. Exact Mass (calculated): 527.62; MS(ESI) m/z(M+1)⁺: 528.6223.

Example 83

Synthesis of Compound 83

N-(4-(4-amino-3-(4-phenoxyphenyl)-1H-pyrazolo[3,4-d]pyrimidin-1-yl)cyclohexyl)-2-cyanoacetamide

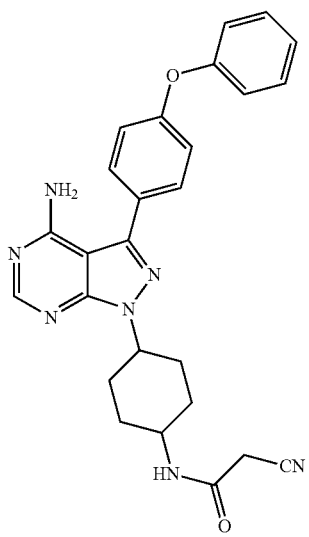 [SMILES: N#CCC(=O)NC1CCC(n2nc(-c3ccc(Oc4ccccc4)cc3)c3c(N)ncnc32)CC1]

The synthesis of Compound 83 was accomplished by using a procedure similar to that described in Example 76. Exact Mass (calculated): 467.52; MS(ESI) m/z(M+1)⁺: 468.5218.

Example 84

Synthesis of Compound 84

(R)-2-amino-N-(4-(4-amino-3-(4-phenoxyphenyl)-1H-pyrazolo[3,4-d]pyrimidin-1-yl)cis-1,4-cyclohexyl)-4-methylpentanamide hydrochloride

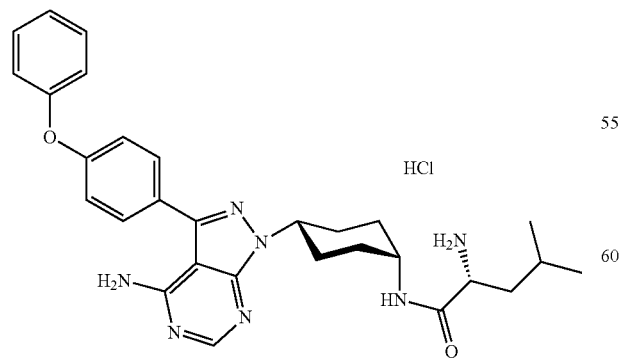

The synthesis of Compound 84 was accomplished by using a procedure similar to that described in Example 76 except that N-Boc-4-aminocyclohexanol was replaced by trans-4-Boc-aminocyclohexanol as the starting material. Exact Mass (calculated): 513.64; MS(ESI) m/z(M+1)⁺: 514.6424.

Example 85

Synthesis of Compound 85

(R)-2-amino-N-(4-(4-amino-3-(4-phenoxyphenyl)-1H-pyrazolo[3,4-d]pyrimidin-1-yl)trans-1,4-cyclohexyl)-4-methylpentanamide hydrochloride

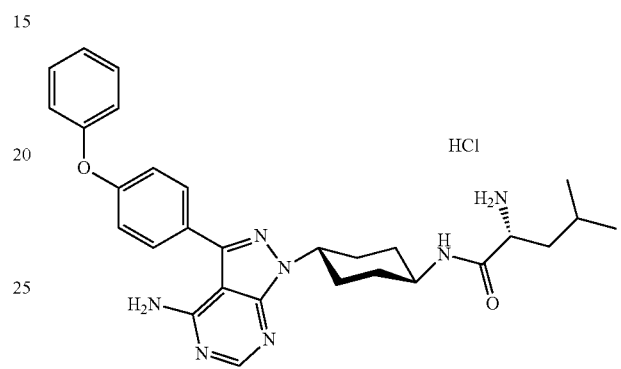

The synthesis of Compound 85 was accomplished by using a procedure similar to that described in Example 76 except that N-Boc-4-aminocyclohexanol was replaced by cis-4-Boc-aminocyclohexanol as the starting material. Exact Mass (calculated): 513.64; MS(ESI) m/z(M+1)⁺: 514.6425.

Example 86

Synthesis of Compound 86

(R)-2-amino-N-(4-(4-amino-(4-phenoxyphenyl)-1H-pyrazolo[3,4-d]pyrimidin-1-yl)cyclohexyl)-3-methylbutanamide hydrochloride

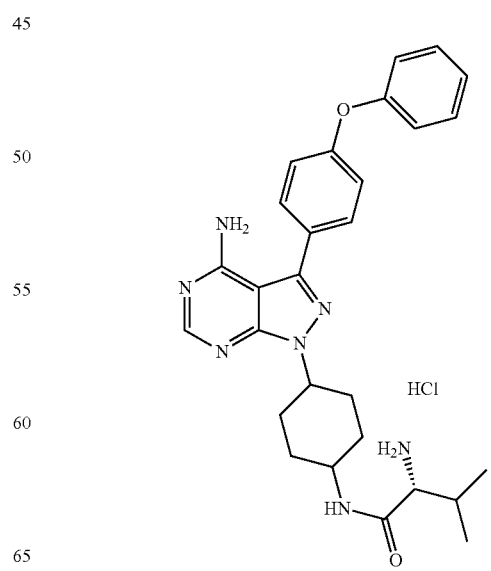

The synthesis of Compound 86 was accomplished by using a procedure similar to that described in Example 76. Exact Mass (calculated): 499.61; MS(ESI) m/z(M+1)⁺: 500.2785.

Example 87

Synthesis of Compound 87

(R)-N-(4-(4-amino-(4-phenoxyphenyl)-1H-pyrazolo[3,4-d]pyrimidin-1-yl)cyclohexyl)-3-methyl-2-(methylamino)butanamide hydrochloride

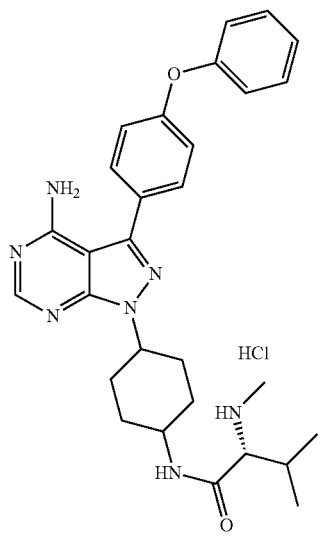 [SMILES: CN[C@@H](C(=O)NC1CCC(n2nc(-c3ccc(Oc4ccccc4)cc3)c3c(N)ncnc32)CC1)C(C)C ; Cl]

The synthesis of Compound 87 was accomplished by using a procedure similar to that described in Example 76. Exact Mass (calculated): 513.63; MS(ESI) m/z(M+1)⁺: 514.2985.

Example 88

Synthesis of Compound 88

(R)-N-(4-(4-amino-(4-phenoxyphenyl)-1H-pyrazolo[3,4-d]pyrimidin-1-yl)cyclohexyl)-2-(dimethylamino)-3-methylbutanamide

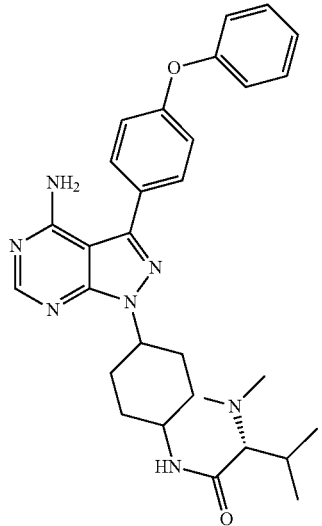 [SMILES: CC(C)[C@H](C(=O)NC1CCC(n2nc(-c3ccc(Oc4ccccc4)cc3)c3c(N)ncnc32)CC1)N(C)C]

The synthesis of Compound 88 was accomplished by using a procedure similar to that described in Example 76. Exact Mass (calculated): 527.66; MS(ESI) m/z(M+1)⁺: 528.3065.

Example 89

Synthesis of Compound 89

(S)-2-amino-N-(4-(4-amino-(4-phenoxyphenyl)-1H-pyrazolo[3,4-d]pyrimidin-1-yl)cyclohexyl)-3-methylbutanamide hydrochloride

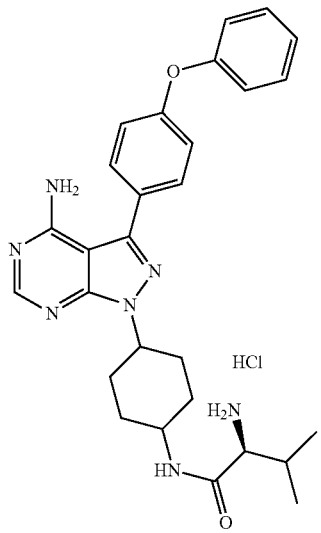 [SMILES: CC(C)[C@H](N)C(=O)NC1CCC(n2nc(-c3ccc(Oc4ccccc4)cc3)c3c(N)ncnc32)CC1 ; Cl]

The synthesis of Compound 89 was accomplished by using a procedure similar to that described in Example 76. Exact Mass (calculated): 499.61; MS(ESI) m/z(M+1)+: 500.2787.

Example 90

Synthesis of Compound 90

(S)-N-(4-(4-amino-(4-phenoxyphenyl)-1H-pyrazolo[3,4-d]pyrimidin-1-yl)cyclohexyl)-3-methyl-2-(methylamino)butanamide hydrochloride

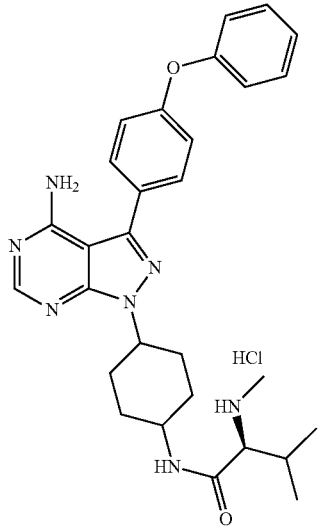 [SMILES: CN[C@H](C(=O)NC1CCC(n2nc(-c3ccc(Oc4ccccc4)cc3)c3c(N)ncnc32)CC1)C(C)C ; Cl]

The synthesis of Compound 90 was accomplished by using a procedure similar to that described in Example 76. Exact Mass (calculated): 513.63; MS(ESI) m/z(M+1)$^+$: 514.2986.

Example 91

Synthesis of Compound 91

(S)-N-(4-(4-amino-(4-phenoxyphenyl)-1H-pyrazolo[3,4-d]pyrimidin-1-yl)cyclohexyl)-2-(dimethylamino)-3-methylbutanamide

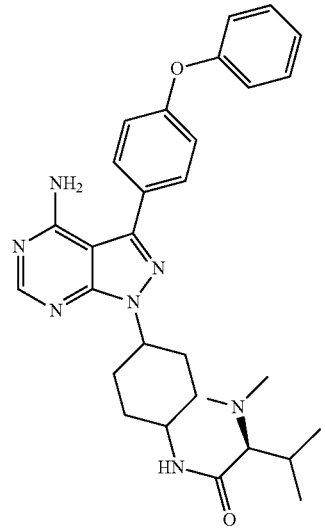 [SMILES: CC(C)[C@@H](C(=O)NC1CCC(n2nc(-c3ccc(Oc4ccccc4)cc3)c3c(N)ncnc32)CC1)N(C)C]

The synthesis of Compound 91 was accomplished by using a procedure similar to that described in Example 76. Exact Mass (calculated): 527.66; MS(ESI) m/z(M+1)$^+$: 528.3067.

Example 92

Synthesis of Compound 92

(R)-N-(4-(4-amino-(4-phenoxyphenyl)-1H-pyrazolo[3,4-d]pyrimidin-1-yl)cyclohexyl)-4-methyl-2-(methylamino)pentanamide hydrochloride

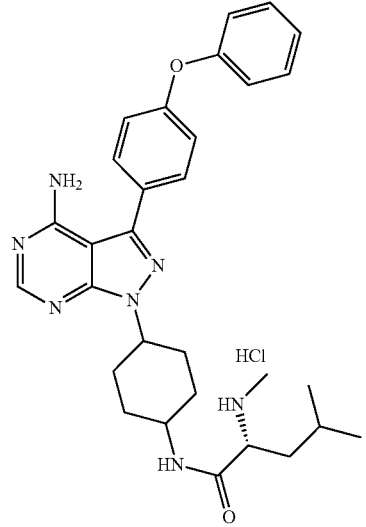 [SMILES: CN[C@H](CC(C)C)C(=O)NC1CCC(n2nc(-c3ccc(Oc4ccccc4)cc3)c3c(N)ncnc32)CC1 ; Cl]

The synthesis of Compound 92 was accomplished by using a procedure similar to that described in Example 76. Exact Mass (calculated): 527.66; MS(ESI) m/z(M+1)$^+$: 528.3063.

Example 93

Synthesis of Compound 93

(R)-N-(4-(4-amino-(4-phenoxyphenyl)-1H-pyrazolo[3,4-d]pyrimidin-1-yl)cyclohexyl)-2-(dimethylamino)-4-methylpentanamide

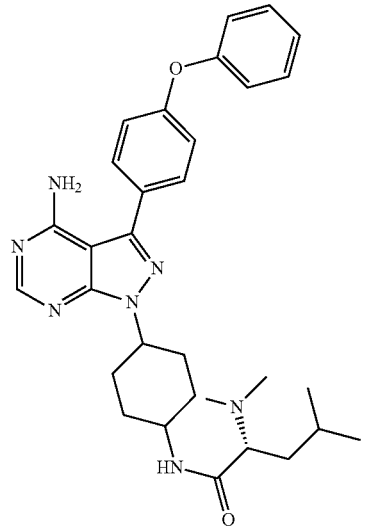 [SMILES: CC(C)C[C@H](C(=O)NC1CCC(n2nc(-c3ccc(Oc4ccccc4)cc3)c3c(N)ncnc32)CC1)N(C)C]

The synthesis of Compound 93 was accomplished by using a procedure similar to that described in Example 76. Exact Mass (calculated): 541.69; MS(ESI) m/z(M+1)$^+$: 542.3263.

Example 94

Synthesis of Compound 94

(S)-2-amino-N-(4-(4-amino-(4-phenoxyphenyl)-1H-pyrazolo[3,4-d]pyrimidin-1-yl)cyclohexyl)-4-methylpentanamide

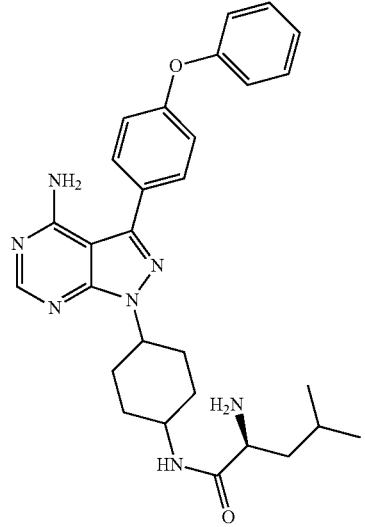 [SMILES: CC(C)C[C@H](N)C(=O)NC1CCC(n2nc(-c3ccc(Oc4ccccc4)cc3)c3c(N)ncnc32)CC1]

The synthesis of Compound 94 was accomplished by using a procedure similar to that described in Example 76. Exact Mass (calculated): 513.63; MS(ESI) m/z(M+1)+: 514.2963.

Example 95

Synthesis of Compound 95

(S)-N-(4-(4-amino-(4-phenoxyphenyl)-1H-pyrazolo[3,4-d]pyrimidin-1-yl)cyclohexyl)-4-methyl-2-(methylamino)pentanamide hydrochloride

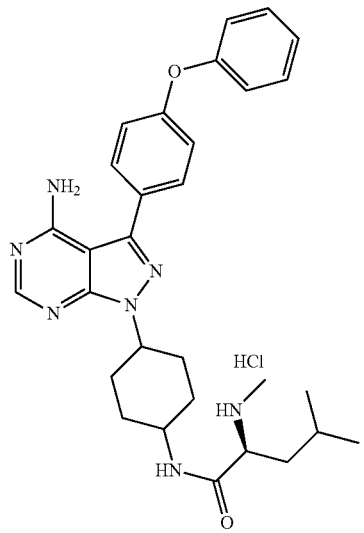 [SMILES: CN[C@@H](CC(C)C)C(=O)NC1CCC(n2nc(-c3ccc(Oc4ccccc4)cc3)c3c(N)ncnc32)CC1 ; Cl]

The synthesis of Compound 95 was accomplished by using a procedure similar to that described in Example 76. Exact Mass (calculated): 527.66; MS(ESI) m/z(M+1)+: 528.3065.

Example 96

Synthesis of Compound 96

(S)-N-(4-(4-amino-(4-phenoxyphenyl)-1H-pyrazolo[3,4-d]pyrimidin-1-yl)cyclohexyl)-2-(dimethylamino)-4-methylpentanamide

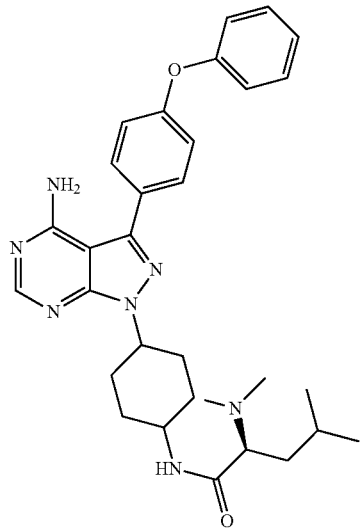 [SMILES: CC(C)C[C@@H](C(=O)NC1CCC(n2nc(-c3ccc(Oc4ccccc4)cc3)c3c(N)ncnc32)CC1)N(C)C]

The synthesis of Compound 96 was accomplished by using a procedure similar to that described in Example 76. Exact Mass (calculated): 541.69; MS(ESI) m/z(M+1)+: 542.3266.

Example 97

Synthesis of Compound 97

(R)-2-amino-N-(4-(4-amino-(4-phenoxyphenyl)-1H-pyrazolo[3,4-d]pyrimidin-1-yl)cyclohexyl)-butanamide hydrochloride

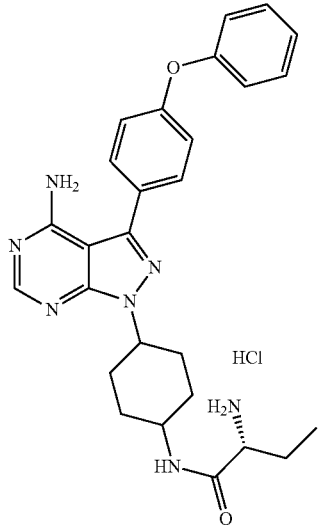 [SMILES: CC[C@@H](N)C(=O)NC1CCC(n2nc(-c3ccc(Oc4ccccc4)cc3)c3c(N)ncnc32)CC1 ; Cl]

The synthesis of Compound 97 was accomplished by using a procedure similar to that described in Example 76. Exact Mass (calculated): 485.58; MS(ESI) m/z(M+1)+: 486.2666.

Example 98

Synthesis of Compound 98

(R)-N-(4-(4-amino-(4-phenoxyphenyl)-1H-pyrazolo[3,4-d]pyrimidin-1-yl)cyclohexyl)-2-(methylamino)-butanamide hydrochloride

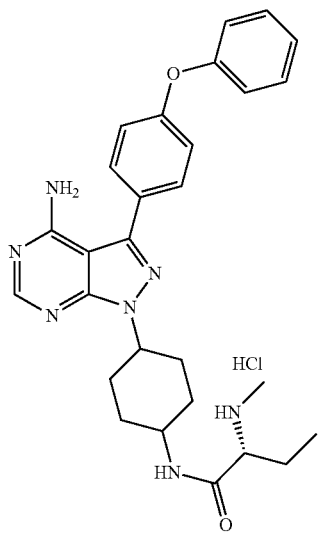 [SMILES: CC[C@@H](NC)C(=O)NC1CCC(n2nc(-c3ccc(Oc4ccccc4)cc3)c3c(N)ncnc32)CC1 ; Cl]

The synthesis of Compound 98 was accomplished by using a procedure similar to that described in Example 76. Exact Mass (calculated): 499.61; MS(ESI) m/z(M+1)+: 500.2766.

Example 99

Synthesis of Compound 99

(R)-N-(4-(4-amino-(4-phenoxyphenyl)-1H-pyrazolo[3,4-d]pyrimidin-1-yl)cyclohexyl)-2-(dimethylamino)butanamide

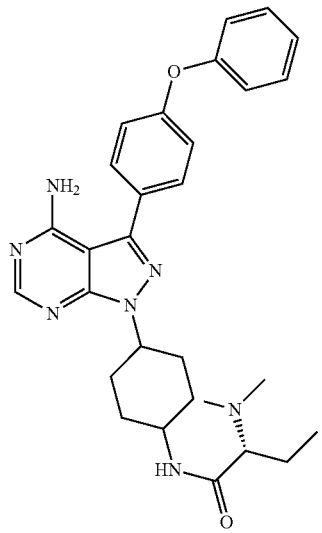 [SMILES: CC[C@H](C(=O)NC1CCC(n2nc(-c3ccc(Oc4ccccc4)cc3)c3c(N)ncnc32)CC1)N(C)C]

The synthesis of Compound 99 was accomplished by using a procedure similar to that described in Example 76. Exact Mass (calculated): 513.63; MS(ESI) m/z(M+1)+: 514.2966.

Example 100

Synthesis of Compound 100

(S)-2-amino-N-(4-(4-amino-(4-phenoxyphenyl)-1H-pyrazolo[3,4-d]pyrimidin-1-yl)cyclohexyl)-butanamide hydrochloride

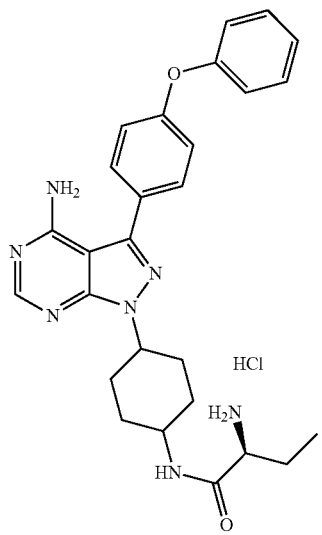 [SMILES: CC[C@H](N)C(=O)NC1CCC(n2nc(-c3ccc(Oc4ccccc4)cc3)c3c(N)ncnc32)CC1 ; Cl]

The synthesis of Compound 100 was accomplished by using a procedure similar to that described in Example 76. Exact Mass (calculated): 485.58; MS(ESI) m/z(M+1)+: 486.2669.

Example 101

Synthesis of Compound 101

(S)-N-(4-(4-amino-(4-phenoxyphenyl)-1H-pyrazolo[3,4-d]pyrimidin-1-yl)cyclohexyl)-2-(methylamino)butanamide hydrochloride

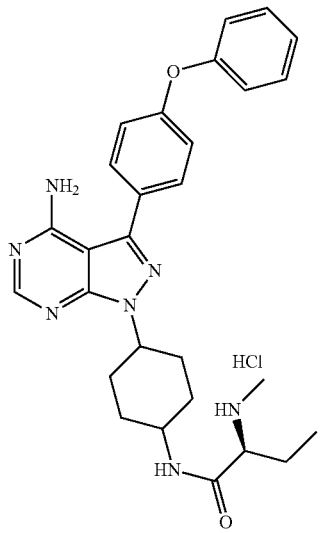 [SMILES: CC[C@H](NC)C(=O)NC1CCC(n2nc(-c3ccc(Oc4ccccc4)cc3)c3c(N)ncnc32)CC1 ; Cl]

The synthesis of Compound 101 was accomplished by using a procedure similar to that described in Example 76. Exact Mass (calculated): 499.61; MS(ESI) m/z(M+1)+: 500.2769.

Example 102

Synthesis of Compound 102

(S)-N-(4-(4-amino-(4-phenoxyphenyl)-1H-pyrazolo[3,4-d]pyrimidin-1-yl)cyclohexyl)-2-(dimethylamino)butanamide

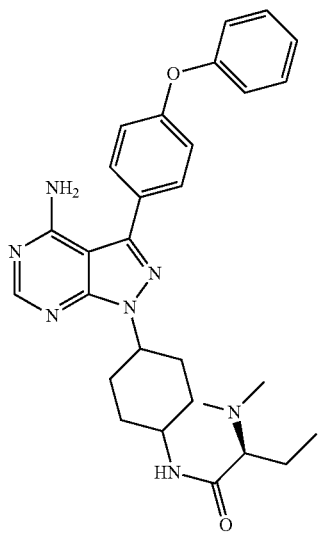 [SMILES: CC[C@@H](C(=O)NC1CCC(n2nc(-c3ccc(Oc4ccccc4)cc3)c3c(N)ncnc32)CC1)N(C)C]

The synthesis of Compound 102 was accomplished by using a procedure similar to that described in Example 76. Exact Mass (calculated): 513.63; MS(ESI) m/z(M+1)+: 514.2963.

Example 103

Synthesis of Compound 103

(R)-2-amino-N-(4-(4-amino-(4-phenoxyphenyl)-1H-pyrazolo[3,4-d]pyrimidin-1-yl)cyclohexyl)-pentanamide hydrochloride

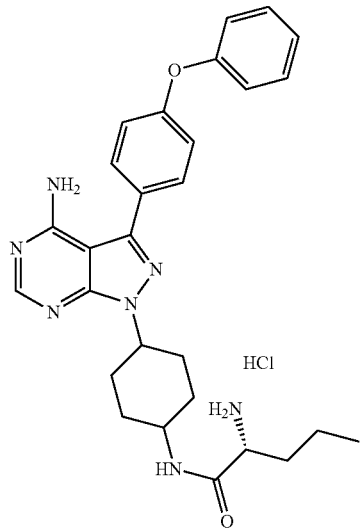 [SMILES: CCC[C@@H](N)C(=O)NC1CCC(n2nc(-c3ccc(Oc4ccccc4)cc3)c3c(N)ncnc32)CC1 ; Cl]

The synthesis of Compound 103 was accomplished by using a procedure similar to that described in Example 76. Exact Mass (calculated): 499.61; MS(ESI) m/z(M+1)+: 500.2763.

Example 104

Synthesis of Compound 104

(R)-N-(4-(4-amino-(4-phenoxyphenyl)-1H-pyrazolo[3,4-d]pyrimidin-1-yl)cyclohexyl)-2-(methylamino)-pentanamide hydrochloride

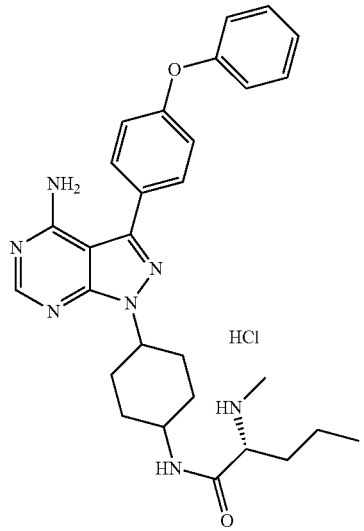 [SMILES: CCC[C@@H](NC)C(=O)NC1CCC(n2nc(-c3ccc(Oc4ccccc4)cc3)c3c(N)ncnc32)CC1 ; Cl]

The synthesis of Compound 104 was accomplished by using a procedure similar to that described in Example 76. Exact Mass (calculated): 513.63; MS(ESI) m/z(M+1)+: 514.2963.

Example 105

Synthesis of Compound 105

(R)-N-(4-(4-amino-(4-phenoxyphenyl)-1H-pyrazolo[3,4-d]pyrimidin-1-yl)cyclohexyl)-2-(dimethylamino)-pentanamide

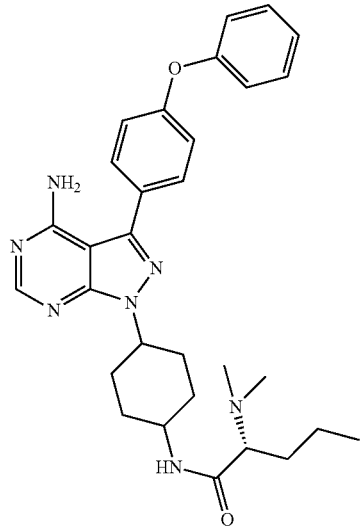 [SMILES: CCC[C@H](C(=O)NC1CCC(n2nc(-c3ccc(Oc4ccccc4)cc3)c3c(N)ncnc32)CC1)N(C)C]

The synthesis of Compound 105 was accomplished by using a procedure similar to that described in Example 76. Exact Mass (calculated): 527.66; MS(ESI) m/z(M+1)+: 528.3063.

Example 106

Synthesis of Compound 106

(S)-2-amino-N-(4-(4-amino-(4-phenoxyphenyl)-1H-pyrazolo[3,4-d]pyrimidin-1-yl)cyclohexyl)-pentanamide hydrochloride

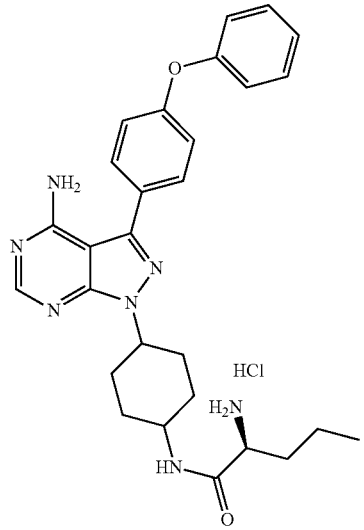 [SMILES: CCC[C@H](N)C(=O)NC1CCC(n2nc(-c3ccc(Oc4ccccc4)cc3)c3c(N)ncnc32)CC1 ; Cl]

The synthesis of Compound 106 was accomplished by using a procedure similar to that described in Example 76. Exact Mass (calculated): 499.61; MS(ESI) m/z(M+1)+: 500.2769.

Example 107

Synthesis of Compound 107

(S)-N-(4-(4-amino-(4-phenoxyphenyl)-1H-pyrazolo[3,4-d]pyrimidin-1-yl)cyclohexyl)-2-(methylamino)-pentanamide hydrochloride

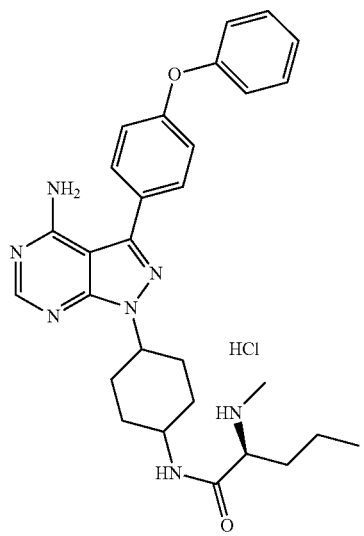 [SMILES: CCC[C@H](NC)C(=O)NC1CCC(n2nc(-c3ccc(Oc4ccccc4)cc3)c3c(N)ncnc32)CC1 ; Cl]

The synthesis of Compound 107 was accomplished by using a procedure similar to that described in Example 76. Exact Mass (calculated): 513.63; MS(ESI) m/z(M+1)+: 514.2971.

Example 108

Synthesis of Compound 108

(S)-N-(4-(4-amino-(4-phenoxyphenyl)-1H-pyrazolo[3,4-d]pyrimidin-1-yl)cyclohexyl)-2-(dimethylamino)-pentanamide

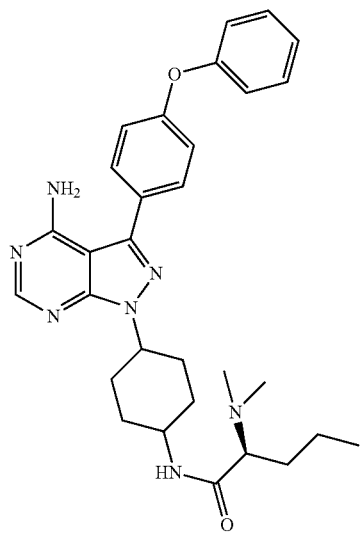 [SMILES: CCC[C@@H](C(=O)NC1CCC(n2nc(-c3ccc(Oc4ccccc4)cc3)c3c(N)ncnc32)CC1)N(C)C]

The synthesis of Compound 108 was accomplished by using a procedure similar to that described in Example 76. Exact Mass (calculated): 527.66; MS(ESI) m/z(M+1)+: 528.3068.

Example 109

Synthesis of Compound 109

(R)-2-amino-N-(4-(4-amino-3-(4-phenoxyphenyl)-1H-pyrazolo[3,4-d]pyrimidin-1-yl)cis-1,4-cyclohexyl)-4-methyl-2-(methylamino)pentanamide hydrochloride

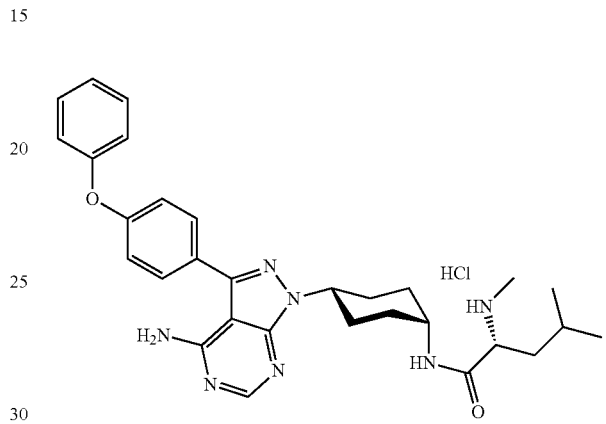

The synthesis of Compound 109 was accomplished by using a procedure similar to that described in Example 76 except that N-Boc-4-aminocyclohexanol was replaced by trans-4-Boc-aminocyclohexanol as the starting material. Exact Mass (calculated): 527.66; MS(ESI) m/z(M+1)+: 528.3074.

Example 110

Synthesis of Compound 110

(R)-2-amino-N-(4-(4-amino-3-(4-phenoxyphenyl)-1H-pyrazolo[3,4-d]pyrimidin-1-yl)cis-1,4-cyclohexyl)-4-methyl-2-(dimethylamino)pentanamide

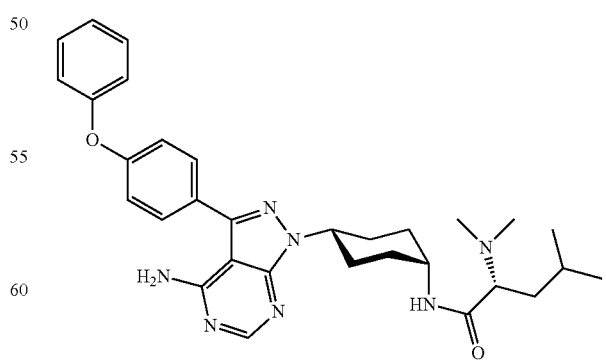

The synthesis of Compound 110 was accomplished by using a procedure similar to that described in Example 76 except that N-Boc-4-aminocyclohexanol was replaced by trans-4-Boc-aminocyclohexanol as the starting material. Exact Mass (calculated): 541.69; MS(ESI) m/z(M+1)⁺: 542.3274.

Example 111

Synthesis of Compound 111

(S)-2-amino-N-(4-(4-amino-3-(4-phenoxyphenyl)-1H-pyrazolo[3,4-d]pyrimidin-1-yl)cis-1,4-cyclohexyl)-4-methylpentanamide hydrochloride

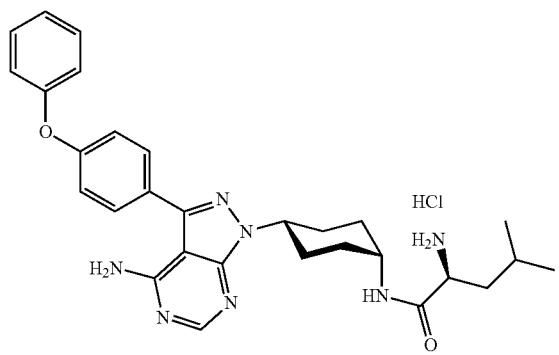

The synthesis of Compound 111 was accomplished by using a procedure similar to that described in Example 76 except that N-Boc-4-aminocyclohexanol was replaced by trans-4-Boc-aminocyclohexanol as the starting material. Exact Mass (calculated): 513.63; MS(ESI) m/z(M+1)+: 514.2974.

Example 112

Synthesis of Compound 112

(S)-2-amino-N-(4-(4-amino-3-(4-phenoxyphenyl)-1H-pyrazolo[3,4-d]pyrimidin-1-yl)cis-1,4-cyclohexyl)-4-methyl-2-(methylamino)pentanamide hydrochloride

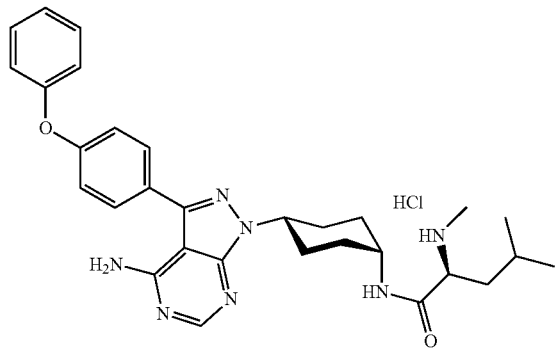

The synthesis of Compound 112 was accomplished by using a procedure similar to that described in Example 76 except that N-Boc-4-aminocyclohexanol was replaced by trans-4-Boc-aminocyclohexanol as the starting material. Exact Mass (calculated): 527.66; MS(ESI) m/z(M+1)⁺: 528.3074.

Example 113

Synthesis of Compound 113

(S)-2-amino-N-(4-(4-amino-3-(4-phenoxyphenyl)-1H-pyrazolo[3,4-d]pyrimidin-1-yl)cis-1,4-cyclohexyl)-4-methyl-2-(dimethylamino)pentanamide

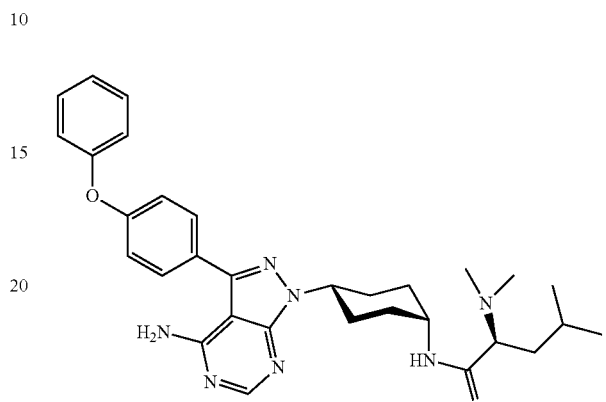

The synthesis of Compound 113 was accomplished by using a procedure similar to that described in Example 76 except that N-Boc-4-aminocyclohexanol was replaced by trans-4-Boc-aminocyclohexanol as the starting material. Exact Mass (calculated): 541.69; MS(ESI) m/z(M+1)⁺: 542.3277.

Example 114

Synthesis of Compound 114

(S)-2-amino-N-(4-(4-amino-3-(4-phenoxyphenyl)-1H-pyrazolo[3,4-d]pyrimidin-1-yl)trans-1,4-cyclohexyl)-4-methylpentanamide hydrochloride

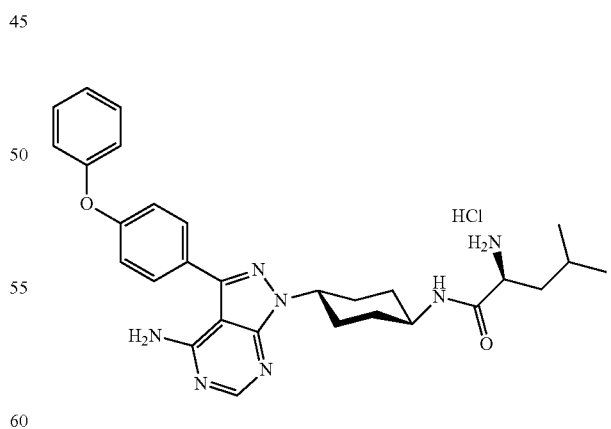

The synthesis of Compound 114 was accomplished by using a procedure similar to that described in Example 76 except that N-Boc-4-aminocyclohexanol was replaced by cis-4-Boc-aminocyclohexanol as the starting material. Exact Mass (calculated): 513.63; MS(ESI) m/z(M+1)+: 514.2976.

Example 115

Synthesis of Compound 115

(S)-2-amino-N-(4-(4-amino-3-(4-phenoxyphenyl)-1H-pyrazolo[3,4-d]pyrimidin-1-yl)trans-1,4-cyclohexyl)-4-methyl-2-(methylamino)pentanamide hydrochloride

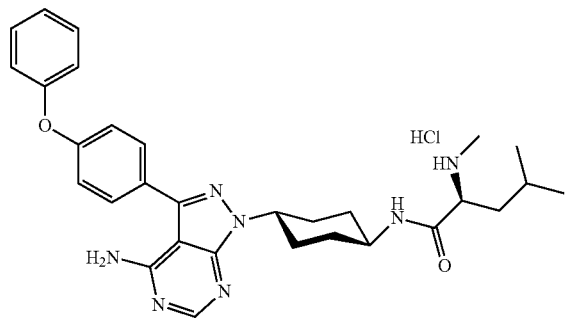

The synthesis of Compound 115 was accomplished by using a procedure similar to that described in Example 76 except that N-Boc-4-aminocyclohexanol was replaced by cis-4-Boc-aminocyclohexanol as the starting material. Exact Mass (calculated): 527.66; MS(ESI) m/z(M+1)$^+$: 528.3077.

Example 116

Synthesis of Compound 116

(S)-2-amino-N-(4-(4-amino-3-(4-phenoxyphenyl)-1H-pyrazolo[3,4-d]pyrimidin-1-yl)trans-1,4-cyclohexyl)-4-methyl-2-(dimethylamino)pentanamide

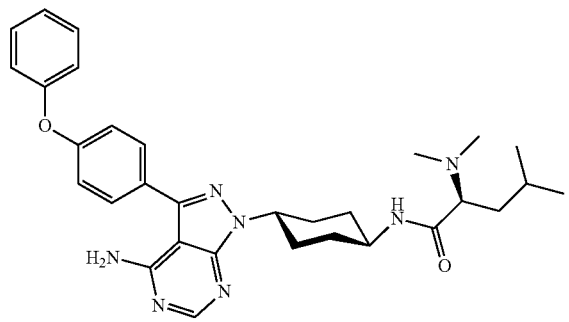

The synthesis of Compound 116 was accomplished by using a procedure similar to that described in Example 76 except that N-Boc-4-aminocyclohexanol was replaced by cis-4-Boc-aminocyclohexanol as the starting material. Exact Mass (calculated): 541.69; MS(ESI) m/z(M+1)+: 542.3280.

Example 117

Synthesis of Compound 117

(R)-2-amino-N-(4-(4-amino-3-(4-phenoxyphenyl)-1H-pyrazolo[3,4-d]pyrimidin-1-yl)trans-1,4-cyclohexyl)-4-methyl-2-(methylamino)pentanamide hydrochloride The synthesis of Compound 117 was accomplished by using a procedure similar to that described in Example 76 except that N-Boc-4-aminocyclohexanol was replaced by cis-4-Boc-aminocyclohexanol as the starting material. Exact Mass (calculated): 527.66; MS(ESI) m/z(M+1)$^+$: 528.3082.

Example 118

Synthesis of Compound 118

(R)-2-amino-N-(4-(4-amino-3-(4-phenoxyphenyl)-1H-pyrazolo[3,4-d]pyrimidin-1-yl)trans-1,4-cyclohexyl)-4-methyl-2-(dimethylamino)pentanamide

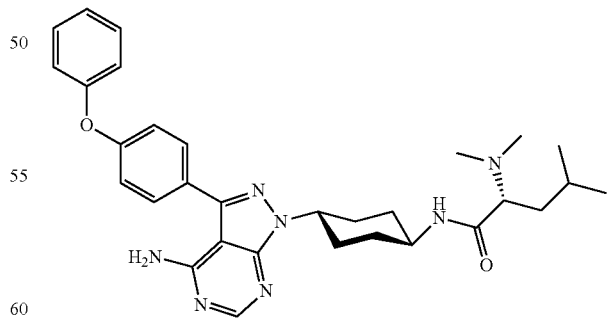

The synthesis of Compound 118 was accomplished by using a procedure similar to that described in Example 76 except that N-Boc-4-aminocyclohexanol was replaced by cis-4-Boc-aminocyclohexanol as the starting material. Exact Mass (calculated): 541.69; MS(ESI) m/z(M+1)$^+$: 542.3283.

Example 119

Synthesis of Compound 119

(R)-2-amino-N-(4-(4-amino-3-(4-phenoxyphenol)-1H-pyrazolo[3,4-d]pyrimidin-1-yl)cis-1,4-cyclohexyl)-2-(5-(tert-butyl)isoxazol-3-yl)acetamide hydrochloride

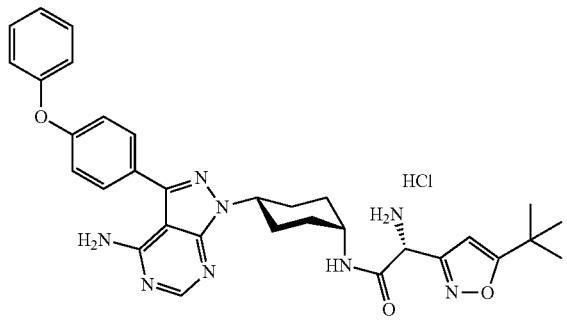

The synthesis of Compound 119 was accomplished by using a procedure similar to that described in Example 76 except that N-Boc-4-aminocyclohexanol was replaced by trans-4-Boc-aminocyclohexanol as the starting material. Exact Mass (calculated): 580.68; MS(ESI) m/z(M+1)$^+$: 581.2983.

Example 120

Synthesis of Compound 120

(R)-2-amino-N-(4-(4-amino-3-(4-phenoxyphenol)-1H-pyrazolo[3,4-d]pyrimidin-1-yl)cis-1,4-cyclohexyl)-2-(5-(tert-butyl)isoxazol-3-yl)-2-(methylamino)acetamide hydrochloride

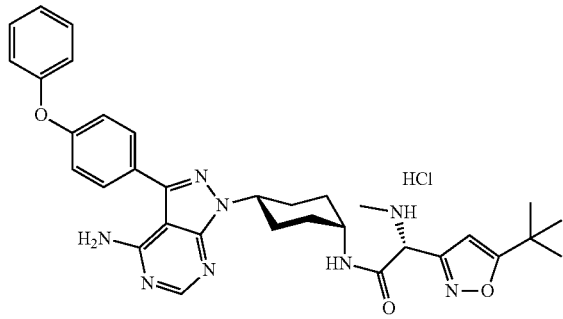

The synthesis of Compound 120 was accomplished by using a procedure similar to that described in Example 76 except that N-Boc-4-aminocyclohexanol was replaced by trans-4-Boc-aminocyclohexanol as the starting material. Exact Mass (calculated): 594.71; MS(ESI) m/z(M+1)$^+$: 595.3183.

Example 121

Synthesis of Compound 121

(R)-2-amino-N-(4-(4-amino-3-(4-phenoxyphenol)-1H-pyrazolo[3,4-d]pyrimidin-1-yl)cis-1,4-cyclohexyl)-2-(5-(tert-butyl)isoxazol-3-yl)-2-(dimethylamino)acetamide The synthesis of Compound 121 was accomplished by using a procedure similar to that described in Example 76 except that N-Boc-4-aminocyclohexanol was replaced by trans-4-Boc-aminocyclohexanol as the starting material. Exact Mass (calculated): 608.73; MS(ESI) m/z(M+1)$^+$: 609.3383.

Example 122

Synthesis of Compound 122

N-(4-(4-amino-3-(4-phenoxyphenol)-1H-pyrazolo[3,4-d]pyrimidin-1-yl)cis-1,4-cyclohexyl)-2-(5-(tert-butyl)isoxazol-3-yl)acetamide

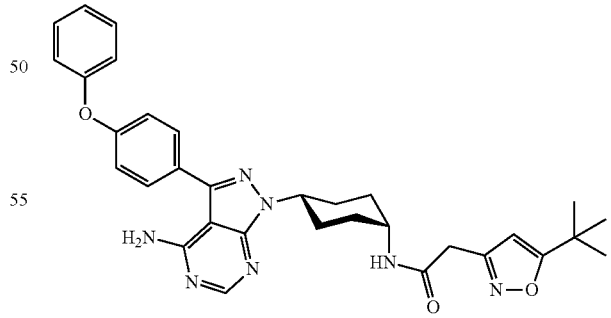

The synthesis of Compound 122 was accomplished by using a procedure similar to that described in Example 76 except that N-Boc-4-aminocyclohexanol was replaced by trans-4-Boc-aminocyclohexanol as the starting material. Exact Mass (calculated): 565.67; MS(ESI) m/z(M+1)$^+$: 566.2883.

Example 123

Synthesis of Compound 123

N-(4-(4-amino-3-(4-phenoxyphenol)-1H-pyrazolo[3,4-d]pyrimidin-1-yl)trans-1,4-cyclohexyl)-2-(5-(tert-butyl)isoxazol-3-yl)acetamide

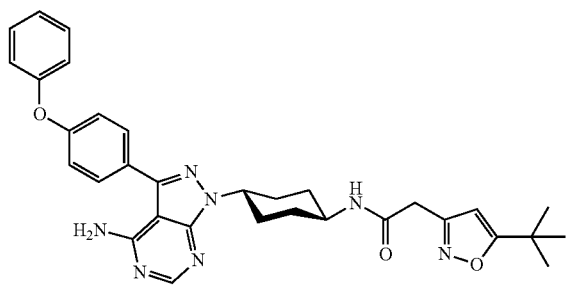

The synthesis of Compound 123 was accomplished by using a procedure similar to that described in Example 76 except that N-Boc-4-aminocyclohexanol was replaced by cis-4-Boc-aminocyclohexanol as the starting material. Exact Mass (calculated): 565.67; MS(ESI) m/z(M+1)$^+$: 566.2886.

Example 124

Synthesis of Compound 124

(S)-2-amino-N-(4-(4-amino-3-(4-phenoxyphenol)-1H-pyrazolo[3,4-d]pyrimidin-1-yl)trans-1,4-cyclohexyl)-2-(5-(tert-butyl)isoxazol-3-yl)acetamide hydrochloride

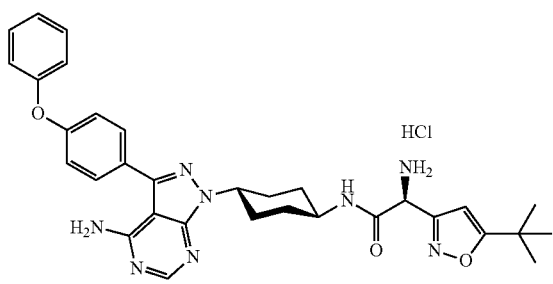

The synthesis of Compound 124 was accomplished by using a procedure similar to that described in Example 76 except that N-Boc-4-aminocyclohexanol was replaced by cis-4-Boc-aminocyclohexanol as the starting material. Exact Mass (calculated): 580.68; MS(ESI) m/z(M+1)$^+$: 581.2988.

Example 125

Synthesis of Compound 125

(S)-2-amino-N-(4-(4-amino-3-(4-phenoxyphenol)-1H-pyrazolo[3,4-d]pyrimidin-1-yl)trans-1,4-cyclohexyl)-2-(5-(tert-butyl)isoxazol-3-yl)-2-(methylamino)acetamide hydrochloride

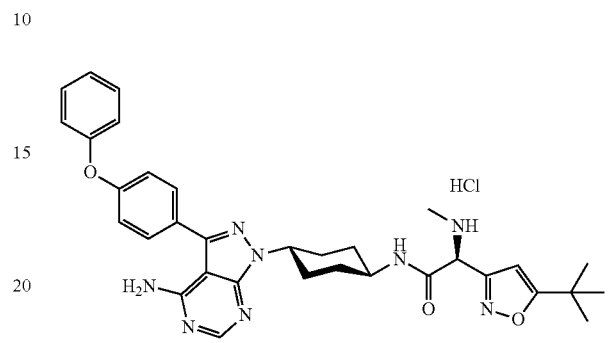

The synthesis of Compound 125 was accomplished by using a procedure similar to that described in Example 76 except that N-Boc-4-aminocyclohexanol was replaced by cis-4-Boc-aminocyclohexanol as the starting material. Exact Mass (calculated): 594.71; MS(ESI) m/z(M+1)$^+$: 595.3187.

Example 126

Synthesis of Compound 126

(S)-2-amino-N-(4-(4-amino-3-(4-phenoxyphenol)-1H-pyrazolo[3,4-d]pyrimidin-1-yl)trans-1,4-cyclohexyl)-2-(5-(tert-butyl)isoxazol-3-yl)-2-(dimethylamino)acetamide

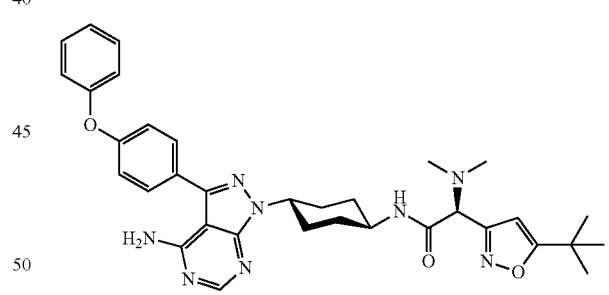

The synthesis of Compound 126 was accomplished by using a procedure similar to that described in Example 76 except that N-Boc-4-aminocyclohexanol was replaced by cis-4-Boc-aminocyclohexanol as the starting material. Exact Mass (calculated): 608.73; MS(ESI) m/z(M+1)$^+$: 609.3390.

Example 127

Effect on Proliferation of Cancer Cells

By examining the effect of the compounds of the present invention on the growth of cancer cells (Table 2), the inhibitory effect of the compounds on the proliferation of cancer cells and its selectivity to inhibition of cancer cell proliferation was further evaluated. In this Example, human acute monocytic leukemia cell lines MV4-11 (expressing FLT3/ITD mutant gene), human acute myeloid leukemia cell lines MOLM-13 (expressing FLT3/ITD mutant gene and wild-type FLT3 gene), human acute myeloid leukemia cell lines MOLM-14 (expressing FLT3/ITD mutant gene and wild-type FLT3 gene), human acute myeloid leukemia cell lines OCI-AML-3 (expressing FLT3 A680V mutant gene), human acute myeloid leukemia cell lines U937 (expressing wild-type FLT3 gene), and mouse pro-B cell BaF3 were selected, and the above cells were purchased from ATCC. Also mouse TEL-BaF3-FLT3/ITD (stably expressing FLT3/ITD mutant activated kinase), mouse TEL-BaF3-FLT3-D835Y (stably expressing FLT3 D835Y mutant activated kinase), mouse TEL-BaF3-BMX (stably expressing BMX kinase), mouse TEL-FLT3-BaF3 (stably expressing FLT3 kinase), mouse BaF3-FLT3-ITD-D835Y (stably expressing FLT3/ITD D835Y mutant activated kinase), mouse BaF3-FLT3-ITD-F691L (stably expressing FLT3/ITD F691L mutant activated kinase), mouse TEL-cKIT-BaF3 (stably expressing cKIT kinase), mouse BaF3-tel-cKit-N882K (stably expressing cKIT N882K mutant activated kinase), mouse BaF3-tel-cKit-D816V (stably expressing cKIT D816V mutant activated kinase), mouse BaF3-tel-cKit-T670I (stably expressing cKIT T670I mutant activated kinase), mouse TPR-MET-BaF3 (stably expressing MET kinase), mouse TEL-BaF3-EGFR (stably expressing EGFR kinase), mouse BaF3-FL-EGFR-L858R (stably expressing EGFR L858R mutant activated kinase), mouse TEL-BaF3-BLK (stably expressing BLK kinase), and mouse TEL-JAK1-BaF3 (stably expressing JAK1 kinase) were selected. The above cell lines were constructed by our laboratory. The method was as follows: the kinase region sequences of human FLT3/ITD, FLT3 D835Y, BMX, FLT3, FLT3/ITD D835Y, FLT3/ITD F691L, cKIT, cKIT N882K, cKIT D816V, cKIT T670I, MET, EGFR, EGFR L858R, BLK, and JAK1 kinase were amplified by PCR respectively, and were inserted into MSCV-Puro vectors with N-terminal TEL or TPR fragments (Clontech) respectively. The vectors were stably transfected into mouse BaF3 cells by the means of retrovirus, and the growth factor IL-3 ware removed, and eventually FLT3/ITD, FLT3 D835Y, BMX, FLT3, FLT3/ITD D835Y, FLT3/ITD F691L, cKIT, cKIT N882K, cKIT D816V, cKIT T670I, MET, EGFR, EGFR L858R, BLK, JAK1-transferred protein dependent cell lines were obtained were obtained.

In Examples, the above compounds in a different concentration (0.000508 μM, 0.00152 μM, 0.00457 μM, 0.0137 μM, 0.0411 μM, 0.123 μM, 0.370 μM, 1.11 μM, 3.33 μM, 10 μM in DMSO) were added to the above cells respectively, and the cells were incubated for 72 hours. The number of viable cells was determined by quantification of ATP in living cells using the Cell Titer-Glo® (Promega, USA) chemiluminescence cell viability assay kit. The experimental results were shown in Table 2.

TABLE 2

Effect on cell proliferation

| Compounds | MV4-11 IC50 [μM] | MOLM-13 IC50 [μM] | MOLM-14 IC50 [μM] | TEL-BaF3-FLT3/ITD IC50 [μM] | TEL-FLT3-BaF3 IC50 [μM] | TEL-BaF3-FLT3-D835Y IC50 [μM] | BaF3-FLT3-ITD-D835Y IC50 [μM] |
|---|---|---|---|---|---|---|---|
| Compound 92 | <0.0003 | | <0.0003 | <0.0003 | | <0.0003 | |
| Compound 86 | 0.02 | 0.001 | 0.005 | | 0.004 | | 0.006 |
| Compound 85 | 0.51 | | | 0.082 | | | |
| Compound 84 | 0.01 | | 0.002 | <0.0003 | 0.013 | 0.002 | 0.28 |
| Compound 40 | 0.76 | | | 0.16 | | | |
| Compound 38 | 0.97 | | | 0.12 | | | |
| Compound 39 | 0.23 | | | 0.093 | | | |
| Compound 37 | 0.23 | | | 0.15 | | | |
| Compound 36 | 0.67 | | | 0.15 | | | |
| Compound 35 | 0.28 | | | 0.07 | | | |
| Compound 34 | 0.35 | | | 0.07 | | | |
| Compound 33 | 0.16 | 0.16 | 0.22 | 0.077 | | 0.14 | 0.63 |
| Compound 32 | | | | | | | |
| Compound 31 | | | | | | | |
| Compound 30 | 0.17 | 0.13 | 0.26 | 0.048 | | 0.65 | 2.5 |
| Compound 29 | | | | | | | |
| Compound 13 | | | | 0.45 | | | |
| Compound 14 | 0.049 | 0.06 | 0.12 | 0.088 | | 0.24 | 0.25 |
| Compound 15 | | | | 0.2 | | | |
| Compound 16 | | | | 6 | | | |
| Compound 17 | | | | 0.88 | | | |
| Compound 18 | | | | 1.8 | | | |
| Compound 19 | | | | 0.79 | | | |
| Compound 20 | 0.2 | 0.16 | 0.41 | 0.12 | | 0.15 | |
| Compound 21 | | | | 0.33 | | | |
| Compound 22 | 0.022 | 0.021 | 0.042 | 0.011 | | 0.033 | 0.17 |
| Compound 23 | 0.32 | 0.29 | 0.63 | 0.091 | | 0.43 | |
| Compound 24 | | | | 0.67 | | | |
| Compound 25 | 0.12 | 0.12 | 0.19 | 0.088 | | 0.18 | |
| Compound 26 | 0.28 | 0.2 | 0.29 | 0.16 | | 0.36 | |
| Compound 27 | 0.032 | 0.014 | 0.023 | 0.005 | | 0.018 | 0.2 |
| Compound 5 | 0.12 | 0.085 | 0.21 | 0.51 | | 0.034 | 0.32 |
| Compound 6 | | | | 1.1 | | | |
| Compound 7 | 0.01 | 0.0012 | 0.023 | 0.009 | | 0.3 | 0.11 |
| Compound 8 | 0.27 | 0.18 | 0.31 | 0.27 | | 0.089 | |
| Compound 9 | | | | 1.1 | | | |
| Compound 10 | 0.061 | 0.064 | 0.11 | 0.11 | | 0.064 | |
| Compound 11 | 0.022 | 0.012 | 0.046 | 0.048 | | 0.02 | 0.28 |

TABLE 2-continued

| Effect on cell proliferation | | | | | | | |
|---|---|---|---|---|---|---|---|
| Compound 12 | 0.064 | 0.046 | 0.077 | 0.045 | | 0.048 | |
| Compound 2 | 0.3 | 0.29 | 0.72 | 0.12 | | 0.13 | |
| Compound 3 | | | | 1.8 | | | |
| Compound 4 | 0.3 | 0.23 | 0.68 | | | 0.16 | |
| Compound 57 | 0.06 | 0.76 | | 0.12 | | | |
| Compound 56 | 0.24 | 0.71 | | 0.49 | | | |
| Compound 58 | 0.058 | 0.19 | | 0.094 | | | |
| Compound 59 | 0.429 | 0.775 | | 0.18 | | | |
| Compound 61 | 0.948 | 2.12 | | 0.48 | | | |
| Compound 60 | 0.52 | 1.36 | | 0.3 | | | |
| Compound 63 | 0.35 | 0.72 | | 0.15 | | | |
| Compound 62 | 0.38 | 1.2 | | 0.41 | | | |
| Compound 66 | 0.73 | 1.6 | | 0.16 | | | |
| Compound 64 | 0.175 | 0.48 | | 0.08 | | | |
| Compound 65 | 0.083 | 0.23 | | 0.041 | | | |
| Compound 67 | 0.42 | 1.46 | | 0.13 | | | |
| Compound 28 | 0.12 | 1.9 | | 0.041 | | | |
| Compound 72 | | | | 0.075 | | | |
| Compound 73 | | | | 0.19 | | | |
| Compound 74 | | | | 0.075 | | | |
| Compound 76 | 0.027 | 0.016 | 0.036 | 0.0067 | 0.042 | 0.023 | 0.13 |
| Compound 77 | 0.0016 | 0.0027 | 0.0084 | <0.0003 | 0.0081 | 0.021 | 0.073 |
| Compound 78 | 0.018 | 0.019 | 0.11 | 0.0044 | 0.044 | 0.0076 | 0.053 |
| Compound 1 | 6.5 | | | 1.4 | | | |
| Compound 55 | >10 | | | 1.8 | | | |
| Compound 54 | 1.2 | | | 0.45 | | | |
| Compound 53 | 3.4 | | | 0.77 | | | |
| Compound 52 | 0.41 | | | 0.082 | | | |
| Compound 51 | 0.61 | | | 0.15 | | | |
| Compound 50 | 2.4 | | | 0.26 | | | |
| Compound 49 | 2.4 | | | 0.46 | | | |
| Compound 48 | 0.061 | 0.052 | 0.079 | 0.046 | | | |
| Compound 47 | 0.054 | 0.034 | 0.048 | 0.022 | | | |
| Compound 46 | 0.75 | | | 0.39 | | | |
| Compound 45 | 0.027 | 0.025 | 0.031 | 0.017 | | | 0.31 |
| Compound 44 | 0.064 | 0.072 | 0.059 | 0.022 | | | |
| Compound 43 | 0.022 | 0.02 | 0.028 | 0.007 | | | 0.41 |
| Compound 42 | 1.9 | | | 0.39 | | | |
| Compound 41 | 0.57 | | | 0.14 | | | |

| Compounds | BaF3-FLT3-ITD-F691L IC50 [μM] | BaF3 IC50 [μM] | U937 IC50 [μM] | OCI-AML3 IC50 [μM] | TEL-BaF3-BMX IC50 [μM] | TEL-cKIT-BaF3 IC50 [μM] | BaF3-tel-cKit-N882K IC50 [μM] |
|---|---|---|---|---|---|---|---|
| Compound 92 | | 1.9 | | | | | |
| Compound 86 | 0.15 | | 1.4 | | <0.0003 | 0.27 | |
| Compound 85 | | 0.95 | | | | | |
| Compound 84 | 0.43 | 0.75 | 3.3 | | 0.063 | 6.1 | |
| Compound 40 | | | 4.45 | 6.61 | | | |
| Compound 38 | | | 7.93 | 6.51 | | | |
| Compound 39 | | | 5.87 | 4.91 | | | |
| Compound 37 | | | >10 | 1.09 | | | |
| Compound 36 | | | 8.96 | >10 | | | |
| Compound 35 | | | 1.06 | 0.62 | | | |
| Compound 34 | | | >10 | 3.56 | | | |
| Compound 33 | 0.28 | 5 | >10 | 5.3 | 0.07 | 2.01 | |
| Compound 32 | | | | | | | |
| Compound 31 | | | | | | | |
| Compound 30 | 5.3 | >10 | >10 | >10 | 0.14 | 4.35 | |
| Compound 29 | | | | | | | |
| Compound 13 | | | >10 | | | | |
| Compound 14 | 0.37 | 9.8 | 4.14 | | 0.43 | 4.9 | |
| Compound 15 | | | >10 | | | | |
| Compound 16 | | | >10 | | | | |
| Compound 17 | | | >10 | | | | |
| Compound 18 | | | >10 | | | | |
| Compound 19 | | | >10 | | | | |
| Compound 20 | | >10 | >10 | | 0.047 | 3.3 | |
| Compound 21 | | | >10 | | | | |
| Compound 22 | 0.22 | 4.9 | 9.7 | | 0.28 | 1.9 | 1.2 |
| Compound 23 | | >10 | 4.3 | | 0.088 | 4.8 | |
| Compound 24 | | | 7.8 | | | | |
| Compound 25 | | 1.7 | 1.9 | | 0.51 | 3.1 | |
| Compound 26 | | 1.5 | 2.4 | | 1.3 | 3.5 | |
| Compound 27 | 0.28 | 1.3 | 4.1 | | 0.34 | 1.6 | |
| Compound 5 | 0.37 | >10 | 6.4 | | 0.2 | 2.2 | |
| Compound 6 | | | >10 | | | | |
| Compound 7 | 0.25 | 0.44 | 0.54 | | 0.33 | 0.35 | |

TABLE 2-continued

Effect on cell proliferation

| Compound | | | | | |
|---|---|---|---|---|---|
| Compound 8 | | 0.62 | 1 | 0.55 | 0.75 |
| Compound 9 | | >10 | | | |
| Compound 10 | | 1.2 | 3.4 | 0.84 | 1.1 |
| Compound 11 | 0.26 | 0.96 | 3.4 | 0.44 | 0.83 |
| Compound 12 | | 1.2 | 1.6 | 0.6 | 1 |
| Compound 2 | | 2 | >10 | 0.082 | 1.9 |
| Compound 3 | | >10 | | | |
| Compound 4 | | >10 | | 0.82 | 4.9 |
| Compound 57 | | 8.43 | | 2.3 | 3.4 |
| Compound 56 | | >10 | | | |
| Compound 58 | | 3.72 | | 0.27 | 7.4 |
| Compound 59 | | 9.29 | | | |
| Compound 61 | | 7.21 | | | |
| Compound 60 | | 4.37 | | | |
| Compound 63 | | 4.69 | | | |
| Compound 62 | | 8.46 | | | |
| Compound 66 | | 6.34 | | | |
| Compound 64 | | 7.59 | | 0.09 | 2.5 |
| Compound 65 | | 8.42 | | 1.2 | 3.5 |
| Compound 67 | | >10 | | | |
| Compound 28 | | 2.15 | | 0.39 | 5.3 |
| Compound 72 | | 3.65 | | | |
| Compound 73 | | >10 | | | |
| Compound 74 | | 0.59 | | | |
| Compound 76 | 0.18 | 4.2 | >10 | 0.12 | 0.43 |
| Compound 77 | 0.067 | 2.2 | 3.4 | 0.052 | 0.24 |
| Compound 78 | 0.27 | 6 | 3.6 | 0.038 | 0.32 |
| Compound 1 | | | >10 | >10 | |
| Compound 55 | | | >10 | >10 | |
| Compound 54 | | | >10 | >10 | |
| Compound 53 | | | >10 | >10 | |
| Compound 52 | | | >10 | 7.89 | |
| Compound 51 | | | >10 | >10 | |
| Compound 50 | | | >10 | >10 | |
| Compound 49 | | | >10 | >10 | |
| Compound 48 | | 6.5 | >10 | 4.36 | 0.122 |
| Compound 47 | | 3.8 | >10 | 2.7 | 0.056 |
| Compound 46 | | | 5.68 | 8.61 | |
| Compound 45 | 0.37 | 1.4 | >10 | 4.2 | 0.092 |
| Compound 44 | | 3.9 | >10 | 3.76 | 0.119 |
| Compound 43 | 1.1 | 3.8 | 7.21 | 5.98 | 0.022 |
| Compound 42 | | | >10 | >10 | |
| Compound 41 | | | 5.84 | 4.85 | |

| Compounds | BaF3-tel-cKit-D816V IC50 [μM] | BaF3-tel-cKit-T670I IC50 [μM] | TPR-MET-BaF3 IC50 [μM] | TEL-BaF3-EGFR IC50 [μM] | BaF3-FL-EGFR-L858R IC50 [μM] | TEL-BaF3-BLK IC50 [μM] | TEL-JAK1-BaF3 IC50 [μM] |
|---|---|---|---|---|---|---|---|
| Compound 92 | | | | | | | |
| Compound 86 | | | 3.3 | 1.3 | | 0.001 | |
| Compound 85 | | | | | | | |
| Compound 84 | | | 2.9 | | | 0.003 | |
| Compound 40 | | | | | | | |
| Compound 38 | | | | | | | |
| Compound 39 | | | | | | | |
| Compound 37 | | | | | | | |
| Compound 36 | | | | | | | |
| Compound 35 | | | | | | | |
| Compound 34 | | | | | | | |
| Compound 33 | | | 1.45 | | | 0.61 | |
| Compound 32 | | | | | | | |
| Compound 31 | | | | | | | |
| Compound 30 | | | 9.27 | | | 3.5 | |
| Compound 29 | | | | | | | |
| Compound 13 | | | | | | | |
| Compound 14 | | | 3 | 1.6 | | 1 | 7.7 |
| Compound 15 | | | | | | | |
| Compound 16 | | | | | | | |
| Compound 17 | | | | | | | |
| Compound 18 | | | | | | | |
| Compound 19 | | | | | | | |
| Compound 20 | | | >10 | 4.7 | | 0.52 | >10 |
| Compound 21 | | | | | | | |
| Compound 22 | 1 | 3.6 | 2.2 | 1.8 | | 0.94 | 3.8 |
| Compound 23 | | | >10 | 6.5 | | 2.8 | >10 |
| Compound 24 | | | | | | | |
| Compound 25 | | | 1.7 | 0.89 | | 1.1 | 3.3 |
| Compound 26 | | | 2 | 1.3 | | 2.9 | 2 |

TABLE 2-continued

Effect on cell proliferation

| | | | | |
|---|---|---|---|---|
| Compound 27 | 1.5 | 0.99 | 0.21 | 2.2 |
| Compound 5 | 5.7 | >10 | 0.97 | 4 |
| Compound 6 | | | | |
| Compound 7 | 0.53 | 1 | 0.051 | 0.37 |
| Compound 8 | 1.1 | 1.4 | 0.56 | 0.27 |
| Compound 9 | | | | |
| Compound 10 | 1.4 | 3.7 | 1 | 0.4 |
| Compound 11 | 1.4 | 2.2 | 0.09 | 0.34 |
| Compound 12 | 1.5 | 1.2 | 0.96 | 0.52 |
| Compound 2 | 4.7 | 6.1 | 0.63 | 1.4 |
| Compound 3 | | | | |
| Compound 4 | >10 | >10 | 1.4 | >10 |
| Compound 57 | | | 0.54 | 4.71 |
| Compound 56 | | | | |
| Compound 58 | | | 0.15 | |
| Compound 59 | | | | |
| Compound 61 | | | | |
| Compound 60 | | | | 0.77 |
| Compound 63 | | | | |
| Compound 62 | | | | |
| Compound 66 | | | | |
| Compound 64 | | | 0.0098 | 1.3 |
| Compound 65 | | | 0.36 | 0.89 |
| Compound 67 | | | | |
| Compound 28 | | | 0.083 | 0.91 |
| Compound 72 | | | | |
| Compound 73 | | | | |
| Compound 74 | | | | |
| Compound 76 | | | 0.03 | |
| Compound 77 | | | 0.0026 | |
| Compound 78 | | | 0.004 | |
| Compound 1 | | | | |
| Compound 55 | | | | |
| Compound 54 | | | | |
| Compound 53 | | | | |
| Compound 52 | | | | |
| Compound 51 | | | | |
| Compound 50 | | | | |
| Compound 49 | | | | |
| Compound 48 | 3.52 | | 1.1 | |
| Compound 47 | 2.46 | | 0.68 | |
| Compound 46 | | | | |
| Compound 45 | 1.38 | | 0.096 | |
| Compound 44 | 2.76 | | 1 | |
| Compound 43 | 2.77 | | 0.12 | |
| Compound 42 | | | | |
| Compound 41 | | | | |

Example 128

Effects of Compound 22, Compound 77 and Compound 84 on Upstream and Downstream Signaling Pathways of FLT3 in Cells In human acute myeloid leukemia MV4-11 (expressing FLT3/ITD mutant gene) cell lines, and human acute myeloid leukemia cell lines MOLM-14 (expressing FLT3/ITD mutant gene and wild-type FLT3 gene) cell lines, which carry FLT3 gene and/or FLT3/ITD mutant gene, the effects of Compound 22, Compound 77, Compound 84 and Control Compound FLT3 kinase inhibitor AC220 (AC220 was purchased from Hao Yuan Chemexpress Company, Shanghai) on phosphorylation of FLT3 and/or FLT3/ITD protein kinase and phosphorylation of STAT5 protein which is downstream in FLT3 closely related signaling pathways, as well as the effects on phosphorylation of other related protein kinases such as ERK, AKT in cells were tested by assaying a number of cellular biochemical and functional endpoints, at the same time we also examined the effect on phosphorylation of protein C-Myc and transcription factor NF-κB subunit p65 (FIG. 1). Using Compound 22, Compound 77, in a different concentration of 0 μM, 0.03 μM, 0.1 μM, 0.3 μM, 1 μM, 3 μM (in DMSO), Compound 84 in a different concentration of 0 μM, 0.003 μM, 0.01 μM, 0.03 μM, 0.1 μM, 0.3 μM, 1 μM (in DMSO), and 0.1 μM of FLT3 kinase inhibitor AC220 (in DMSO), acute myeloid leukemia MV 4-11, MOLM-14 cell lines, which carry FLT3 and/or FLT3/ITD gene, were treated for 4 hours, respectively, and the samples were collected. The effects of compounds on phosphorylation of proteins such as STAT5, C-Myc, ERK, NF-κB p65, AKT, and the like were examined in cells (FIG. 1).

The experimental results were shown in FIG. 1: in MV 4-11 and MOLM-14 cell lines, all of Compound 22, Compound 77 and Compound 84 strongly inhibited phosphorylation of protein kinase FLT3. In addition, in acute myeloid leukemia MV4-11 and MOLM-14 cell lines, which carry FLT3 and/or FLT3/ITD gene, all of Compound 22, Compound 77 and Compound 84 had very strong inhibitory effects on phosphorylation of STAT5 which is a FLT3/ITD downstream protein in cells, and had significant effects on the degradation of C-Myc which is a protein closely related to FLT3 protein kinase. In the same experiment, Control Compound FLT3 kinase inhibitor AC220 strongly inhibited protein kinase FLT3, and phosphorylation of STAT5 and C-Myc, which are proteins closely related to FLT3/ITD. By the comparison of the experimental results, it can be seen that, Compound 77, Compound 84 in the present invention had better efficacy than that of Control Compound FLT3 kinase inhibitor AC220.

It was shown in Example 128 that, all of Compound 22, Compound 77, Compound 84 strongly inhibited phosphorylation of protein kinase FLT3, affected phosphorylation of STAT5 which is a downstream protein in the signaling pathways of protein kinase FLT3 in cells, thereby inhibiting cell proliferation of acute myeloid leukemia cell lines carrying FLT3 and/or FLT3/ITD gene.

Example 129

Detection of In Vitro Inhibition Activity (Enzymatic Activity)

In the experiments of in vitro enzymatic activity, the IC50 values of Compound 33, Compound 30, Compound 14, Compound 20, Compound 22, Compound 23, Compound 25, Compound 26, Compound 27, Compound 5, Compound 6, Compound 7, Compound 8, Compound 9, Compound 10, Compound 11, Compound 12, Compound 2, Compound 3, Compound 4, Compound 76, Compound 77, Compound 78, Compound 48, Compound 47, Compound 45, Compound 44, Compound 43 and AC220 on protein kinase FLT3, FLT3/ITD and BTK were determined. The intracellular segment regions of protein kinase FLT3, FLT3/ITD and BTK were cloned into the insect expression vector pAcG2T, and the proteins were expressed by using an insect expression system, BaculoGold™ Baculovirus Expression System (BD Pharmingen), with GST tag. The established vectors were transfected into SF9 packaging viruses, so as to infect the SF9-expressed proteins with the viruses.

9 µL (6 ng/µL) of purified FLT3 and BTK protein kinase were reacted with 1 µL of three-fold gradient dilution of the above compounds (final concentrations of the agents were 10 µM, 3 µM, 1 µM, 0.3 µM, 0.1 µM, 0.03 µM, 0.01 µM, 0.003 µM), respectively, at room temperature for 4 hours;

2 µL of ATP and 3 µL of substrate, Poly(4:1 Glu, Tyr) Peptide (Promega, US), were added (final concentrations are 10 µM and 0.2 µg/µL, respectively), and reacted at 37° C. for 1 hour;

5 µL of reacted kinase solution was added into 5 µL of ADP-Glo™ (Promega, US) and reacted at room temperature for 40 min, the kinase reaction was stopped and the remained ATP was consumed;

10 µL of kinase detection reagent was added to transfer ADP into ATP, and the newly obtained ATP was detected by using coupled luciferase/fluorescein reaction, then the IC50 values were calculated by using a plotting method based on the Envision reading (Table 3).

Figure 2A:
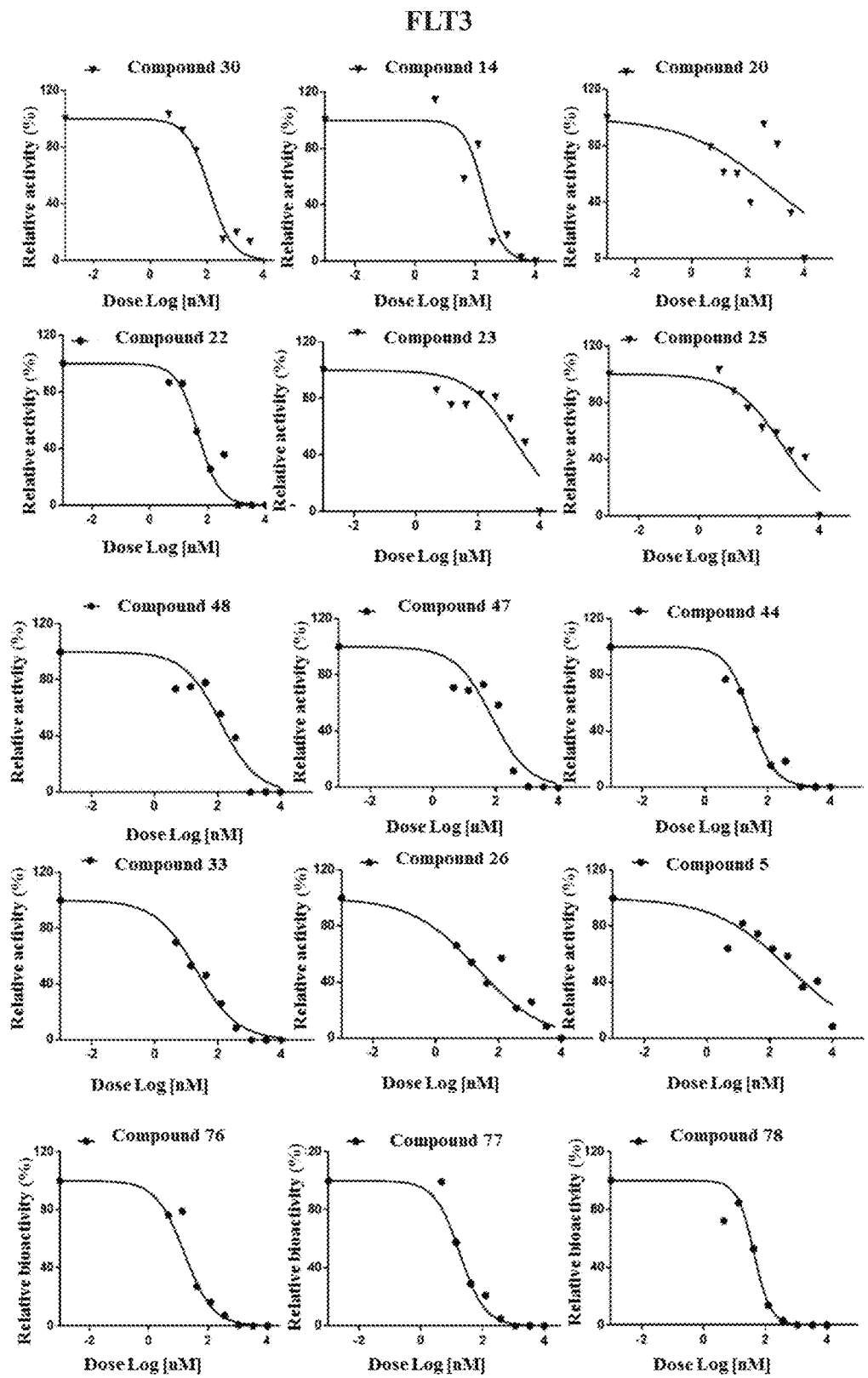
FIGS. 2a to 2c illustrate the detection results of in vitro inhibition activity (enzymatic activity) of the compounds in the present invention against FLT3, FLT3/ITD and BTK protein kinases, respectively.
Figure 2B:
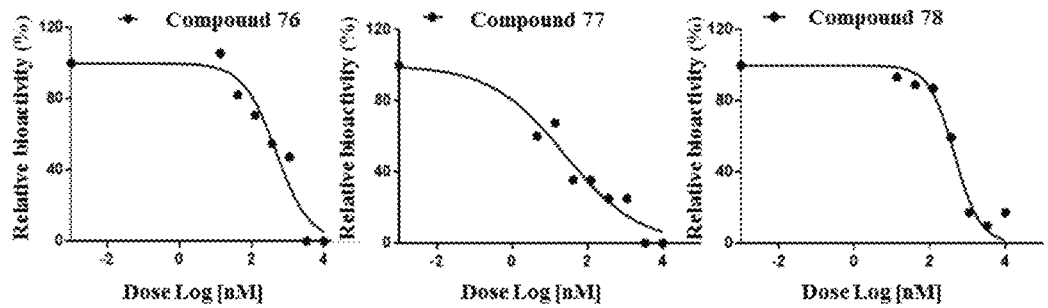
Figure 2C:
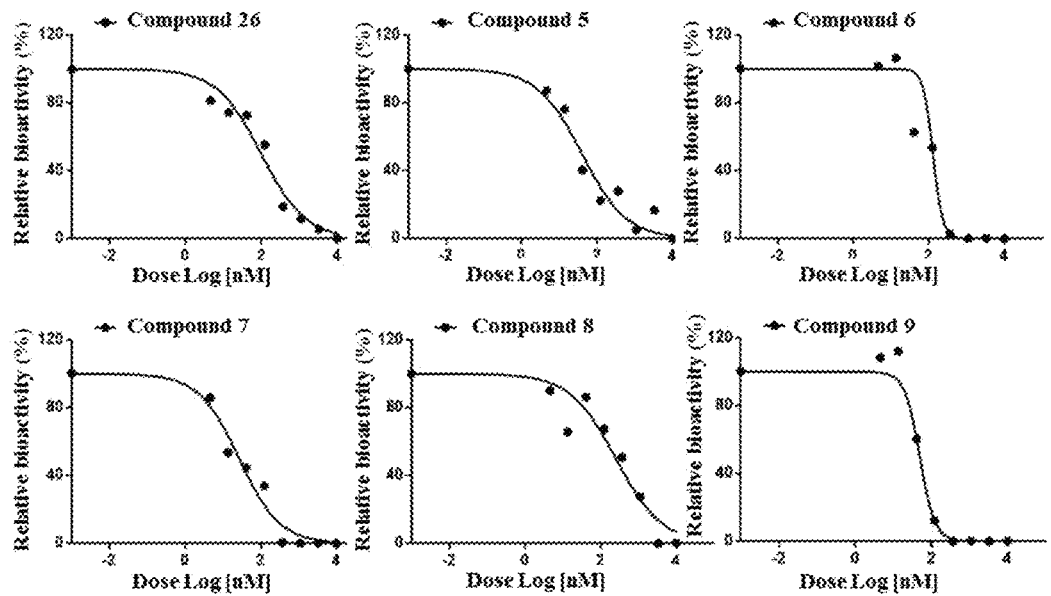

The experimental results were shown in FIG. 2: the exemplary compounds of the present invention have a strong inhibitory effect on FLT3, FLT3/ITD and BTK protein kinase, and these results demonstrate that the Compound of the present invention is an inhibitor of FLT3 kinase and also inhibits FLT3/ITD and BTK kinase.

TABLE 3

Test results of in vitro inhibition activity (enzymatic activity)

| Compounds | FLT3 protein kinase IC50[µM] | FLT3-ITD protein kinase IC50[µM] | BTK protein kinase IC50[µM] |
| --- | --- | --- | --- |
| Compound 33 | 0.02 | | 0.421 |
| Compound 30 | 0.122 | | 1.83 |
| Compound 14 | 0.186 | | 0.063 |
| Compound 20 | 0.718 | | 0.114 |
| Compound 22 | 0.047 | 0.33 | 0.19 |
| Compound 23 | 1.577 | | 0.204 |
| Compound 25 | 0.58 | | 0.216 |
| Compound 26 | 0.12 | | 0.098 |
| Compound 27 | 0.144 | | 0.688 |
| Compound 5 | 0.404 | | 0.04 |
| Compound 6 | 0.343 | | 0.128 |
| Compound 7 | 0.399 | | 0.027 |
| Compound 8 | 1.906 | | 0.254 |
| Compound 9 | 1.062 | | 0.049 |
| Compound 10 | 0.168 | | 0.128 |
| Compound 11 | 0.1 | | |
| Compound 12 | 0.012 | | 0.349 |
| Compound 2 | 0.572 | | |
| Compound 3 | 5.556 | | |
| Compound 4 | 2.078 | | |
| Compound 76 | 0.016 | 0.478 | 0.388 |
| Compound 77 | 0.018 | 0.024 | 0.128 |
| Compound 78 | 0.042 | 0.455 | 0.343 |
| Compound 48 | 0.121 | | 0.028 |
| Compound 47 | 0.076 | | 0.027 |
| Compound 45 | 0.032 | | 0.26 |
| Compound 44 | | | 0.053 |
| Compound 43 | 0.037 | | 0.028 |
| AC220 | 0.0159 | | |

Example 130

Effects of Compound 22 and Compound 84 on Cell Apoptosis in Cells

In acute myeloid leukemia MOLM-13, MV4-11 cell lines, which carry FLT3 gene and/or FLT3/ITD mutant gene, the effects of Compound 22 and Compound 84 on protein cleavage of DNA repair enzyme, poly ADP-ribose polymerase PARP, cysteinyl aspartate specific proteinase Caspase 3, which was closely related to cell apoptosis, were examined in cells in order to confirm whether the death of the cells after the administration was by apoptosis or necrosis. Using Compound 22 in a different concentration of 0 µM, 0.03 µM, 0.1 µM, 0.3 µM, 1 µM (in DMSO), Compound 84 in a different concentration of 0 µM, 0.03 µM, 0.1 µM, 0.3 µM, 1 µM (in DMSO), and 0.1 µM of FLT3 kinase inhibitor AC220 (in DMSO), MOLM-13, MV 4-11 cell lines were treated respectively, and then the cells were harvested at 12 hours, 24 hours, 48 hours later. Western Blot was used to detect the effects of different concentrations of drugs on protein cleavage of DNA repair enzyme, poly ADP-ribose polymerase PARP and cysteinyl aspartate specific proteinase Caspase 3 at different time intervals (FIG. 3).

Figure 3A:
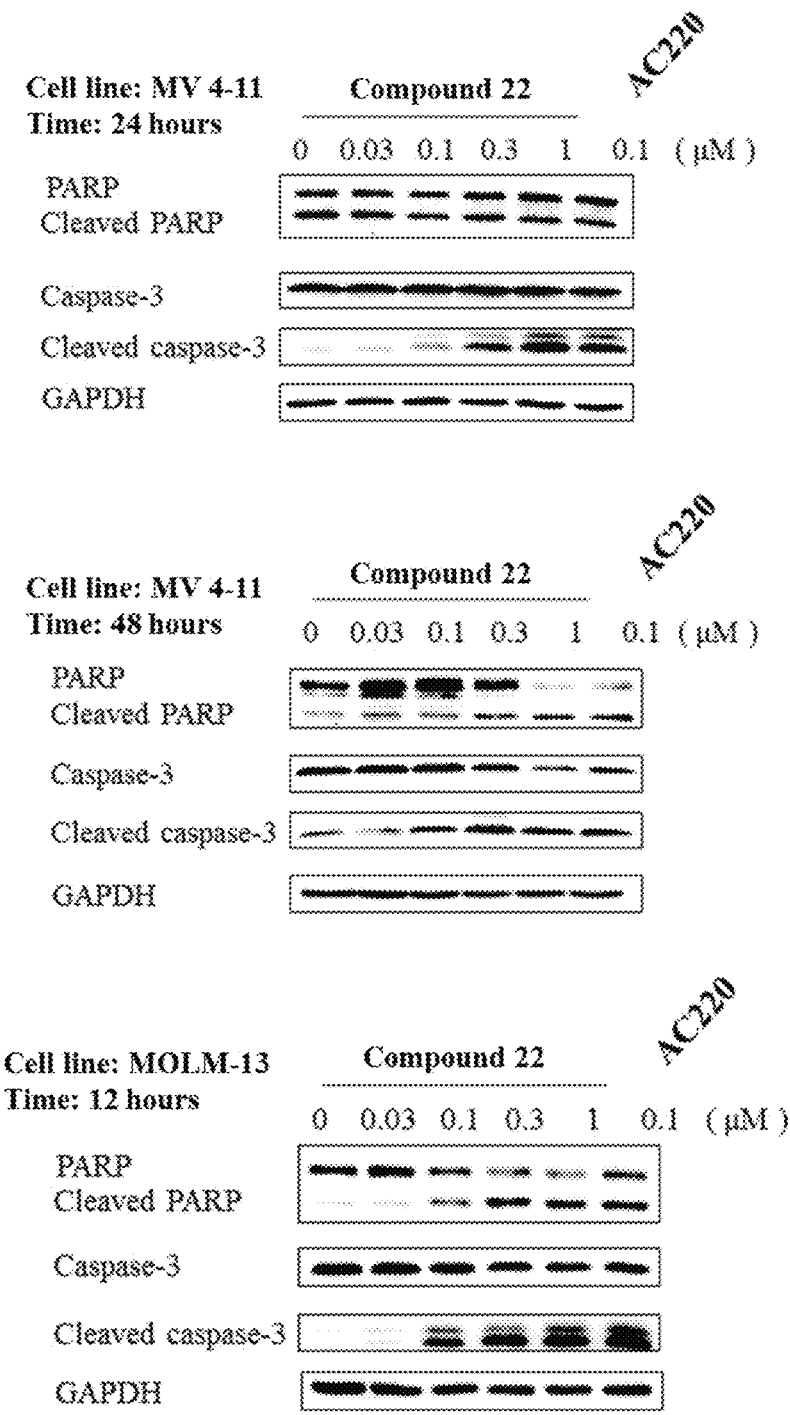
FIGS. 3a to 3b illustrate the effects of Compound 22 and Compound 84 on the apoptosis of MV4-11, MOLM-13 cell lines, respectively.
Figure 3B:
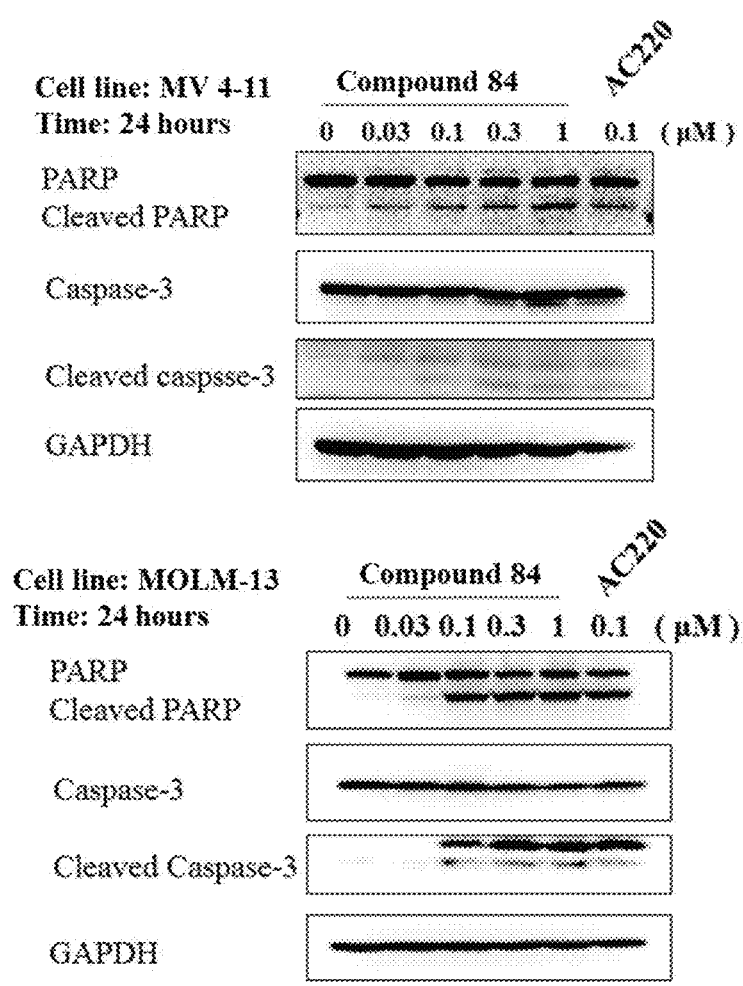

The experimental results were shown in FIG. 3: for acute myeloid leukemia cell lines MOLM-13 carrying FLT3 gene and/or FLT3/ITD mutant gene, when the administration concentration of Compound 22 was 0.1 µM, it was possible to see a very significant cleavage of DNA repair enzyme, poly ADP-ribose polymerase PARP, as well as a very significant cleavage of cysteinyl aspartate specific proteinase Caspase 3 after 12 hours; when the administration concentration of Compound 84 was 0.1 µM, it was possible to see a very significant cleavage of DNA repair enzyme, poly ADP-ribose polymerase PARP, as well as a very significant cleavage of cysteinyl aspartate specific proteinase Caspase 3 after 24 hours, similarly, when 0.1 µM of Control Compound FLT3 kinase inhibitor AC220 was used, it was possible to observe the same phenomenon. For acute myeloid leukemia MV 4-11 carrying FLT3 gene and/or FLT3/ITD mutant gene, when the administration concentration of Compound 22 was 0.1 µM, it was possible to see a significant cleavage of DNA repair enzyme, poly ADP-ribose polymerase PARP, and also possible to see a very significant cleavage of cysteinyl aspartate specific proteinase Caspase 3 after 24 and hours, respectively; When the administration concentration of Compound 84 was 0.03 µM, it could be observed a relatively significant cleavage of DNA repair enzyme, poly ADP-ribose polymerase PARP, and could be observed a cleavage of cysteinyl aspartate specific proteinase Caspase 3 after 24 hours. Example 130 demonstrated that Compound 22 and Compound 84 were capable of eliciting apoptosis in acute myeloid leukemia cells carrying FLT3 gene and/or FLT3/ITD mutant gene.

Example 131

Effects of Compound 22 and Compound 84 on Cell Cycles in Cells

In acute myeloid leukemia MV4-11 cell lines carrying FLT3/ITD mutant gene, the effects of Compound 22 and Compound 84 on cell cycle distribution of these cell lines were examined in order to study the growth cycle during which the cells were blocked by administration. Using Compound 22 in a different concentration of 0 µM, 0.03 µM, 0.1 µM, 0.3 µM (in DMSO), 0.1 µM or 0.01 µM of FLT3 kinase inhibitor AC220 (in DMSO), acute myeloid leukemia MV4-11 cell lines carrying FLT3/ITD mutant gene were treated for 24 hours. The cells were harvested, washed with 1×PBS buffer twice, fixed with 75% ethanol at −20° C. for 24 hours, washed again with 1×PBS buffer twice, 0.5 mL of 1×PBS buffer and 0.5 mL of PI dyeing liquor (purchase from BD Bioscience, USA) were added to the cells, and the cells were placed in the dark at 37° C. for 15 minutes and the cell cycle distribution was detected by flow cytometry (BD FACS Calibur) (FIG. 4).

Figure 4:
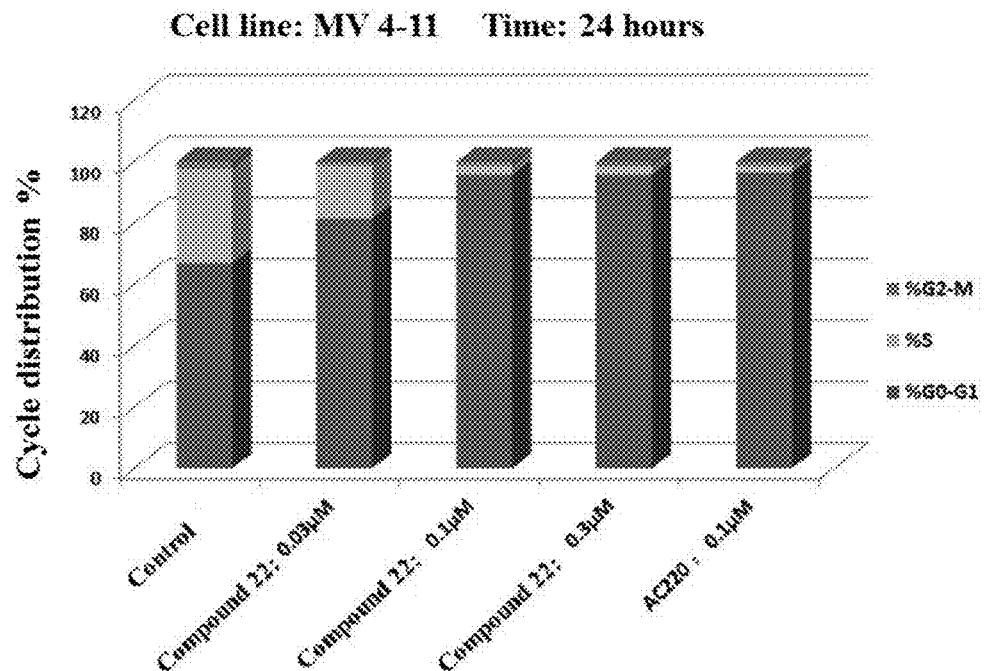
FIGS. 4a to 4b illustrate the effects of Compound 22 and Compound 84 on the cell cycle distribution of MV4-11 cell lines.
Figure 4:
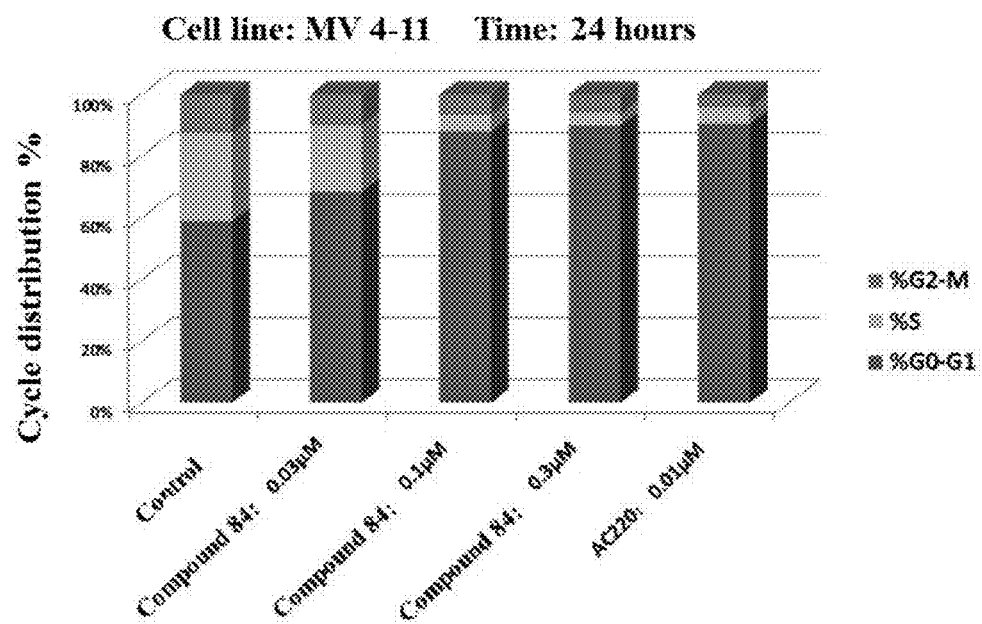

The experimental results were shown in FIG. 4: in acute myeloid leukemia MV4-11 cell lines carrying FLT3/ITD mutant gene, the number of cells captured in G0-G1 phase increased from 66.99%, 58.98% to 95.78% and 89.92%, respectively, with the concentration of Compound 22, Compound 84 increasing from 0 µM to 0.1 µM. The number of cells captured in G0-G1 phase by FLT3 kinase inhibitor AC220 with higher selective at 0.1 µM or 0.01 µM were 96.53% and 90.49%, respectively;

Example 131 demonstrated that Compound 22 and Compound 84 were capable of blocking acute myeloid leukemia MV4-11 cells carrying FLT3/ITD mutant gene in G0-G1 phase, and had a strong effect on the cell cycle distribution (FIG. 4).

Example 132

Use of Compound 22 and Compound 77 to Treat Acute Myeloid Leukemia

In order to detect the inhibitory effect of Compound 22 and Compound 77 on the tumor in vivo, a model of nude mouse subcutaneous tumor was introduced. More than 30 mice (5-week-old) (Balb/c-nu female mice, purchased from Shanghai Snake Experimental Animal Co., Ltd.) were inoculated subcutaneously with MOLM-14 cells in $1\times10^7$ cells/mouse, the changes in body weight and tumor volume were recorded daily (tumor volume=Tumor length×tumor width$^2$/2). 10 days later, the mice, of which tumor volumes reached 200-400 mm$^3$, were randomly divided into three groups with 6-10 mice of each group, and were treated as follows: The first group was administered daily by oral gavage with vehicle, i.e., methylcellulose-based aqueous suspension (purchased from Sinopharm Group Chemical Reagent Co., Ltd.); the second group was administered by oral gavage with 12.5 mg/kg of Compound 22 and/or Compound 77 in a methylcellulose-based aqueous suspension formulation; the third group was administered by oral gavage with 25 mg/kg of Compound 22 and/or Compound 77 in a methylcellulose-based aqueous suspension formulation; the fourth group was administered daily by oral gavage with 50 mg/kg of Compound 22 and/or Compound 77 in a methylcellulose-based aqueous suspension formulation; The first day of administration was recorded as day 0, followed by continuous administration for 2 to 3 weeks (FIG. 5).

Figure 5:
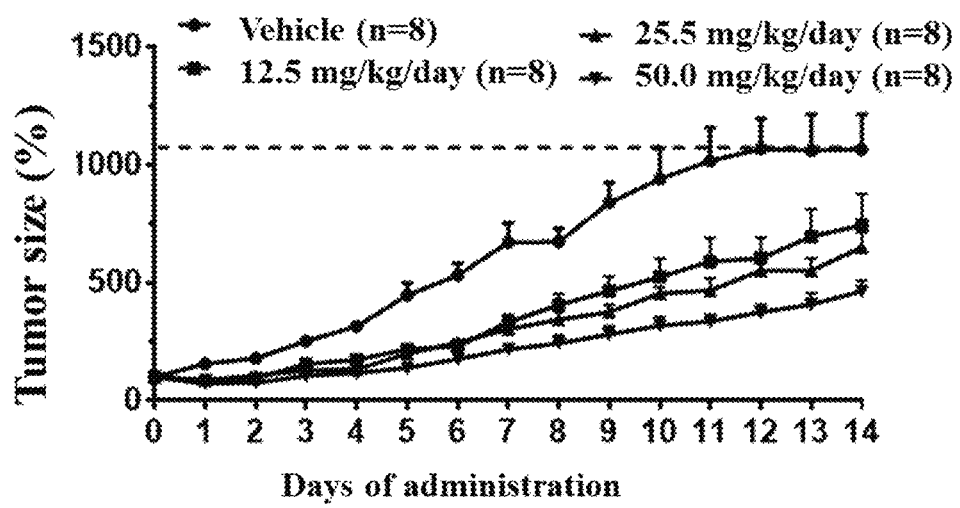
FIGS. 5a to 5b illustrate the tumor inhibiting effect of Compound 22 and Compound 77 in the tumor transplanted mouse model with MOLM-14 cell.
Figure 5:
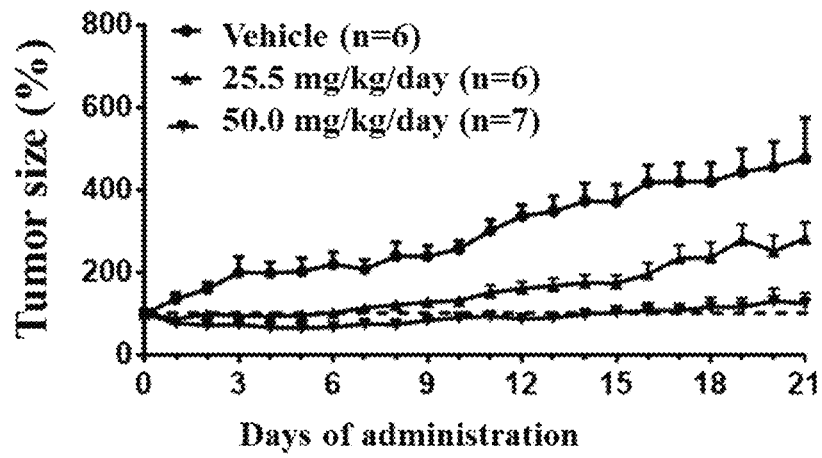

The experimental results were shown in FIG. 5. After treatment with Compound 22, the tumor growth of the mice was significantly inhibited and the tumor volume growth of the mice was significantly slowed down (FIG. 5a); After treatment with Compound 77, the tumor growth of the mice was significantly inhibited (FIG. 5b), the tumor volume growth of the mice in the group treated in 25 mg/kg/day was significantly slowed down, and the tumors of the mice in the group treated in 50.0 mg/kg/day had almost no growth. The data from the tumor-transplanted mouse model in this example demonstrated that Compound 22 and Compound 77 could play a very strong role in inhibiting tumor growth in acute myeloid leukemia (AML) in mice.

INDUSTRIAL APPLICABILITY

The present invention provides compounds as novel inhibitors of FLT3 kinase, which may be used for reducing or inhibiting the activity of FLT3 kinase and/or mutant FLT3 kinase in a cell or a subject, and/or for preventing or treating cell proliferative conditions and/or FLT3-related conditions in a subject. Therefore, it can be prepared as corresponding medicament and has industrial applicability.

While the invention has been described in detail herein, the invention is not limited thereto and modifications may be made by those skilled in the art based on the principles of the invention, and thus, all modifications in accordance with the principles of the invention are to be understood as within the protection scope of the invention.

The invention claimed is:

1. A compound of formula (II), or a pharmaceutically acceptable salt, solvate, isomer, ester, acid, metabolite or prodrug thereof, having the following structure:

Formula (II)

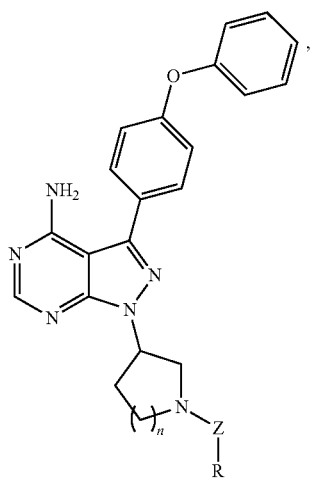

n is 2;
Z is

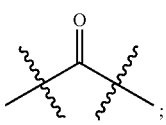 [SMILES: *C(*)=O]

;

R is selected from the group consisting of unsubstituted C3-C6 cycloalkyl or C3-C6 cycloalkyl optionally substituted with 1 to 3 independent R1 on carbon atoms; amino; carbamoyl; unsubstituted C1-C6 aminoalkyl or C1-C6 aminoalkyl optionally substituted with 1 to 3 independent R1 on carbon atoms or optionally substituted with R2 on heteroatoms; unsubstituted heteroaryl or heteroaryl optionally substituted with 1 to 3 independent R1 on carbon atoms or optionally substituted with R2 on heteroatoms; unsubstituted C3-C6 heterocycloalkyl or heterocycloalkyl optionally substituted with 1to 3 independent R1 on carbon atoms or optionally substituted with R2 on heteroatoms; unsubstituted aryl or aryl optionally substituted with 1 to 3 independent R1 on carbon atoms; unsubstituted di(C1-C4 alkyl)-N-(C1-C4)alkyl or di(C1-C4 alkyl)-N-(C1-C4) alkyl optionally substituted with 1 to 3 independent R1 on carbon atoms; unsubstituted C1-C4 alkyl(C3-C6 heterocycloalkyl) or C1-C4 alkyl(C3-C6 heterocycloalkyl) optionally substituted with 1 to 3 independent R1 on carbon atoms or optionally substituted with R2 on heteroatoms; unsubstituted C1-C4 alkyl(C3-C6 cycloalkyl) or C1-C4 alkyl(C3-C6 cycloalkyl) optionally substituted with 1 to 3 independent R1 on carbon atoms; unsubstituted C1-C4 aminoalkyl(carbamoyl) or C1-C4 aminoalkyl(carbamoyl) optionally substituted with 1 to 3 independent R1 on carbon atoms; unsubstituted C1-C4 alkyl(heteroaryl) or C1-C4 alkyl(heteroaryl) optionally substituted with 1 to 3 independent R1 on carbon atoms or optionally substituted with R2 on heteroatoms; and unsubstituted C1-C4 alkyl(aryl) or C1-C4 alkyl(aryl) optionally substituted with 1 to 3 independent R1 on carbon atoms;

R1 is independently selected from the group consisting of halogen, amino, nitro, cyano, hydroxy, C1-C8 alkyl, C3-C8 cycloalkyl, C1-C8 alkoxy, aryl, heteroaryl optionally substituted with R2 on heteroatoms, C1-C8 alkoxycarbonyl, C1-C8 alkyl(heteroaryl) optionally substituted with R2 on heteroatoms, and C1-C8 alkyl (C3-C6 heterocycloalkyl) optionally substituted with R2 on heteroatoms;

R2 is selected from the group consisting of amino protecting groups, C1-C8 alkyl, and C1-C8 alkoxycarbonyl; the amino protecting group is independently selected from the group consisting of tert-butoxycarbonyl, benzyloxycarbonyl, 9-fluorenylmethoxycarbonyl, benzyl and p-methoxyphenyl.

2. The compound of formula (II), or a pharmaceutically acceptable salt, solvate, isomer, ester, acid, metabolite or prodrug thereof, according to claim 1, wherein heteroaryl is independently selected from the group consisting of pyridyl, pyrimidinyl, isoxazolyl, benzodioxolyl, imidazolyl and indolyl.

3. The compound of formula (II), or a pharmaceutically acceptable salt, solvate, isomer, ester, acid, metabolite or prodrug thereof, according to claim 1, wherein heterocycloalkyl is independently selected from the group consisting of piperazinyl, piperidyl, and morpholinyl.

4. The compound of formula (II), or a pharmaceutically acceptable salt, solvate, isomer, ester, acid, metabolite or prodrug thereof, according to claim 1, which is selected from the group consisting of:

| Compound 1 | 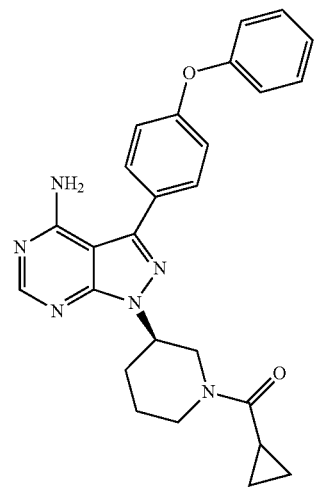 [SMILES: Nc1ncnc2c1c(-c1ccc(Oc3ccccc3)cc1)nn2[C@@H]1CCCN(C(=O)C2CC2)C1] |
| Compound 5 | 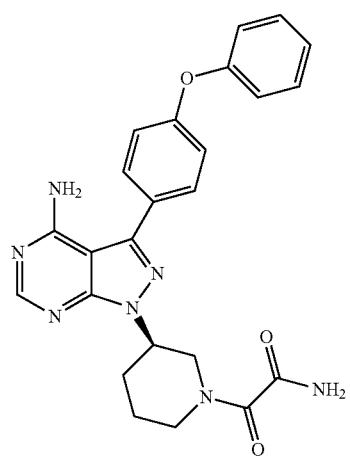 [SMILES: NC(=O)C(=O)N1CCC[C@@H](n2nc(-c3ccc(Oc4ccccc4)cc3)c3c(N)ncnc32)C1] |

| Compound 6 | Compound 9 |
|---|---|
| 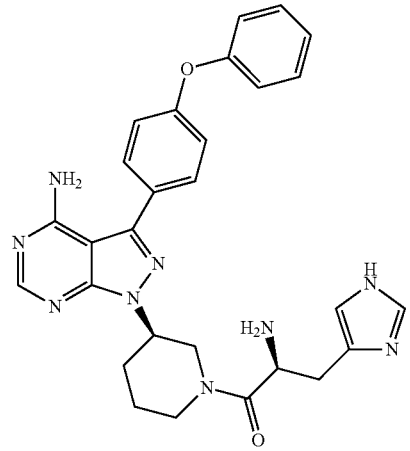 [SMILES: Nc1ncnc2c1c(-c1ccc(Oc3ccccc3)cc1)nn2[C@@H]1CCCN(C(=O)[C@@H](N)Cc2c[nH]cn2)C1] | 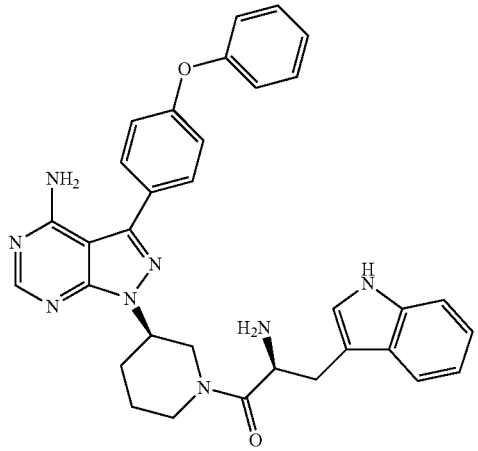 |
| Compound 7 | Compound 10 |
| 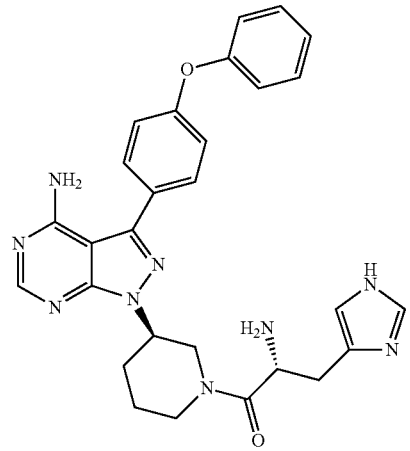 [SMILES: Nc1ncnc2c1c(-c1ccc(Oc3ccccc3)cc1)nn2[C@@H]1CCCN(C(=O)[C@H](N)Cc2c[nH]cn2)C1] | 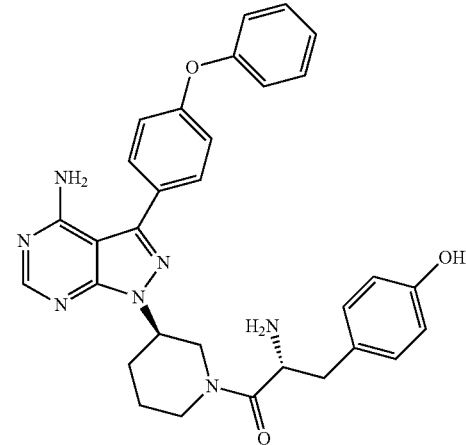 |
| Compound 8 | Compound 11 |
| 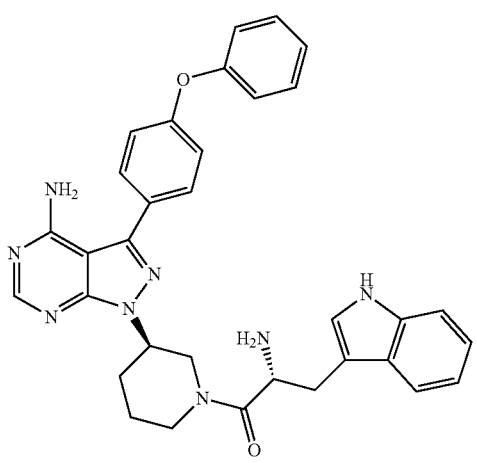 [SMILES: Nc1ncnc2c1c(-c1ccc(Oc3ccccc3)cc1)nn2[C@@H]1CCCN(C(=O)[C@H](N)Cc2c[nH]c3ccccc23)C1] | 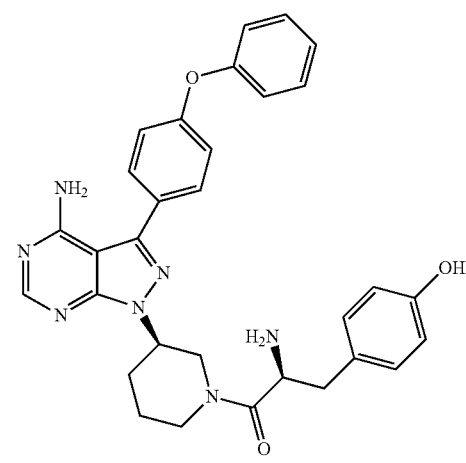 [SMILES: Nc1ncnc2c1c(-c1ccc(Oc3ccccc3)cc1)nn2[C@@H]1CCCN(C(=O)[C@@H](N)Cc2ccc(O)cc2)C1] |

Compound 12
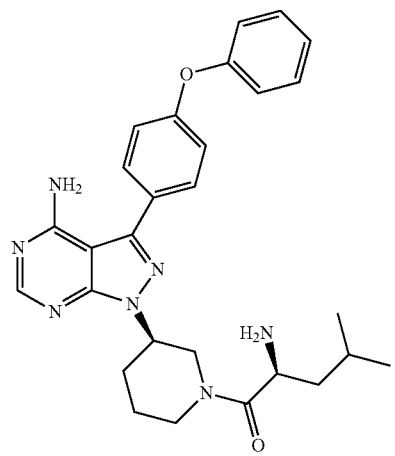 [SMILES: CC(C)C[C@H](N)C(=O)N1CCC[C@@H](n2nc(-c3ccc(Oc4ccccc4)cc3)c3c(N)ncnc32)C1]
Compound 13
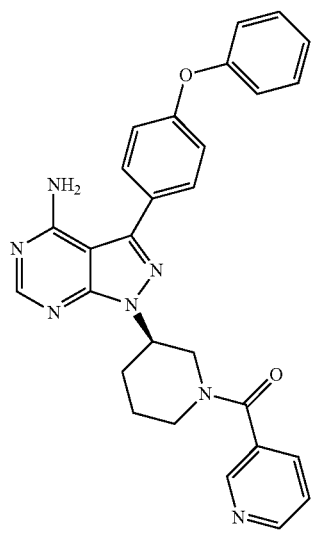 [SMILES: Nc1ncnc2c1c(-c1ccc(Oc3ccccc3)cc1)nn2[C@@H]1CCCN(C(=O)c2cccnc2)C1]
Compound 14
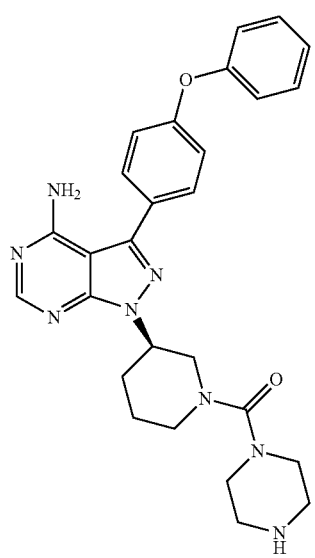 [SMILES: Nc1ncnc2c1c(-c1ccc(Oc3ccccc3)cc1)nn2[C@@H]1CCCN(C(=O)N2CCNCC2)C1]
Compound 15
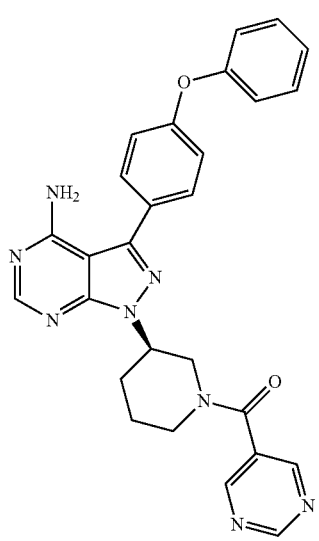 [SMILES: Nc1ncnc2c1c(-c1ccc(Oc3ccccc3)cc1)nn2[C@@H]1CCCN(C(=O)c2cncnc2)C1]
Compound 16
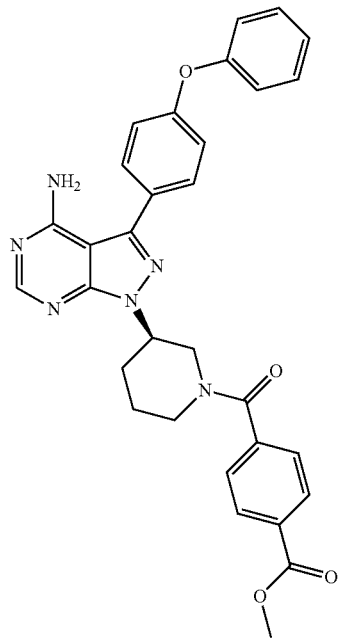 [SMILES: COC(=O)c1ccc(C(=O)N2CCC[C@@H](n3nc(-c4ccc(Oc5ccccc5)cc4)c4c(N)ncnc43)C2)cc1]

Compound 17
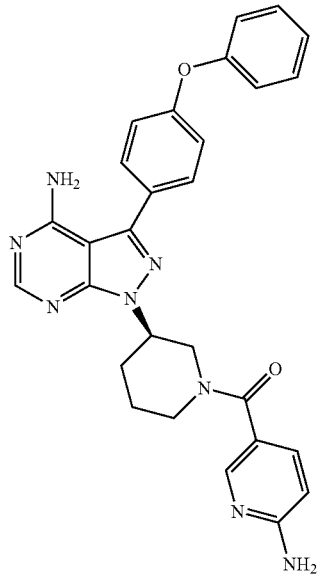 [SMILES: Nc1ccc(C(=O)N2CCC[C@@H](n3nc(-c4ccc(Oc5ccccc5)cc4)c4c(N)ncnc43)C2)cn1]
Compound 18
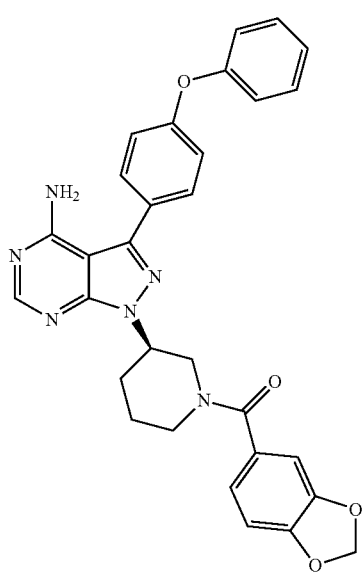 [SMILES: Nc1ncnc2c1c(-c1ccc(Oc3ccccc3)cc1)nn2[C@@H]1CCCN(C(=O)c2ccc3c(c2)OCO3)C1]
Compound 19
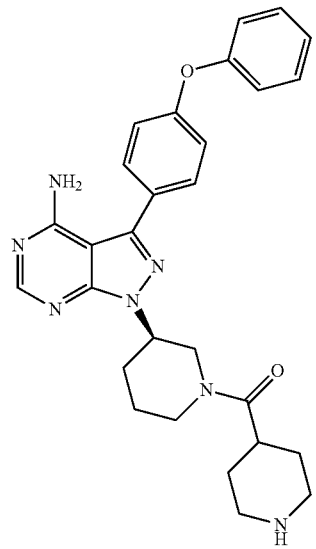
Compound 21
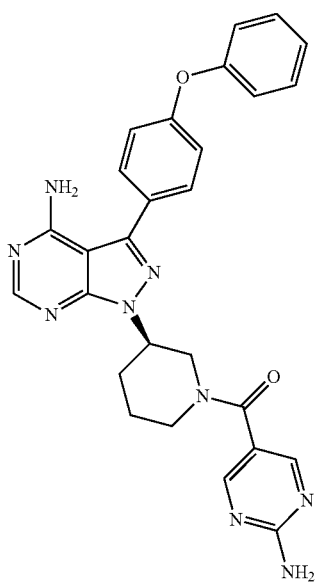 [SMILES: Nc1ncc(C(=O)N2CCC[C@@H](n3nc(-c4ccc(Oc5ccccc5)cc4)c4c(N)ncnc43)C2)cn1]
Compound 22
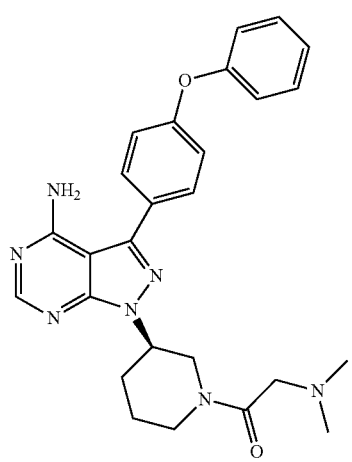 [SMILES: CN(C)CC(=O)N1CCC[C@@H](n2nc(-c3ccc(Oc4ccccc4)cc3)c3c(N)ncnc32)C1]

Compound 24
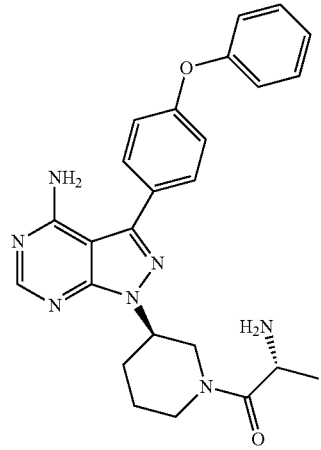 [SMILES: C[C@@H](N)C(=O)N1CCC[C@@H](n2nc(-c3ccc(Oc4ccccc4)cc3)c3c(N)ncnc32)C1]
Compound 27
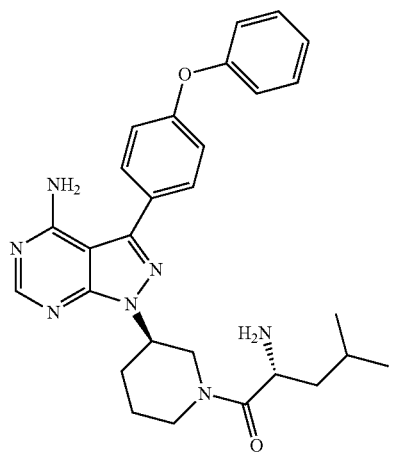
Compound 25
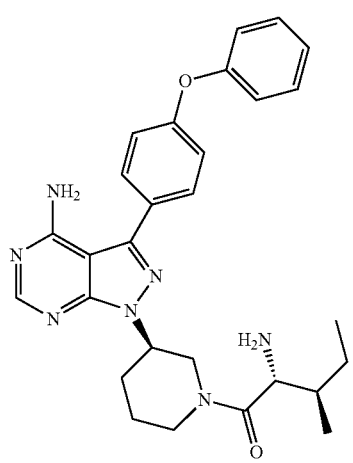 [SMILES: CC[C@@H](C)[C@@H](N)C(=O)N1CCC[C@@H](n2nc(-c3ccc(Oc4ccccc4)cc3)c3c(N)ncnc32)C1]
Compound 29
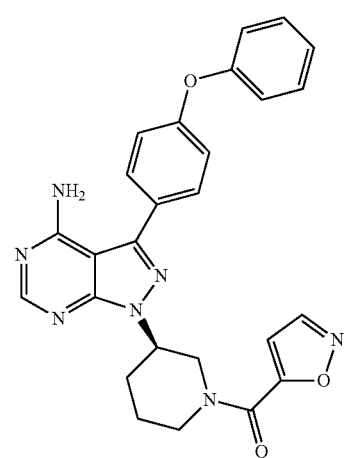
Compound 26
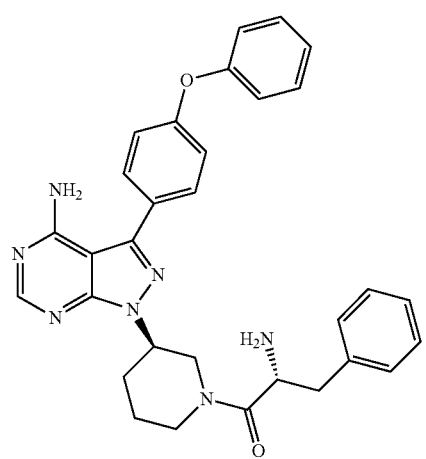 [SMILES: Nc1ncnc2c1c(-c1ccc(Oc3ccccc3)cc1)nn2[C@@H]1CCCN(C(=O)[C@H](N)Cc2ccccc2)C1]
Compound 31
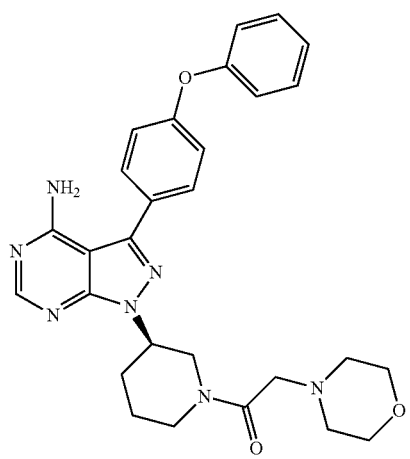 [SMILES: Nc1ncnc2c1c(-c1ccc(Oc3ccccc3)cc1)nn2[C@@H]1CCCN(C(=O)CN2CCOCC2)C1]

-continued
Compound 32
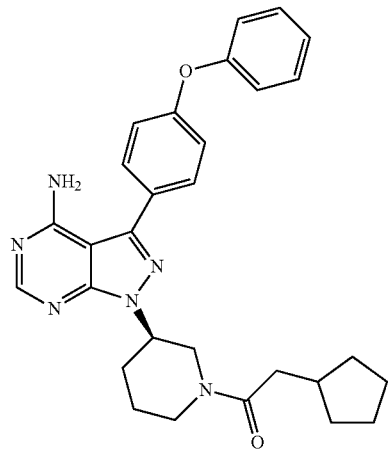 [SMILES: Nc1ncnc2c1c(-c1ccc(Oc3ccccc3)cc1)nn2[C@@H]1CCCN(C(=O)CC2CCCC2)C1]
Compound 33
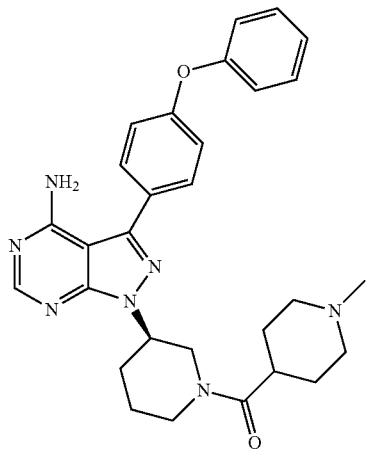 [SMILES: CN1CCC(C(=O)N2CCC[C@@H](n3nc(-c4ccc(Oc5ccccc5)cc4)c4c(N)ncnc43)C2)CC1]
Compound 35
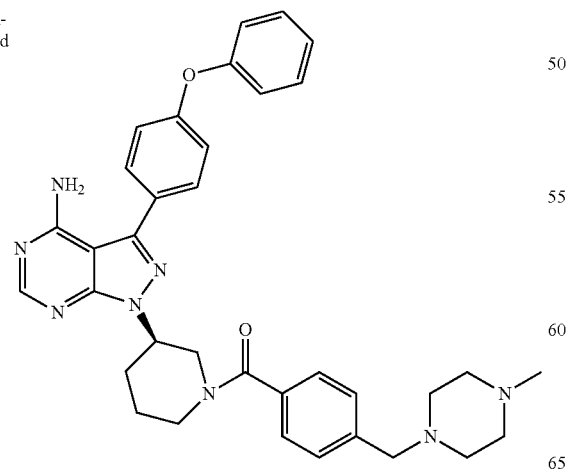
-continued
Compound 39
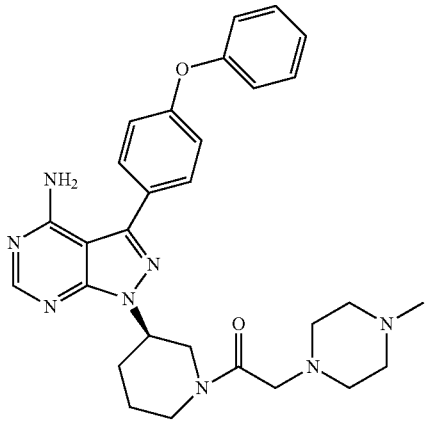 [SMILES: CN1CCN(CC(=O)N2CCC[C@@H](n3nc(-c4ccc(Oc5ccccc5)cc4)c4c(N)ncnc43)C2)CC1]
Compound 43
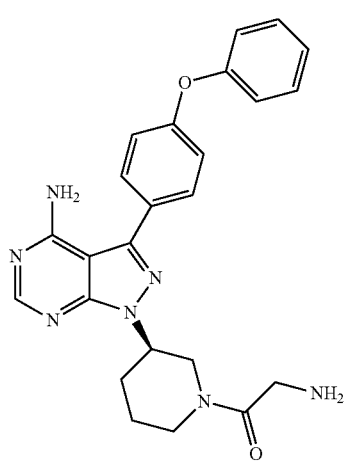 [SMILES: NCC(=O)N1CCC[C@@H](n2nc(-c3ccc(Oc4ccccc4)cc3)c3c(N)ncnc32)C1]
Compound 44
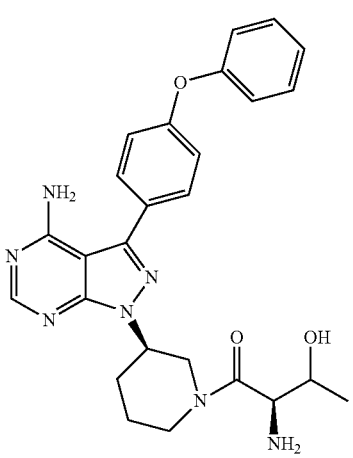 [SMILES: CC(O)[C@@H](N)C(=O)N1CCC[C@@H](n2nc(-c3ccc(Oc4ccccc4)cc3)c3c(N)ncnc32)C1]

| | |
|---|---|
| Compound 45 | 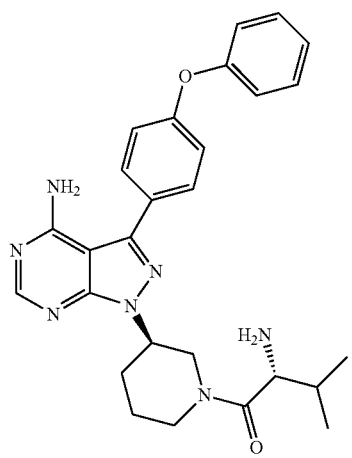 [SMILES: CC(C)[C@@H](N)C(=O)N1CCC[C@@H](n2nc(-c3ccc(Oc4ccccc4)cc3)c3c(N)ncnc32)C1] |
| Compound 46 | 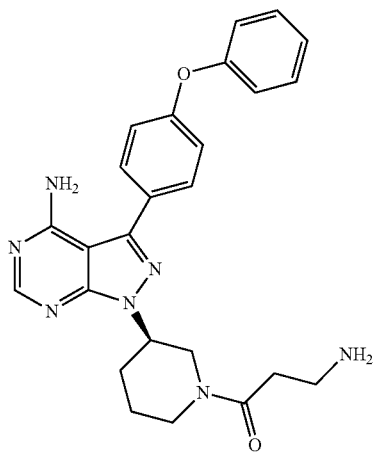 [SMILES: NCCC(=O)N1CCC[C@@H](n2nc(-c3ccc(Oc4ccccc4)cc3)c3c(N)ncnc32)C1] |
| Compound 47 | 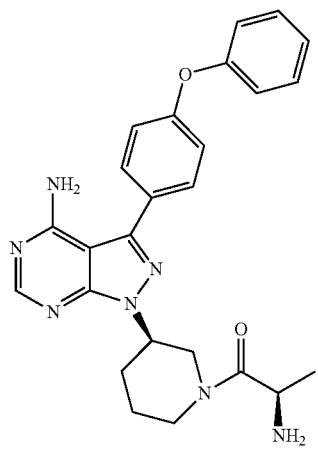 [SMILES: C[C@@H](N)C(=O)N1CCC[C@@H](n2nc(-c3ccc(Oc4ccccc4)cc3)c3c(N)ncnc32)C1] |
| Compound 48 | 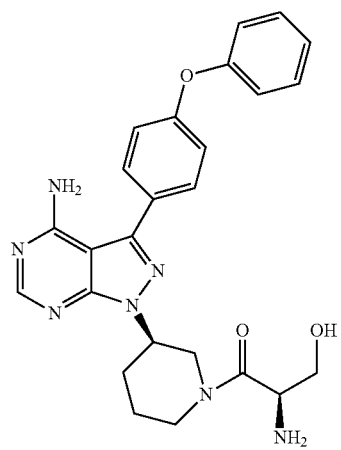 [SMILES: Nc1ncnc2c1c(-c1ccc(Oc3ccccc3)cc1)nn2[C@@H]1CCCN(C(=O)[C@H](N)CO)C1] |
| Compound 52 | 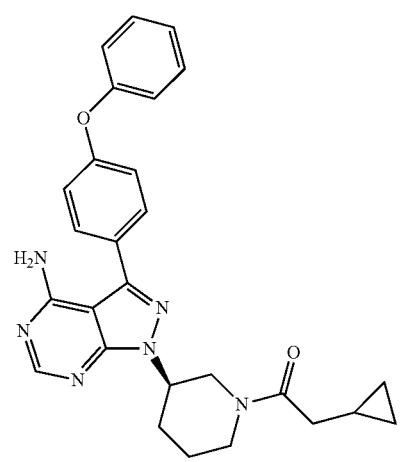 [SMILES: Nc1ncnc2c1c(-c1ccc(Oc3ccccc3)cc1)nn2[C@@H]1CCCN(C(=O)CC2CC2)C1] |
| Compound 56 | 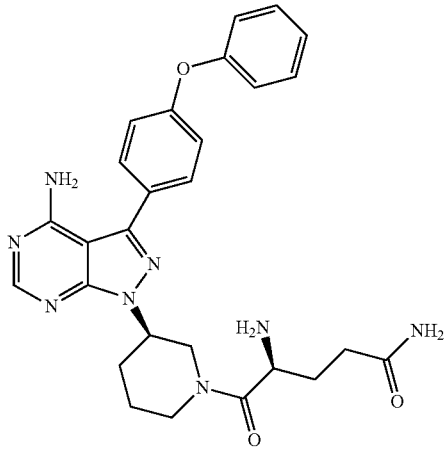 [SMILES: NC(=O)CC[C@H](N)C(=O)N1CCC[C@@H](n2nc(-c3ccc(Oc4ccccc4)cc3)c3c(N)ncnc32)C1] |

Compound 57
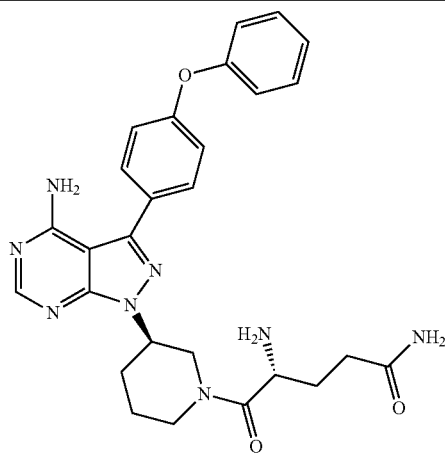

Compound 58
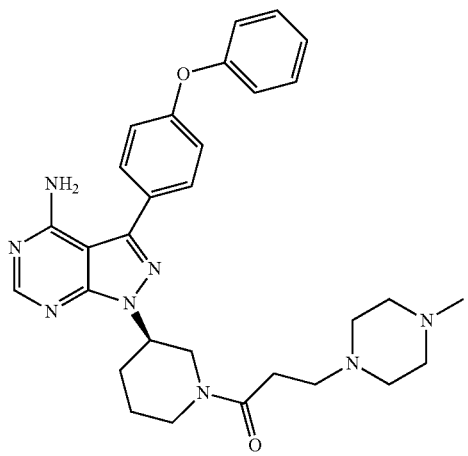 [SMILES: CN1CCN(CCC(=O)N2CCC[C@@H](n3nc(-c4ccc(Oc5ccccc5)cc4)c4c(N)ncnc43)C2)CC1]

Compound 59
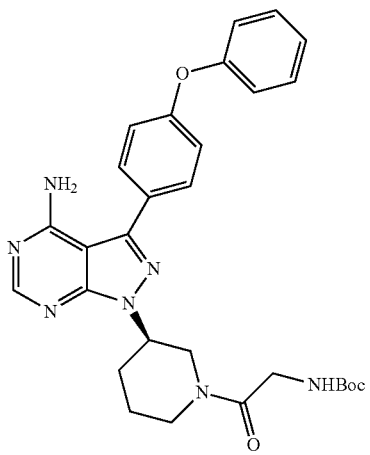 [SMILES: CC(C)(C)OC(=O)NCC(=O)N1CCC[C@@H](n2nc(-c3ccc(Oc4ccccc4)cc3)c3c(N)ncnc32)C1]

Compound 60
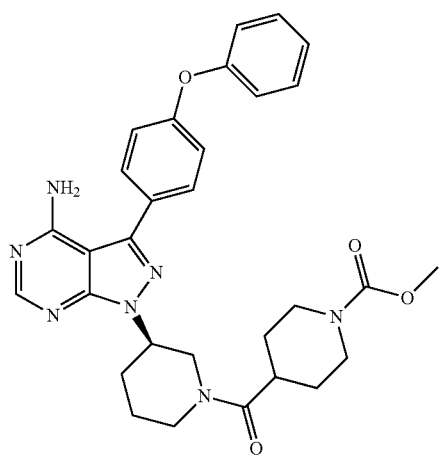 [SMILES: COC(=O)N1CCC(C(=O)N2CCC[C@@H](n3nc(-c4ccc(Oc5ccccc5)cc4)c4c(N)ncnc43)C2)CC1]

Compound 62
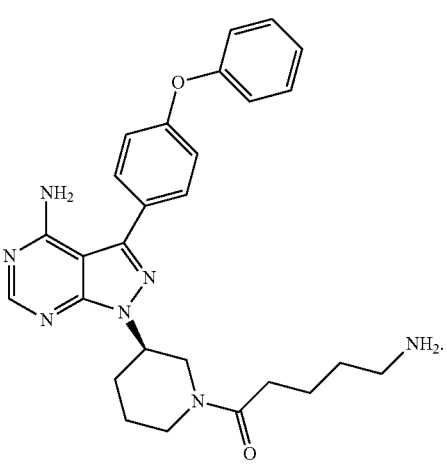 [SMILES: NCCCCC(=O)N1CCC[C@@H](n2nc(-c3ccc(Oc4ccccc4)cc3)c3c(N)ncnc32)C1]

5. A pharmaceutical composition comprising the compound, or a pharmaceutically acceptable salt, solvate, isomer, ester, acid, metabolite or prodrug thereof, according to claim 1, a pharmaceutically acceptable carrier or excipient, and optionally other therapeutic agents.

6. A method for inhibiting the activity of FLT3 kinase and/or mutant FLT3 kinase in a cell or a subject, comprising administering an effective amount of the compound of claim 1 to the cell or the subject.

7. A method for the treatment of acute lymphocytic leukemia, comprising administering a therapeutically effective amount of the compound of claim 1 to a patient in need of said treatment.

* * * * *